(12) United States Patent
Sherman et al.

(10) Patent No.: US 8,148,978 B2
(45) Date of Patent: *Apr. 3, 2012

(54) MAGNETIC SENSOR ARRAY

(75) Inventors: Jason T. Sherman, Leesburg, IN (US); Mark R. DiSilvestro, Columbia City, IN (US); Radivoje S. Popovic, St-Sulpice (CH)

(73) Assignee: DePuy Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/388,122

(22) Filed: Feb. 18, 2009

(65) Prior Publication Data
US 2009/0189603 A1    Jul. 30, 2009

Related U.S. Application Data

(63) Continuation of application No. 11/323,610, filed on Dec. 30, 2005, now Pat. No. 7,525,309.

(51) Int. Cl.
*G01R 33/02* (2006.01)
*G01B 7/14* (2006.01)

(52) U.S. Cl. .................. 324/247; 324/207.13; 324/258

(58) Field of Classification Search ............ 324/207.13, 324/207.15, 207.16, 207.17, 244, 247, 258; 702/150, 152, 153; 600/424
See application file for complete search history.

(56) References Cited

U.S. PATENT DOCUMENTS

| | | | |
|---|---|---|---|
| 3,847,157 A | 11/1974 | Caillouette et al. | |
| 4,054,881 A | 10/1977 | Raab | |
| 4,063,561 A | 12/1977 | McKenna | |
| 4,173,228 A | 11/1979 | Van Steenwyk et al. | |
| 4,244,362 A | 1/1981 | Anderson | |
| 4,328,548 A | 5/1982 | Crow et al. | |
| 4,396,885 A | 8/1983 | Constant | |
| 4,422,041 A | 12/1983 | Lienau | |
| 4,431,005 A | 2/1984 | McCormick | |
| 4,622,644 A | 11/1986 | Hansen | |
| 4,652,820 A | 3/1987 | Maresca | |

(Continued)

FOREIGN PATENT DOCUMENTS

CA    2517250 A1    9/2004

(Continued)

OTHER PUBLICATIONS

European Search Report for European Patent Application No. 06256546.0-2310/1803413, Jul. 8, 2008, 16 pages.

(Continued)

*Primary Examiner* — Reena Aurora
(74) *Attorney, Agent, or Firm* — Barnes & Thornburg LLP

(57) ABSTRACT

A magnetic sensor array includes a first three-dimensional magnetic sensor secured to a substrate in a central location of the substrate. A number of second three-dimensional magnetic sensors are secured to the substrate at a first distance from the first magnetic sensor. Additionally, a number of one-dimensional magnetic sensors are secured to the substrate at a second distance from the first magnetic sensor greater than the first distance. Additional magnetic sensors of any dimension may also be included. The magnetic field sensitivity of the first and second three-dimensional magnetic sensors may be less than the magnetic field sensitivity of the one-dimensional magnetic sensors. The sensing range of the first and second three-dimensional magnetic sensors may be greater than the sensing range of the one-dimensional magnetic sensors. The magnetic sensor array may also include a processing circuit coupled to the magnetic sensors.

14 Claims, 36 Drawing Sheets

U.S. PATENT DOCUMENTS

| | | | |
|---|---|---|---|
| 4,661,773 A | 4/1987 | Kawakita et al. |
| 4,677,380 A | 6/1987 | Popovic et al. |
| 4,700,211 A | 10/1987 | Popovic et al. |
| 4,710,708 A | 12/1987 | Rorden et al. |
| 4,790,809 A | 12/1988 | Kuntz |
| 4,791,934 A | 12/1988 | Brunnett |
| 4,809,713 A | 3/1989 | Grayzel |
| 4,829,250 A | 5/1989 | Rotier |
| 4,849,692 A | 7/1989 | Blood |
| 4,905,698 A | 3/1990 | Strohl, Jr. et al. |
| 4,943,770 A | 7/1990 | Ashley-Rollman et al. |
| 5,099,845 A | 3/1992 | Beszer et al. |
| 5,113,136 A | 5/1992 | Hayashi et al. |
| 5,206,589 A | 4/1993 | Kado et al. |
| 5,211,165 A | 5/1993 | Dumouline et al. |
| 5,218,299 A | 6/1993 | Dunkel |
| 5,251,635 A | 10/1993 | Dumouline et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,273,025 A | 12/1993 | Sakiyama et al. |
| 5,377,678 A | 1/1995 | Dumoulin et al. |
| 5,383,454 A | 1/1995 | Bucholz |
| 5,389,101 A | 2/1995 | Heibrun et al. |
| 5,425,382 A | 6/1995 | Golden et al. |
| 5,438,990 A | 8/1995 | Wahlstrand et al. |
| 5,456,718 A | 10/1995 | Szymaitis |
| 5,558,091 A | 9/1996 | Acker et al. |
| 5,622,169 A | 4/1997 | Golden et al. |
| 5,631,557 A | 5/1997 | Davidson |
| 5,648,719 A | 7/1997 | Christensen et al. |
| 5,694,040 A | 12/1997 | Plagens |
| 5,711,299 A | 1/1998 | Manwarig et al. |
| 5,713,946 A | 2/1998 | Ben-Haim |
| 5,729,129 A | 3/1998 | Acker |
| 5,731,996 A | 3/1998 | Gilbert |
| 5,752,513 A | 5/1998 | Acker et al. |
| 5,761,332 A | 6/1998 | Wischmann |
| 5,762,064 A | 6/1998 | Polvani |
| 5,775,322 A | 7/1998 | Silverstein et al. |
| 5,799,099 A | 8/1998 | Wang et al. |
| 5,833,608 A | 11/1998 | Acker |
| 5,834,709 A | 11/1998 | Blonder et al. |
| 5,842,986 A | 12/1998 | Avrin et al. |
| 5,879,297 A | 3/1999 | Haynor et al. |
| 5,902,238 A | 5/1999 | Golden et al. |
| 5,913,820 A | 6/1999 | Bladen et al. |
| 5,942,895 A | 8/1999 | Popovic et al. |
| 5,944,022 A | 8/1999 | Nardella et al. |
| 5,944,023 A | 8/1999 | Johnson et al. |
| 5,967,980 A | 10/1999 | Ferre et al. |
| 5,983,126 A | 11/1999 | Wittkampf |
| 5,987,349 A | 11/1999 | Schulz |
| 6,015,414 A | 1/2000 | Werp et al. |
| 6,052,610 A | 4/2000 | Koch |
| 6,059,718 A | 5/2000 | Taniguchi et al. |
| 6,064,905 A | 5/2000 | Webster et al. |
| 6,073,043 A | 6/2000 | Schneider |
| 6,076,007 A | 6/2000 | England et al. |
| 6,104,944 A | 8/2000 | Martinelli |
| 6,122,538 A | 9/2000 | Sliwa, Jr. et al. |
| 6,129,668 A | 10/2000 | Haynor et al. |
| 6,146,390 A | 11/2000 | Heibrun et al. |
| 6,147,480 A | 11/2000 | Osadchy et al. |
| 6,148,823 A | 11/2000 | Hastings |
| 6,157,853 A | 12/2000 | Blume et al. |
| 6,161,032 A | 12/2000 | Acker |
| 6,165,181 A | 12/2000 | Heibrun et al. |
| 6,167,145 A | 12/2000 | Foley et al. |
| 6,167,292 A | 12/2000 | Badano et al. |
| 6,173,715 B1 | 1/2001 | Sinanan et al. |
| 6,177,792 B1 | 1/2001 | Govari et al. |
| 6,184,679 B1 | 2/2001 | Popovic et al. |
| 6,185,448 B1 | 2/2001 | Borovsky |
| 6,198,963 B1 | 3/2001 | Haim et al. |
| 6,201,387 B1 | 3/2001 | Govari |
| 6,203,493 B1 | 3/2001 | Ben-Haim |
| 6,210,362 B1 | 4/2001 | Ponzi |
| 6,211,666 B1 | 4/2001 | Acker |
| 6,212,419 B1 | 4/2001 | Blume et al. |
| 6,216,028 B1 | 4/2001 | Haynor et al. |
| 6,230,038 B1 | 5/2001 | Von Gutfeld et al. |
| 6,235,038 B1 | 5/2001 | Hunter et al. |
| 6,236,875 B1 | 5/2001 | Bucholz et al. |
| 6,241,671 B1 | 6/2001 | Ritter et al. |
| 6,246,900 B1 | 6/2001 | Cosman et al. |
| 6,263,230 B1 | 7/2001 | Haynor et al. |
| 6,285,902 B1 | 9/2001 | Kienzle, III et al. |
| 6,292,678 B1 | 9/2001 | Hall et al. |
| 6,304,768 B1 | 10/2001 | Blume et al. |
| 6,304,769 B1 | 10/2001 | Arenson et al. |
| 6,311,082 B1 | 10/2001 | Creighton, IV et al. |
| 6,314,310 B1 | 11/2001 | Ben-Haim et al. |
| 6,321,109 B2 | 11/2001 | Ben-Haim et al. |
| 6,332,089 B1 | 12/2001 | Acker et al. |
| 6,341,231 B1 | 1/2002 | Ferre et al. |
| 6,347,240 B1 | 2/2002 | Foley et al. |
| 6,366,799 B1 | 4/2002 | Acker et al. |
| 6,370,224 B1 | 4/2002 | Simon et al. |
| 6,373,240 B1 | 4/2002 | Govari |
| 6,374,134 B1 | 4/2002 | Bladen et al. |
| 6,381,485 B1 | 4/2002 | Hunter et al. |
| 6,385,472 B1 | 5/2002 | Hall et al. |
| 6,401,723 B1 | 6/2002 | Garibaldi et al. |
| 6,402,762 B2 | 6/2002 | Hunter et al. |
| 6,405,072 B1 | 6/2002 | Cosman |
| 6,418,335 B2 | 7/2002 | Avrin et al. |
| 6,424,856 B1 | 7/2002 | Vilsmeier et al. |
| 6,427,079 B1 | 7/2002 | Schneider et al. |
| 6,427,314 B1 | 8/2002 | Acker |
| 6,428,551 B1 | 8/2002 | Hall et al. |
| 6,430,434 B1 | 8/2002 | Mittelstadt |
| 6,434,415 B1 | 8/2002 | Foley et al. |
| 6,442,416 B1 | 8/2002 | Schultz |
| 6,445,943 B1 | 9/2002 | Ferre et al. |
| 6,459,924 B1 | 10/2002 | Creighton, IV et al. |
| 6,474,341 B1 | 11/2002 | Hunter et al. |
| 6,475,223 B1 | 11/2002 | Werp et al. |
| 6,490,467 B1 | 12/2002 | Bucholz et al. |
| 6,491,702 B2 | 12/2002 | Heibrun et al. |
| 6,493,573 B1 | 12/2002 | Martinelli et al. |
| 6,496,713 B2 | 12/2002 | Avrin et al. |
| 6,498,477 B1 | 12/2002 | Govari et al. |
| 6,499,488 B1 | 12/2002 | Hunter et al. |
| 6,505,062 B1 | 1/2003 | Ritter et al. |
| 6,507,751 B2 | 1/2003 | Blume et al. |
| 6,511,417 B1 | 1/2003 | Taniguchi et al. |
| 6,516,212 B1 | 2/2003 | Bladen et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,529,761 B2 | 3/2003 | Creighton, IV et al. |
| 6,535,756 B1 | 3/2003 | Simon et al. |
| 6,537,196 B1 | 3/2003 | Creighton, IV et al. |
| 6,539,327 B1 | 3/2003 | Dassot et al. |
| 6,545,462 B2 | 4/2003 | Schott et al. |
| 6,546,279 B1 | 4/2003 | Bova et al. |
| 6,553,326 B1 | 4/2003 | Kirsch et al. |
| 6,574,492 B1 | 6/2003 | Ben-Haim et al. |
| 6,574,498 B1 | 6/2003 | Gilboa |
| 6,580,938 B1 | 6/2003 | Acker |
| 6,584,174 B2 | 6/2003 | Schubert et al. |
| 6,593,884 B1 | 7/2003 | Gilboa et al. |
| 6,611,141 B1 | 8/2003 | Schulz et al. |
| 6,618,612 B1 | 9/2003 | Acker et al. |
| 6,622,098 B2 | 9/2003 | Updegrove |
| 6,625,563 B2 | 9/2003 | Kirsch et al. |
| 6,633,773 B1 | 10/2003 | Reisfeld |
| 6,640,127 B1 | 10/2003 | Kosaka et al. |
| 6,662,034 B2 | 12/2003 | Segner et al. |
| 6,662,036 B2 | 12/2003 | Cosman |
| 6,687,531 B1 | 2/2004 | Ferre et al. |
| 6,690,963 B2 | 2/2004 | Ben-Haim et al. |
| 6,701,174 B1 | 3/2004 | Krause et al. |
| 6,701,179 B1 | 3/2004 | Martinelli et al. |
| 6,702,804 B1 | 3/2004 | Ritter et al. |

| | | |
|---|---|---|
| 6,725,080 B2 | 4/2004 | Melkent et al. |
| 6,733,511 B2 | 5/2004 | Hall et al. |
| 6,738,656 B1 | 5/2004 | Ferre et al. |
| 6,740,103 B2 | 5/2004 | Hall et al. |
| 6,755,816 B2 | 6/2004 | Ritter et al. |
| 6,757,557 B1 | 6/2004 | Bladen et al. |
| 6,772,002 B2 | 8/2004 | Schmidt et al. |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,892,090 B2 | 5/2005 | Verard et al. |
| 6,895,267 B2 | 5/2005 | Panescu et al. |
| 6,902,528 B1 | 6/2005 | Garibaldi et al. |
| 6,911,026 B1 | 6/2005 | Hall et al. |
| 6,920,347 B2 | 7/2005 | Simon et al. |
| 6,925,339 B2 | 8/2005 | Grimm et al. |
| 6,934,575 B2 | 8/2005 | Ferre et al. |
| 6,937,906 B2 | 8/2005 | Terry et al. |
| 6,947,786 B2 | 9/2005 | Simon et al. |
| 6,968,846 B2 | 11/2005 | Viswanathan |
| 6,977,504 B2 | 12/2005 | Wright et al. |
| 6,977,594 B2 | 12/2005 | Hudman et al. |
| 6,978,166 B2 | 12/2005 | Foley et al. |
| 7,525,309 B2 * | 4/2009 | Sherman et al. ............. 324/247 |
| 2001/0011175 A1 | 8/2001 | Hunter et al. |
| 2001/0039421 A1 | 11/2001 | Heilbrun et al. |
| 2002/0016542 A1 | 2/2002 | Blume et al. |
| 2002/0019644 A1 | 2/2002 | Hastings et al. |
| 2002/0021124 A1 | 2/2002 | Schott et al. |
| 2002/0030483 A1 | 3/2002 | Gilboa |
| 2002/0032380 A1 | 3/2002 | Acker et al. |
| 2002/0087062 A1 | 7/2002 | Schmidt et al. |
| 2002/0100486 A1 | 8/2002 | Creighton, IV et al. |
| 2002/0116043 A1 | 8/2002 | Garibaldi et al. |
| 2002/0183610 A1 | 12/2002 | Foley et al. |
| 2002/0188194 A1 | 12/2002 | Cosman |
| 2003/0006759 A1 | 1/2003 | Govari |
| 2003/0023161 A1 | 1/2003 | Govari et al. |
| 2003/0040671 A1 | 2/2003 | Somogyi et al. |
| 2003/0088179 A1 | 5/2003 | Seeley et al. |
| 2003/0090265 A1 | 5/2003 | Wan et al. |
| 2003/0153827 A1 | 8/2003 | Ritter et al. |
| 2003/0179856 A1 | 9/2003 | Mitschke et al. |
| 2004/0021507 A1 | 2/2004 | Fischer |
| 2004/0046558 A1 | 3/2004 | Matsumoto |
| 2004/0073279 A1 | 4/2004 | Malachowski et al. |
| 2004/0207396 A1 | 10/2004 | Xiao |
| 2004/0215071 A1 | 10/2004 | Frank et al. |
| 2004/0232913 A1 | 11/2004 | Schott et al. |
| 2004/0249262 A1 | 12/2004 | Werp et al. |
| 2004/0260172 A1 | 12/2004 | Ritter et al. |
| 2005/0010301 A1 | 1/2005 | Disilvestro et al. |
| 2005/0015003 A1 | 1/2005 | Lachner et al. |
| 2005/0027492 A1 | 2/2005 | Taylor et al. |
| 2005/0059879 A1 | 3/2005 | Sutherland et al. |
| 2005/0070916 A1 | 3/2005 | Hollstien |
| 2005/0075561 A1 | 4/2005 | Golden |
| 2005/0075562 A1 | 4/2005 | Szakelyhidi, Jr. et al. |
| 2005/0182315 A1 | 8/2005 | Ritter et al. |
| 2005/0245821 A1 | 11/2005 | Govari et al. |
| 2005/0273130 A1 | 12/2005 | Sell |
| 2006/0011999 A1 | 1/2006 | Schott et al. |
| 2007/0161888 A1 | 7/2007 | Sherman et al. |
| 2007/0163367 A1 | 7/2007 | Sherman et al. |
| 2007/0167703 A1 | 7/2007 | Sherman et al. |
| 2007/0167741 A1 | 7/2007 | Sherman et al. |
| 2007/0270722 A1 | 11/2007 | Loeb et al. |
| 2008/0012558 A1 | 1/2008 | Rossler et al. |
| 2008/0154127 A1 | 6/2008 | DiSilvestro et al. |

FOREIGN PATENT DOCUMENTS

| | | |
|---|---|---|
| DE | 4014947 A1 | 11/1991 |
| DE | 10037491 A1 | 2/2002 |
| EP | 0993804 A1 | 4/2000 |
| EP | 1020734 A2 | 7/2000 |
| EP | 1081647 A1 | 3/2001 |
| EP | 1181891 A2 | 2/2002 |
| EP | 1184684 A2 | 3/2002 |
| EP | 0983018 B1 | 11/2002 |
| EP | 1302172 A1 | 4/2003 |
| EP | 1348394 A1 | 10/2003 |
| EP | 1447055 A1 | 8/2004 |
| EP | 1493384 | 1/2005 |
| EP | 1530057 A2 | 5/2005 |
| EP | 1570781 A1 | 9/2005 |
| GB | 1283521 A | 7/1972 |
| GB | 2102127 A | 1/1983 |
| JP | 20044283606 | 10/2004 |
| WO | 93/04628 | 3/1993 |
| WO | 9509562 A2 | 4/1995 |
| WO | 96/08999 A1 | 3/1996 |
| WO | 98/32387 A1 | 7/1996 |
| WO | 96/41119 A1 | 12/1996 |
| WO | 97/48438 A2 | 12/1997 |
| WO | 97/49445 A1 | 12/1997 |
| WO | 98/49938 A1 | 11/1998 |
| WO | 98/52466 A1 | 11/1998 |
| WO | 9949783 A1 | 10/1999 |
| WO | 99/59106 A1 | 11/1999 |
| WO | 00/15286 A1 | 3/2000 |
| WO | 00/27281 A2 | 5/2000 |
| WO | 00/51514 A1 | 9/2000 |
| WO | 00/74372 A1 | 12/2000 |
| WO | 01/17600 A1 | 3/2001 |
| WO | 01/22368 A1 | 3/2001 |
| WO | 0124697 A1 | 4/2001 |
| WO | 0130257 A1 | 5/2001 |
| WO | 0237935 A2 | 5/2002 |
| WO | 02062249 A1 | 8/2002 |
| WO | 02/103618 A1 | 12/2002 |
| WO | 03/051514 A1 | 6/2003 |
| WO | 03090022 A2 | 10/2003 |
| WO | 03096870 A2 | 11/2003 |
| WO | 2004095044 | 11/2004 |
| WO | 2005/044081 A2 | 5/2005 |
| WO | 2005067563 | 7/2005 |
| WO | 2005/086062 A1 | 9/2005 |
| WO | 2005/087125 A2 | 9/2005 |
| WO | 2005084572 A2 | 9/2005 |
| WO | 2005/119505 A2 | 12/2005 |

OTHER PUBLICATIONS

European Search Report for European Patent Application No. 06256546.0-2310, Apr. 15, 2008, 7 pages.

Ip et al., "Arbitrary Facial Views Generation from Two Orthogonal Facial Images", IEEE, 1995, pg.

Nikkhahe-Dehkordi et al., "3D Reconstruction of the Femoral Bone using Two X-ray Images from Orthogonal Views", Article retrieved from http://www.lab3d.odont.ku.dk/Documents/Pubs-96/FemurCAR96/femur.html , Jul. 20, 2005, 5 pgs.

Lötjönen et al., "Reconstruction of 3-D Geometry Using 2-D Profiles and a Geometric Prior Model", IEEE Transactions on Medical Imaging, vol. 18, No. 10, Oct. 1999.

S. Delorme, "Three-Dimensional Modelling and Rendering of the Human Skeletal Trunk from 2D Radiographic Images", Abstract retrieved from http://doi.ieeecomputersociety.org/10/1109/IM.1999.805382 , 1 pg.

Andrés del Valle et al., "3D Talking Head Customization by Adaptating a Generic Model to One Uncalibrated Picture", IEEE, 2001, pp. II-325-II-328.

Messmer et al., "Volumetric Model Determination of the Tibia Based on 2D Radiographs Using a 2D/3D Database", Computer Aided Surgery, vol. 6, 2001, pp. 183-194.

Benameur et al., "3D Biplanar Reconstruction of Scoliotic Vertebrae Using Statistical Models", Abstract retrieved from http://doi.ieeecomputersociety.org/10.1109/CVPR.2001.991014 , 2 pgs.

Laporte et al., "A biplanar reconstruction method based on 2D and 3D contours: application to the distal femur", Computer Methods in Biomechanics and Biomedical Engineering (Abstract Only), Feb. 2003, vol. 6, No. 1, 2 pgs.

Yao et al., "Assessing Accuracy Factors in Deformable 2D/3D Medical Image Registration Using a Statistical Pelvis Model", Abstract retrieved from http://doi.ieeecomputersociety.org/10.1109/ICCV.2003.1238644 , 1 pg.

Livyatan et al., "Gradient-Based 2-D/3-D Rigid Registration of Fluoroscopic X-Ray to CT", IEEE Transactions on Medical Imaging; vol. 22, No. 11, Nov. 2003, pp. 1395-1406.

Rajamani, "A Novel Approach to Anatomical Structure Morphing for Intraoperative Visualization", Medical Image Computing and Computer-Assisted Intervention—MICCAI 2004, 7th Conference, Saint-Malo, France, Sep. 2004 Proceedings, Part II, LNCS 3217, pp. 478-485.

Wu et al., "A Two-Level Method for Building a Statistical Shape Atlas", The Robotics Institute, Carnegie Mellon University, Pittsburgh, PA and CAOS: Institute for Computer Assisted Orthopaedic Surgery, The Western Pennsylvania Hospital, Pittsburgh, PA, 2005, Jun. 2005, 2 pgs.

Gao, Nuo, Detecting Human Head Conductivity Distribution Using One Component Magnetic Flux Density, Sep. 2005, IEEE, pp. 1537-1539.

Prakash, N., Localization of a Magnetic Marker for GI Motility Studies: An In Vitro Feasibility Study, IEEE, 1007, pp. 2394-2397, 1997.

Raab, F., "Magnetic Position and Orientation Tracking System," 1979, IEEE, vol. 15, No. 5, pp. 709-717.

Schlageter, V., "Tracking system with five degrees of freedom using a 2D-array of Hall sensors and a permanent magnet," 2001, Elsevier, pp. 37-42.

Schlageter, V., Tracking system with five degrees of freedom using a 2D-array of Hall sensors and a permanent magnet, pp. 679-682, From the 14th European conference on Solid-State Transducers, Aug. 27-30, 2000, Copenhagen, Denmark, ISBN No. 87-89935-50-0.

Ybukami, S., "Motion Capture System of Magnetic Makers Using Three-Axial Magnetic Field Sensor," 2000, IEEE, vol. 36, No. 5, pp. 3646-3648.

Australian Office Action for Australian Patent Application No. 2006252293, May 18, 2010, 5 pgs.

Australian Office Action for Australian Patent Application No. 2006252294, Jun. 1, 2010, 2 pgs.

Australian Office Action for Australian Patent Application No. 2006252291, Apr. 13, 2011, 4 pgs.

European Search Report for European Patent Application No. 06256541.1-1265, Apr. 17, 2007, 9 pgs.

European Search Report for European Application No. 06256549.4-2318, May 10, 2007, 12 pgs.

European Search Report for European Application No. 06256574.2-1526, Feb. 12, 2008, 6 pgs.

European Search Report for European Patent Application No. 07255016.3-2218, Apr. 18, 2008, 6 pgs.

Office Action for European Patent Application No. 06256549.4-2310, Jul. 13, 2009, 4 pgs.

\* cited by examiner

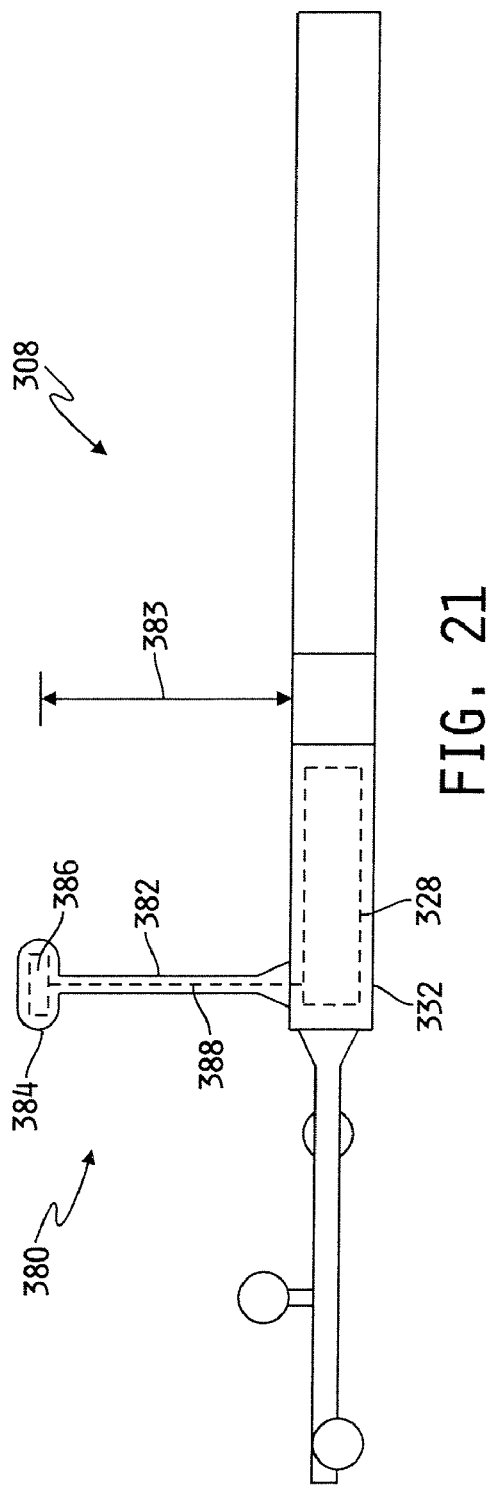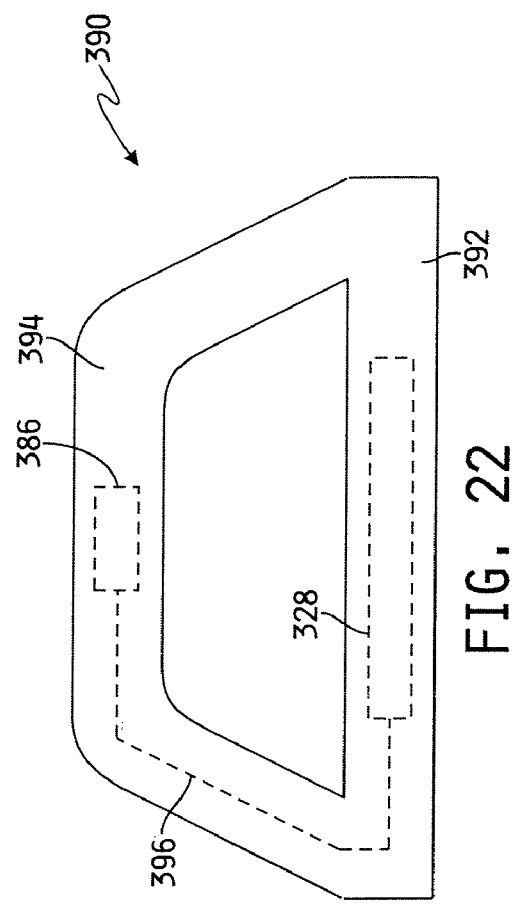

MAGNETIC SENSOR ARRAY

This patent application is a continuation of U.S. patent application Ser. No. 11/323,610, filed Dec. 30, 2005, the entirety of which is hereby incorporated herein by reference.

CROSS-REFERENCE TO RELATED U.S. PATENT APPLICATION

Cross-reference is made to U.S. Utility patent application Ser. No. 11/323,963 entitled "SYSTEM AND METHOD FOR REGISTERING A BONE OF A PATIENT WITH A COMPUTER ASSISTED ORTHOPAEDIC SURGERY SYSTEM," which was filed on Dec. 30, 2005 by Jason T. Sherman et al., to U.S. Utility patent application Ser. No. 11/323,609 entitled "APPARATUS AND METHOD FOR REGISTERING A BONE OF A PATIENT WITH A COMPUTER ASSISTED ORTHOPAEDIC SURGERY SYSTEM," which was filed on Dec. 30, 2005 by Jason T. Sherman et al., and to U.S. Utility patent application Ser. No. 11/323,537 entitled "METHOD FOR DETERMINING A POSITION OF A MAGNETIC SOURCE," which was filed on Dec. 30, 2005 by Jason T. Sherman et al., the entirety of all of which is expressly incorporated herein by reference.

TECHNICAL FIELD

The present disclosure relates generally to computer assisted surgery systems for use in the performance of orthopaedic procedures.

BACKGROUND

There is an increasing adoption of minimally invasive orthopaedic procedures. Because such surgical procedures generally restrict the surgeon's ability to see the operative area, surgeons are increasingly relying on computer systems, such as computer assisted orthopaedic surgery (CAOS) systems, to assist in the surgical operation.

Computer assisted orthopaedic surgery (CAOS) systems assist surgeons in the performance of orthopaedic surgical procedures by, for example, displaying images illustrating surgical steps of the surgical procedure being performed and rendered images of the relevant bones of the patient. Before a computer assisted orthopaedic surgery (CAOS) system can display a rendered image of a bone, the bone must first be registered with the computer assisted orthopaedic surgery (CAOS) system. Registering the bone with the computer assisted orthopaedic surgery (CAOS) system allows the system to determine the relevant contour, location, and orientation of the bone and display the rendered image according to such parameters. In typical computer assisted orthopaedic surgery (CAOS) systems, a bone is registered by touching a number of locations of the bone with a probe. In response, the system computes a rendered image of the bone, including the contour of the bone, based on the recorded locations. Because the typical registration process occurs during the orthopaedic surgery procedure, the typical registration process may add additional surgery time and increase the time during which the patient is exposed to possible infection. Moreover, current registration of the bony anatomy of particular skeletal areas, such as the hip joint, are challenging due to the difficulty of fiducial markers and anatomical planes.

SUMMARY

According to one aspect, a method for operating a computer assisted orthopaedic surgery system includes determining a position of a magnetic source coupled to a bone of a patient. The position of the magnetic source may be determined based on a magnetic field generated by the magnetic source. Determining a position of the magnetic source may include sensing the magnetic field. For example, determining a position of the magnetic source may include sensing a three dimensional magnetic flux density or portion thereof. The magnetic source may include one or more magnets. For example, the magnetic source may include a cylindrical, dipole magnet(s). The magnetic source may be coupled to the bone via implanting the magnetic source into the bone. The magnetic source may be implanted using a jig. In embodiments wherein the magnetic source includes two or more magnets, the magnets may be implanted at any orientation relative to each other. For example, the magnets may be implanted orthogonal to each other. Additionally, the magnets may be implanted a distance apart from each other such that the individual magnetic fields do not substantially interfere with each other. For example, the magnets may be implanted two times or more the maximum sensing distance of a magnet sensor or collection of magnetic sensors such as, a magnetic sensor array.

The magnetic sensor array may be embodied as one or more magnetic sensors. The magnetic sensors may measure the scalar components or magnitude of any or all components of the three-dimensional magnetic flux density of the magnetic field of the magnetic source at a point in space (i.e., the location of the magnetic source). The magnetic sensor array may also include a housing for positioning the magnetic sensors in the magnetic field of the magnetic source(s). The magnetic sensor array may further include a processing circuit electrically coupled to the magnetic sensors and configured to determine position data indicative of the position of the magnetic source relative to the magnetic sensor array. For example, the processing circuit may be configured to determine a number of coefficients indicative of the six degrees of freedom of the magnetic source. To do so, the magnetic sensor array may determine an initial estimate of the position of the magnetic source. Based on the initial estimate, the magnetic sensor array may determine one or more components of the theoretical magnetic flux density of the magnetic source. The magnetic sensor array may also determine a sum of errors between the theoretical and measured values of the magnetic flux density. The magnetic sensor array may be also be configured to optimize the sum of error by determining a new estimate for the position of the magnetic source using a global or local optimization algorithm.

The magnetic sensor array may also include a transmitter, such as a wireless transmitter, electrically coupled to the processing circuit for transmitting position data to, for example, a controller or computer of a CAOS system. The magnetic sensor array may also include an indicator, such as a visual indicator, that is activated by the processing circuit while the magnetic flux density sensed by the magnetic sensors is above a predetermined threshold value. The magnetic sensor array may further include a register button selectable by a user to cause the magnetic sensor array to transmit sensory data to the controller via, for example, the wireless transmitter. A reflective sensor array may also be coupled to the magnetic sensor array. Via cooperation of the reflective sensor array and a camera of the computer assisted orthopaedic surgery (CAOS) system, the position of the magnetic sensor array relative to the computer assisted orthopaedic surgery (CAOS) system can be determined.

Output signals of the magnetic sensor array (e.g., of the magnetic sensor(s)) may be adjusted to account for environmental magnetic fields such as the Earth's magnetic field and/or offset biases of the magnetic sensors included in the magnetic sensor array. Further, the measurements of the magnetic sensor array may be verified prior to the registration process or as part of a maintenance process by use of a test apparatus having a test magnetic source of known magnetic strength or flux density and distance from the magnetic sensor array.

The method may also include determining position data indicative of a position of the magnetic source based on the magnetic field. Determining position data may include determining a position of the magnetic source relative to a magnetic sensor array and/or determining a position of a magnetic sensor array relative to the computer assisted orthopaedic surgery (CAOS) system. Determining position data may also include determining values of the six degrees of freedom of the magnetic source (i.e., three orthogonal spatial coordinates and three angles of rotation about each orthogonal axis).

The method may further include retrieving an image of the bone from a database or other storage location. The image may be any type of pre-generated three-dimensional image of the bone including indicia of the relative position of the magnetic source (e.g., the position of the magnet(s)). The method may include determining a positional relationship, such as a vector, between the bone and the magnetic source. The method may yet further include creating a graphically rendered image of the bone based on the retrieved image, the position data, and the positional relationship between the bone and the magnetic source. The graphically rendered image of the bone may include surface contours determined based on the image data. The graphically rendered image may be displayed in a location and orientation based on the position data. The method may also include locating the magnetic source with a magnetic sensor array after the creating step. The magnetic source may then be decoupled from the bone after it is located with the magnetic sensor array.

According to another aspect, a computer assisted surgery system includes a display device, a processor electrically coupled to the display device, and a memory device electrically coupled to the processor. The memory device may have stored therein a plurality of instructions, which when executed by the processor, may cause the processor to receive position data indicative of a position of a magnetic source coupled to a bone of a patient. The position data may be received (e.g., wirelessly received) from a magnetic sensor array. The plurality of instructions may also cause the processor to determine a position of the magnetic sensor array relative to a reference point such as a camera or controller of the system. The plurality of instructions may further cause the processor to retrieve an image of the bone of the patient from a database and display a graphically rendered image of the bone on the display device in a location and orientation based on the retrieved image and the determining step.

According to a further aspect, a method for registering a bone with a CAOS system may include coupling a magnetic source to a bone of the patient. As discussed above, the magnetic source may include one or more magnets such as, for example, cylindrical, dipole magnets. The magnetic source may be coupled to the bone by implanting the magnetic source in the bone. In embodiments wherein the magnetic source includes two or more magnets, a jig may be used to couple the magnets to the bone. The magnets may be coupled to the bone at a predetermined angle with respect to each other. Alternatively, the two or more magnets may be coupled to each other with a support member such that their position (location and orientation) relative to each other is fixed. In addition, the magnets may be coupled at a distance from each other such that the individual magnetic fields of each magnet do not substantially interfere with the magnetic field of other magnets which form the magnetic source. For example, in some embodiments, the magnets are coupled a distance from each other that is at least twice the distance of the desired maximum sensing distance for the magnetic source.

The method may also include generating an image of the bone subsequent to the coupling step. The image may include indicia of the position of the magnetic source relative to the bone. The method may further include determining a position of the magnetic source based on a magnetic field generated by the magnetic source. The method may yet further include creating a graphically rendered image of the bone based on the retrieved image, the position data, and a positional relationship between the bone and the magnetic source. The graphically rendered image of the bone may include surface contours determined based on the image data. The graphically rendered image may be displayed in a location and orientation based on the position data. The method may also include locating the magnetic source with a magnetic sensor array after the creating step. The magnetic source may then be decoupled from the bone after the bone has been registered with the computer assisted orthopaedic surgery (CAOS) system.

According to yet a further aspect, an apparatus for registering a bone of a patient with a CAOS system may include a support frame, a first magnetic sensor array coupled to the support frame, and a second magnetic sensor array coupled to the support frame. In some embodiments, the apparatus may include more or less magnetic sensor arrays. Each of the magnetic sensor arrays are movable with respect to the support frame. For example, each magnetic sensor array may be pivoted and/or translated with respect to the frame. Each magnetic sensor array includes a circuit configured to sense a magnetic field of a magnetic source and determine position data indicative a position of the magnetic source. The circuit may include, for example, one or more magnetic sensors and a processing circuit. The circuit may further include an angle sensor configured to determine an angle defined between the magnetic sensor array and a predefined axis. The circuit may additionally include a distance sensor for determining a distance of translation of the magnetic sensor array with respect to a predefined reference point. The circuit may also include a transmitter (e.g., a wireless transmitter) for transmitting the relative position, the determined angle, and the determined distance to a controller such as a computer of a CAOS system. The circuit may further include an indicator, such as a visual indicator, for informing a user of the apparatus that the magnetic sensor array is in a magnetic field of a magnetic source.

According to yet another aspect, a method for registering a bony anatomy of a patient with a CAOS system may include positioning a first magnetic sensor array in a magnetic field of a first magnetic source coupled with the bony anatomy of the patient and positioning a second magnetic sensor array in a magnetic field of a second magnetic source coupled with the bony anatomy. Each of the magnetic sources may be embodied as one or more magnets. The magnetic sensor arrays may be positioned by pivoting the arrays about a common axis and/or moving the arrays along respective longitudinal axes. The method may also include determining first position data indicative of the position of the first magnetic source relative to the first magnetic sensor array and second position data indicative of the position of the second magnetic source relative to the second magnetic sensor array. Determining position data may include determining any one or more of the scalar components of the three-dimensional magnetic flux density and/or determining the six degrees of freedom of the magnetic sources.

The method may also include determining position data indicative of the position of a support frame coupled with the first and second magnetic sensor arrays. The method may further include determining a first distance of translational of the first magnetic sensor array with respect to a reference point and a second distance of translational of the second magnetic sensor array with respect to the reference point. Additionally, the method may include determining a first angle between the first magnetic sensor array and a reference axis and a second angle between the second magnetic sensor array and the reference axis. The method may yet further include transmitting the first and second position data, the first and second distances, and the first and second angles to a controller. Yet further, the method may include coupling the magnetic sources to the bony anatomy of the patient. Additionally, the method may include retrieving an image of the bony anatomy from an electronic file and creating a graphically rendered image of the bony anatomy based on the image data, the position data, the determined distance, and the determined angle.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which:

FIG. 21 is a side elevation view of another embodiment of the magnetic sensor array of FIG. 18;

FIG. 22 is a side elevation view of yet another embodiment of the magnetic sensor array of FIG. 18;

DETAILED DESCRIPTION OF THE DRAWINGS

Figure 1:
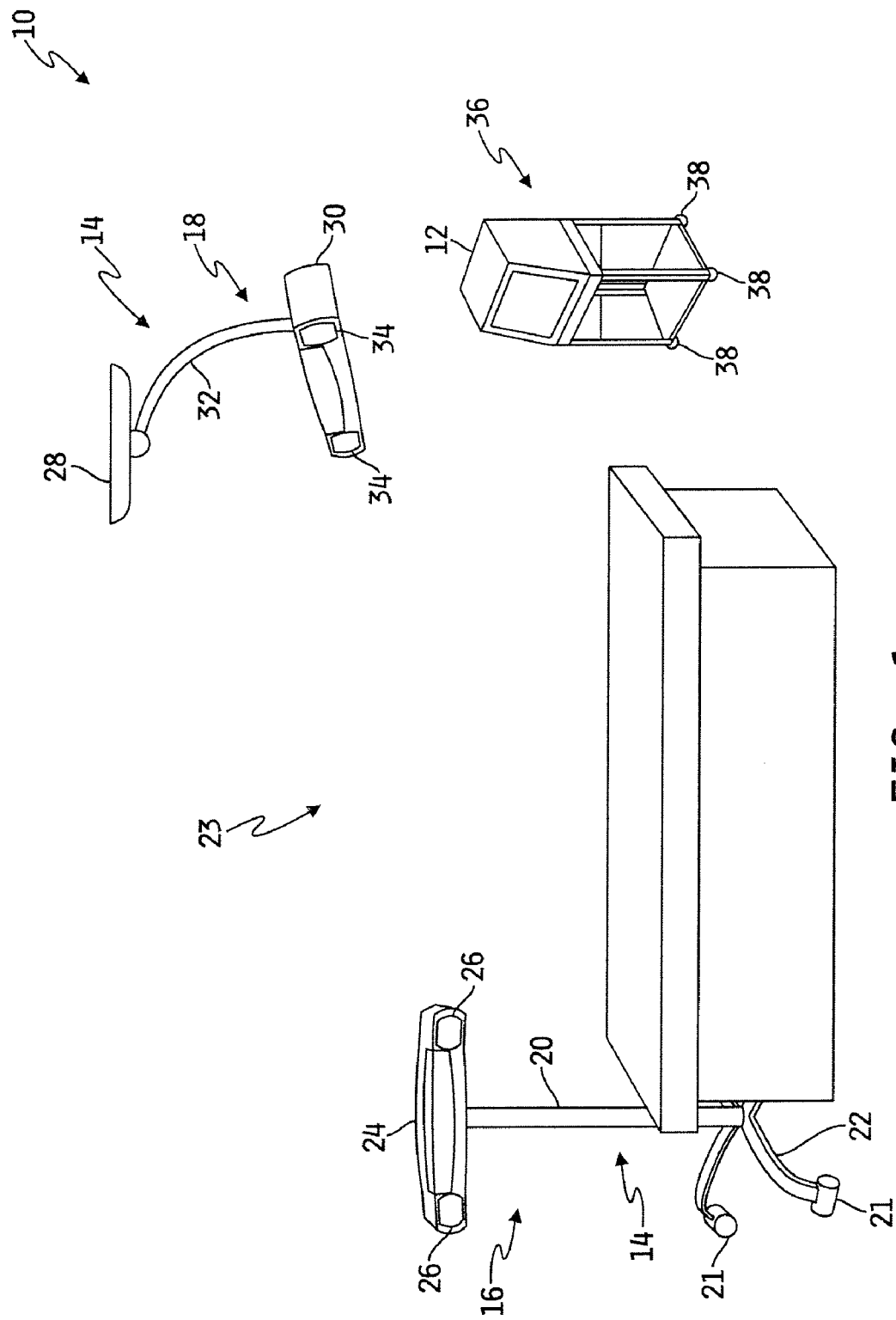
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as a Ci™ system commercially available from DePuy Orthopaedics, Inc. of Warsaw, Ind. The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 21 to allow the mobile camera unit 16 to be repositioned within a hospital room 23. The mobile camera unit 16 includes a camera head 24. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 30, and an arm 32 coupling the camera head 30 with the base 28. In some embodiments, other peripherals, such as display screens, lights, and the like, may also be coupled with the base 28. The camera head 30 includes two cameras 34. The fixed camera unit 18 may be coupled to a ceiling, as illustratively shown in FIG. 1, or a wall of the hospital room. Similar to the camera head 24 of the camera unit 16, the camera head 30 may be positionable relative to the arm 32 such that the field of view of the cameras 34 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
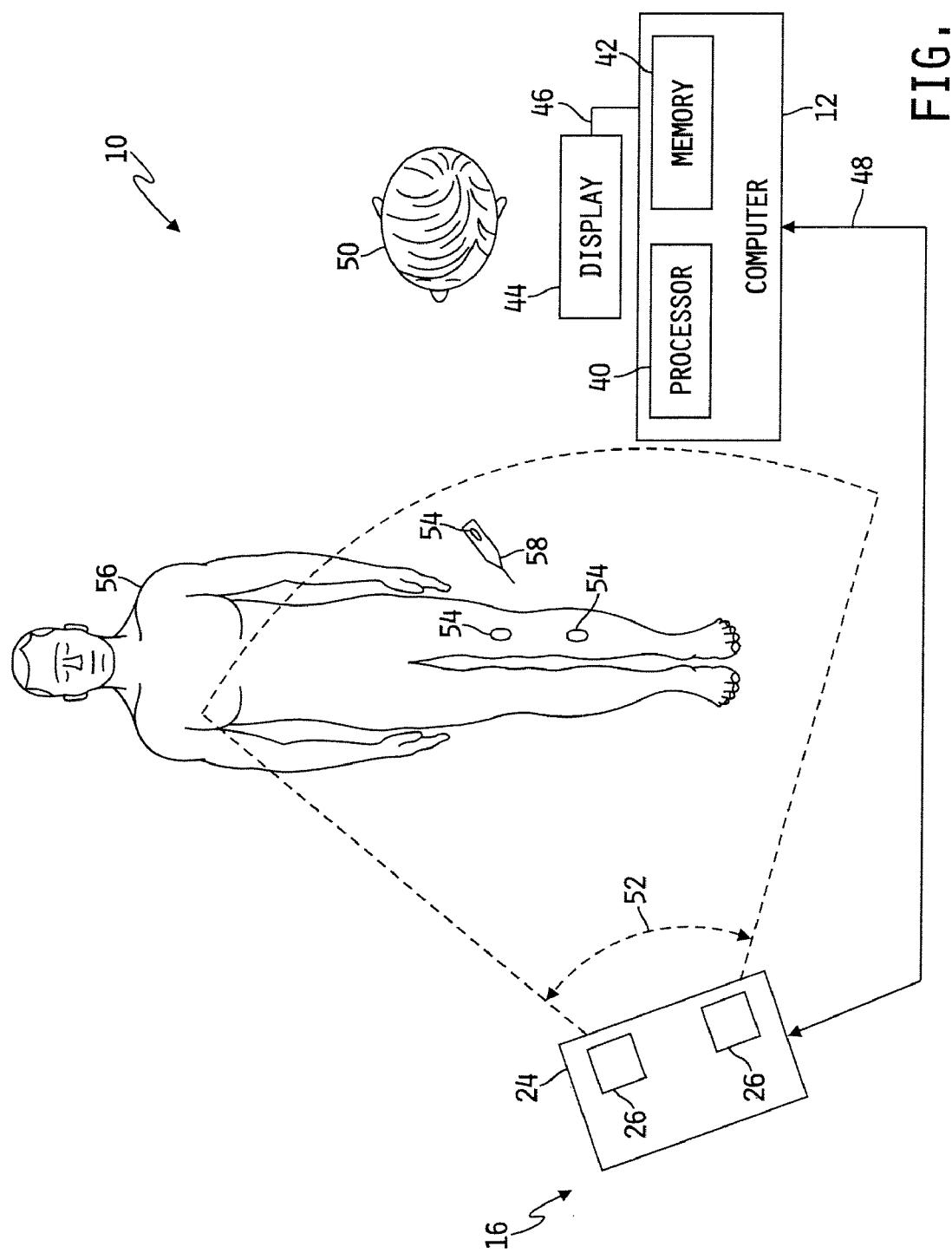
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
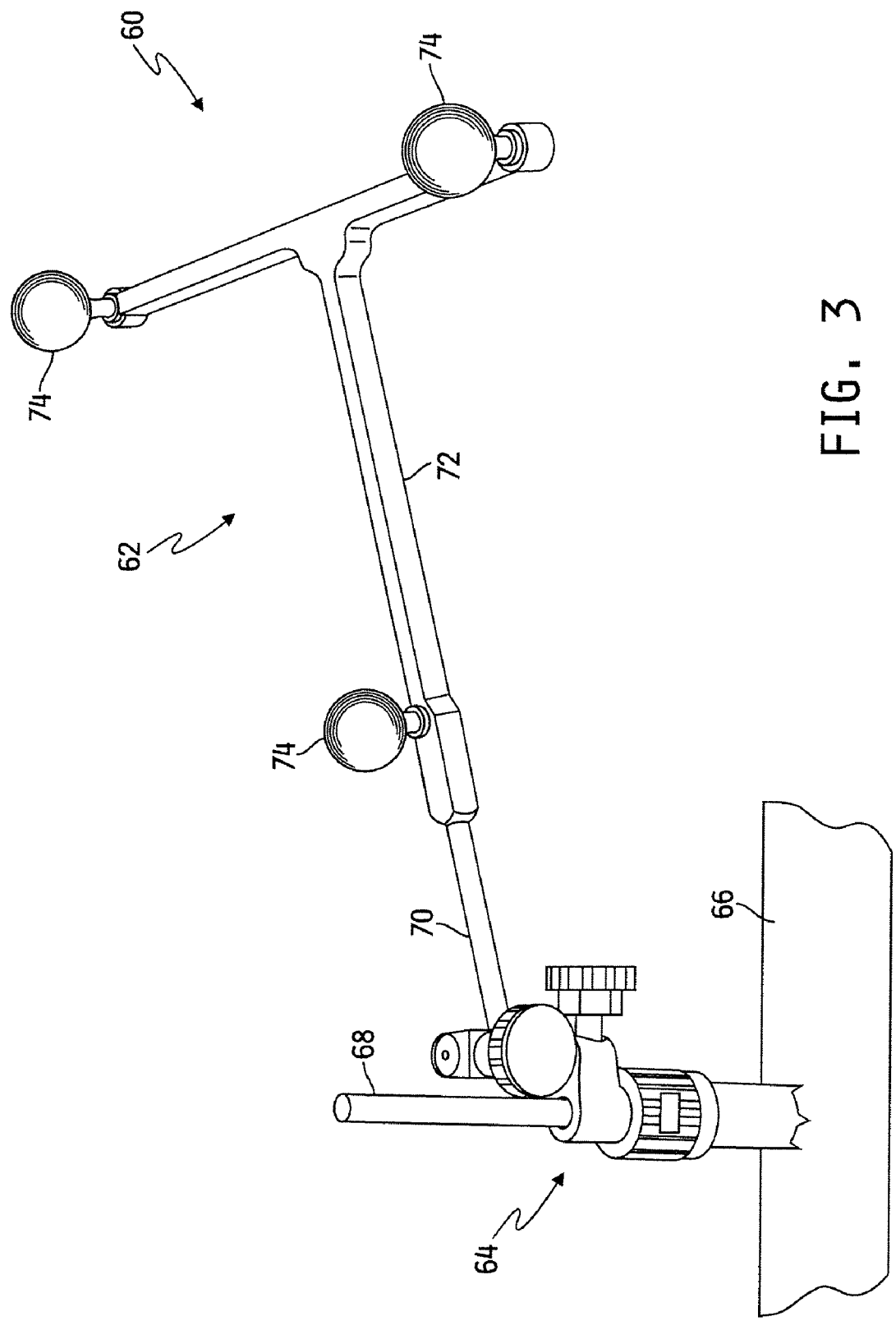
FIG. 3 is a perspective view of a bone locator tool.

The CAOS system 10 may also include a number of sensors or sensor arrays 54 which may be coupled the relevant bones of a patient 56 and/or with orthopaedic surgical tools 58. For example, as illustrated in FIG. 3, a tibial array 60 includes a sensor array 62 and bone clamp 64. The illustrative bone clamp 64 is configured to be coupled with a tibia bone 66 of the patient 56 using a Schantz pin 68, but other types of bone clamps may be used. The sensor array 62 is coupled with the bone clamp 64 via an extension arm 70. The sensor array 62 includes a frame 72 and three reflective elements or sensors 74. The reflective elements 74 are embodied as spheres in the illustrative embodiment, but may have other geometric shapes in other embodiments. Additionally, in other embodiments sensor arrays having more than three reflective elements may be used. The reflective elements 74 are positioned in a predefined configuration that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
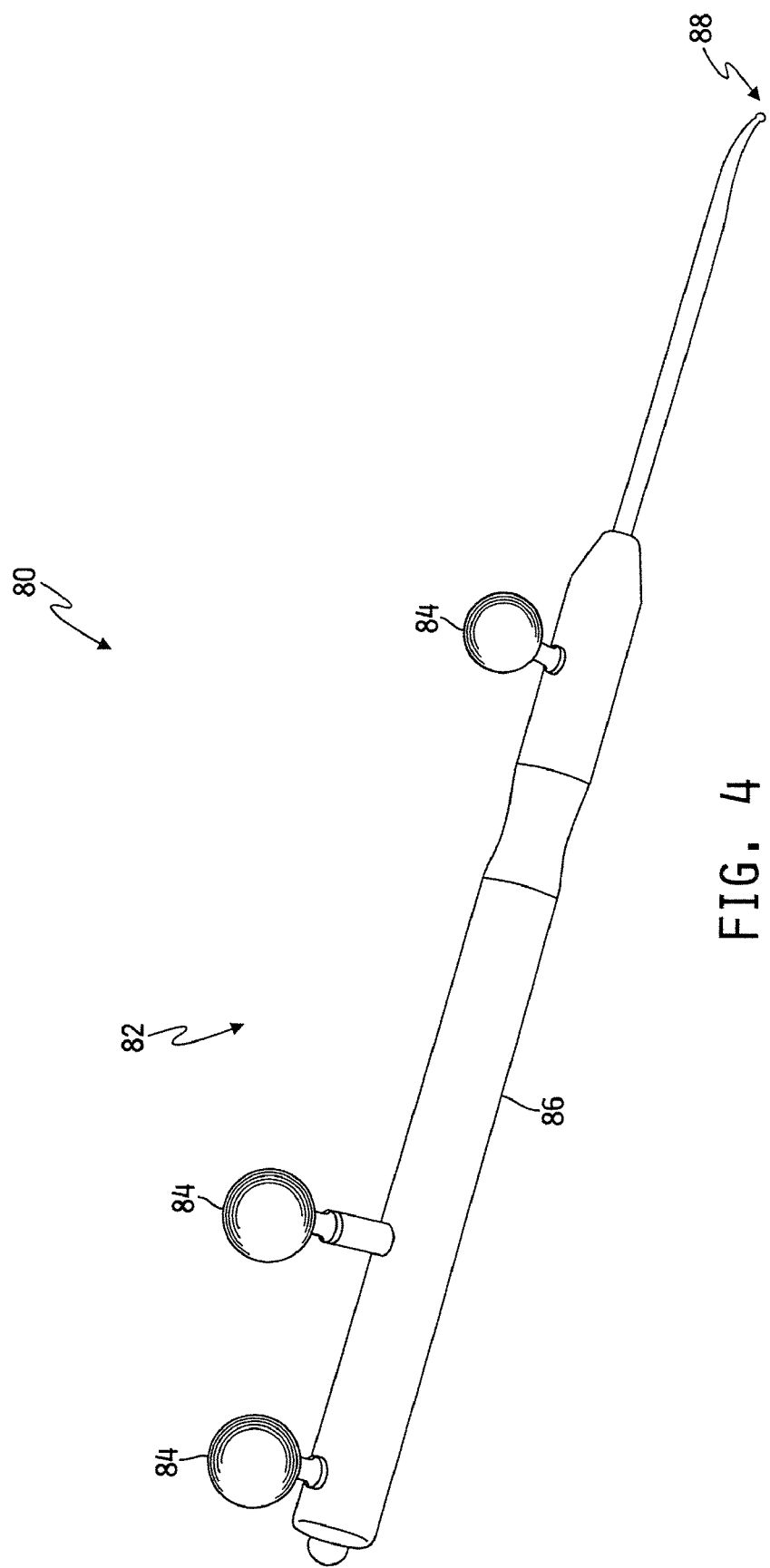
FIG. 4 is a perspective view of a registration tool for use with the system of FIG. 1.
Figure 5:
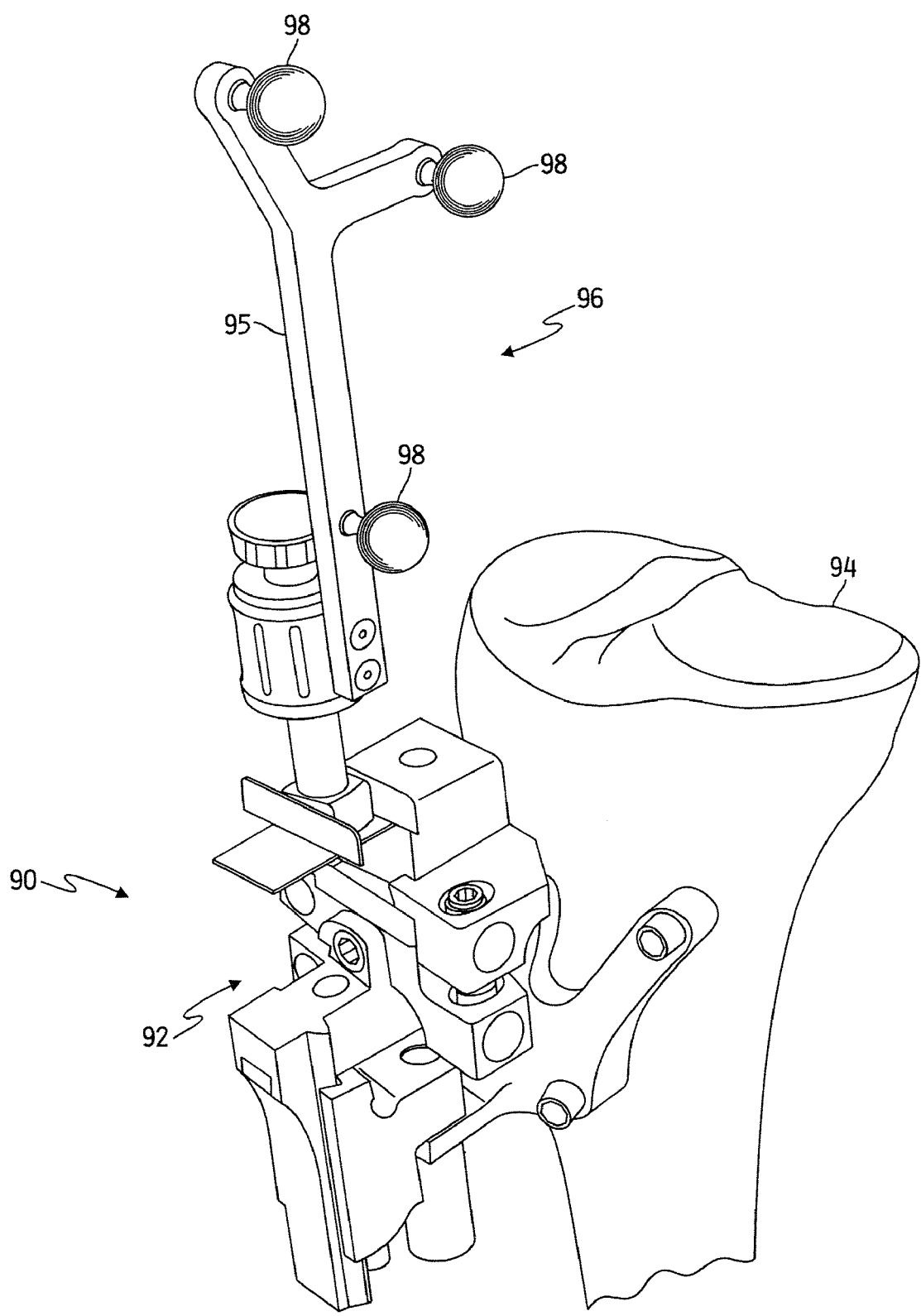
FIG. 5 is a perspective view of an orthopaedic surgical tool for use with the system of FIG. 1.
Figure 7:
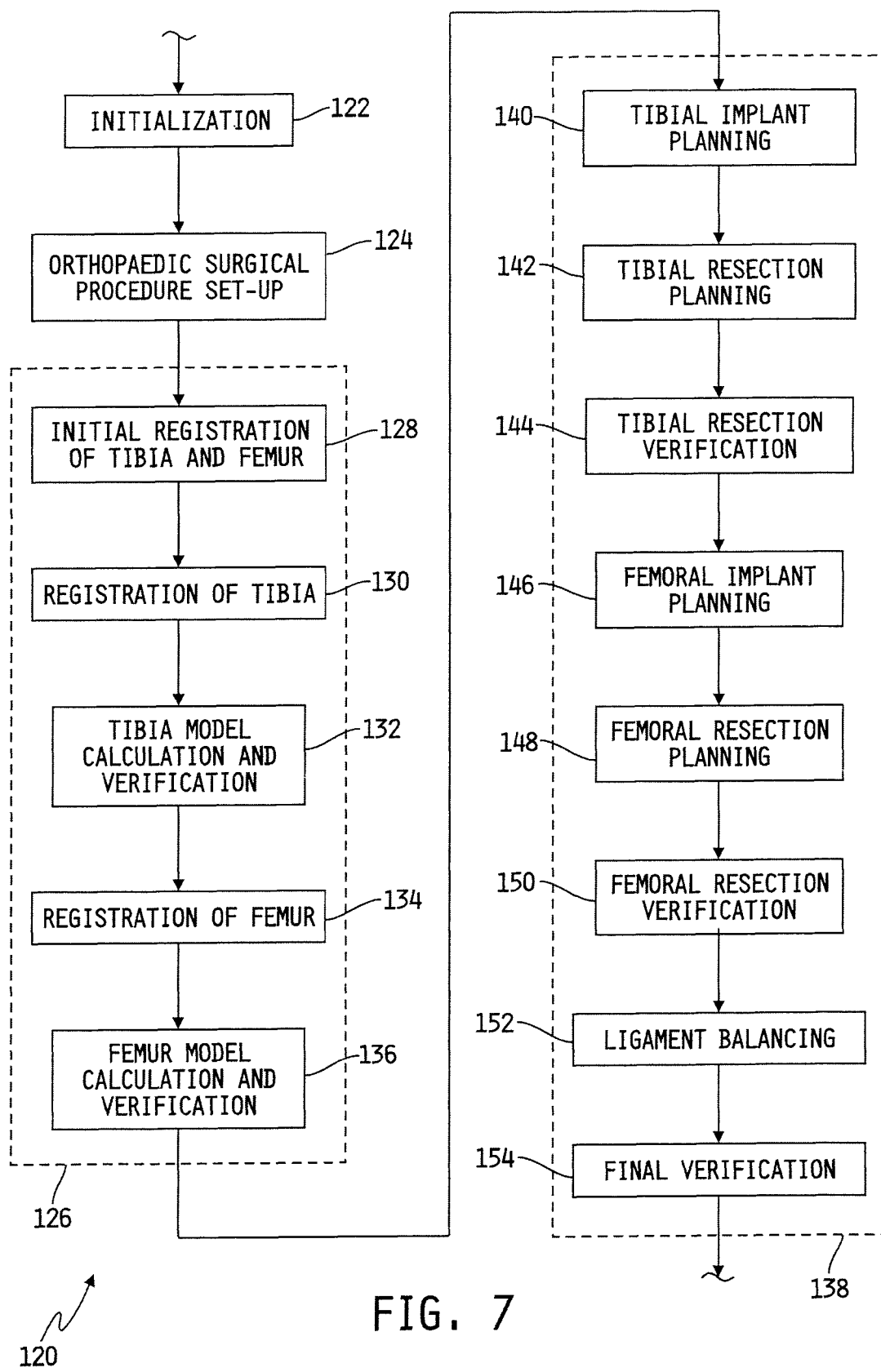
FIG. 7 is a simplified flowchart diagram of one particular embodiment of the algorithm of FIG. 6.

Sensor arrays may also be coupled to other surgical tools. For example, a registration tool 80, as shown in FIG. 4, is used to register points of a bone as discussed in more detail below in regard to FIG. 7. The registration tool 80 includes a sensor array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, sensor arrays may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a sensor array 96 that is coupled with the portion 92 via a frame 95. The sensor array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 56 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon 50 may interact with the computer 12 to display the images of the various surgical steps in sequential order. In addition, the surgeon may interact with the computer 12 to view previously displayed images of surgical steps, selectively view images, instruct the computer 12 to render the anatomical result of a proposed surgical step or procedure, or perform other surgical related functions. For example, the surgeon may view rendered images of the resulting bone structure of different bone resection procedures. In this way, the CAOS system 10 provides a surgical "walk-through" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon to inquire if the surgeon has completed the current surgical step, if the surgeon would like to view other images, and the like.

The camera unit 16 and the computer 12 also cooperate to provide the surgeon with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the sensor arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Figure 6:
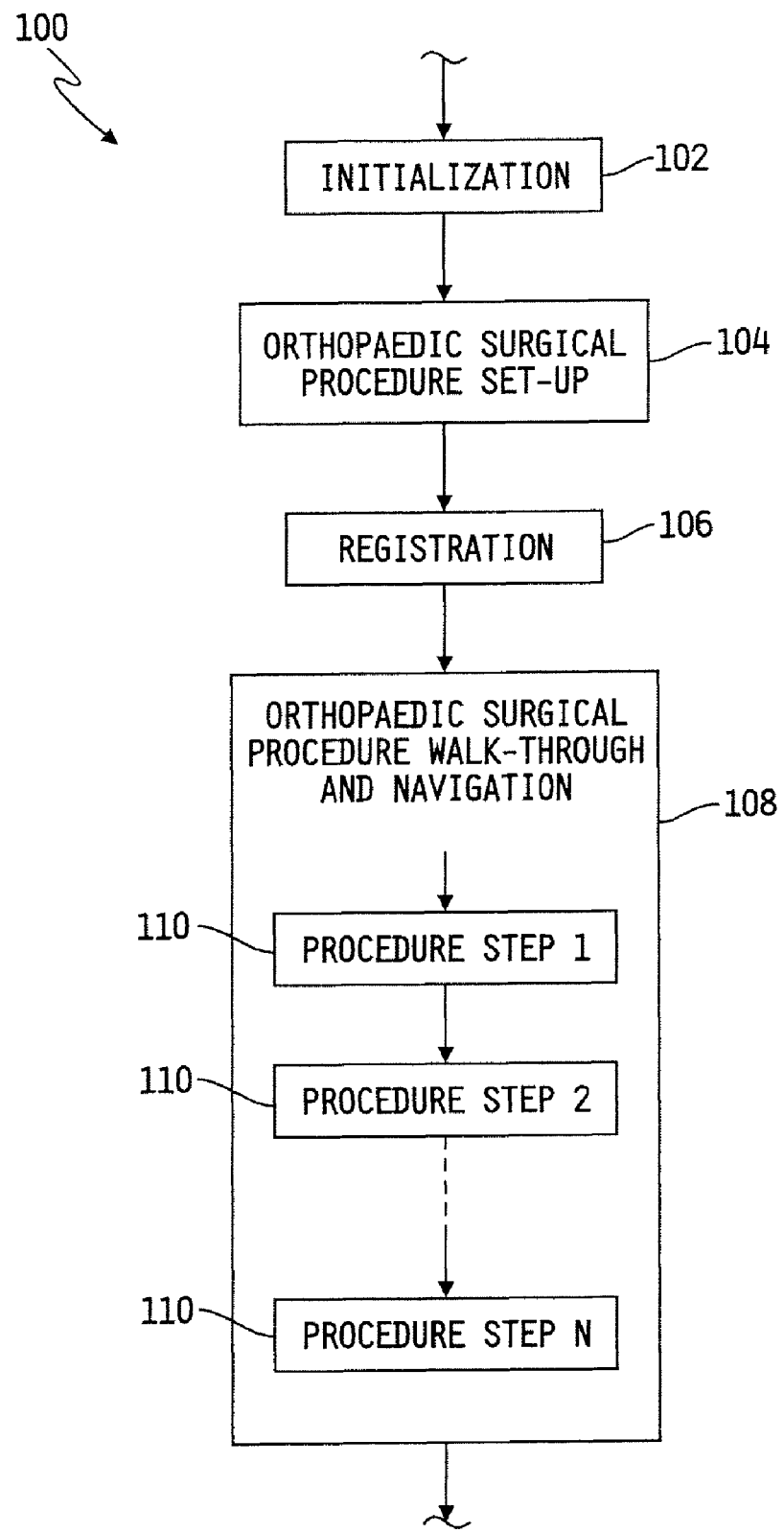
FIG. 6 is a simplified flowchart diagram of an algorithm that is used by the CAOS system of FIG. 1.

Referring now to FIG. 6, an algorithm 100 for assisting a surgeon in performing an orthopaedic surgical procedure is executed by the computer 12. The algorithm 100 begins with a process step 102 in which the CAOS system 10 is initialized. During process step 102, settings, preferences, and calibrations of the CAOS system 10 are established and performed. For example, the video settings of the display device 44 may be selected, the language displayed by the computer 12 may be chosen, and the touch screen of the display device 44 may be calibrated in process step 102.

In process step 104, the selections and preferences of the orthopaedic surgical procedure are chosen by the surgeon. Such selections may include the type of orthopaedic surgical procedure that is to be performed (e.g., a total knee arthroplasty), the type of orthopaedic implant that will be used (e.g., make, model, size, fixation type, etc.), the sequence of operation (e.g., the tibia or the femur first), and the like. Once the orthopaedic surgical procedure has been set up in process step 104, the bones of the patient are registered in process step 106. To do so, sensor arrays, such as the tibial array 60 illustrated in FIG. 3, are coupled with the relevant bones of the patient (i.e., the bones involved in the orthopaedic surgical procedure). Additionally, the contours of such bones are registered using the registration tool 80. To do so, the pointer end 88 of the tool 80 is touched to various areas of the bones to be registered. In response to the registration, the computer 12 displays rendered images of the bones wherein the location and orientation of the bones are determined based on the sensor arrays coupled therewith and the contours of the bones are determined based on the registered points. Because only a selection of the points of the bone is registered, the computer 12 calculates and renders the remaining areas of the bones that are not registered with the tool 80.

Figure 8:
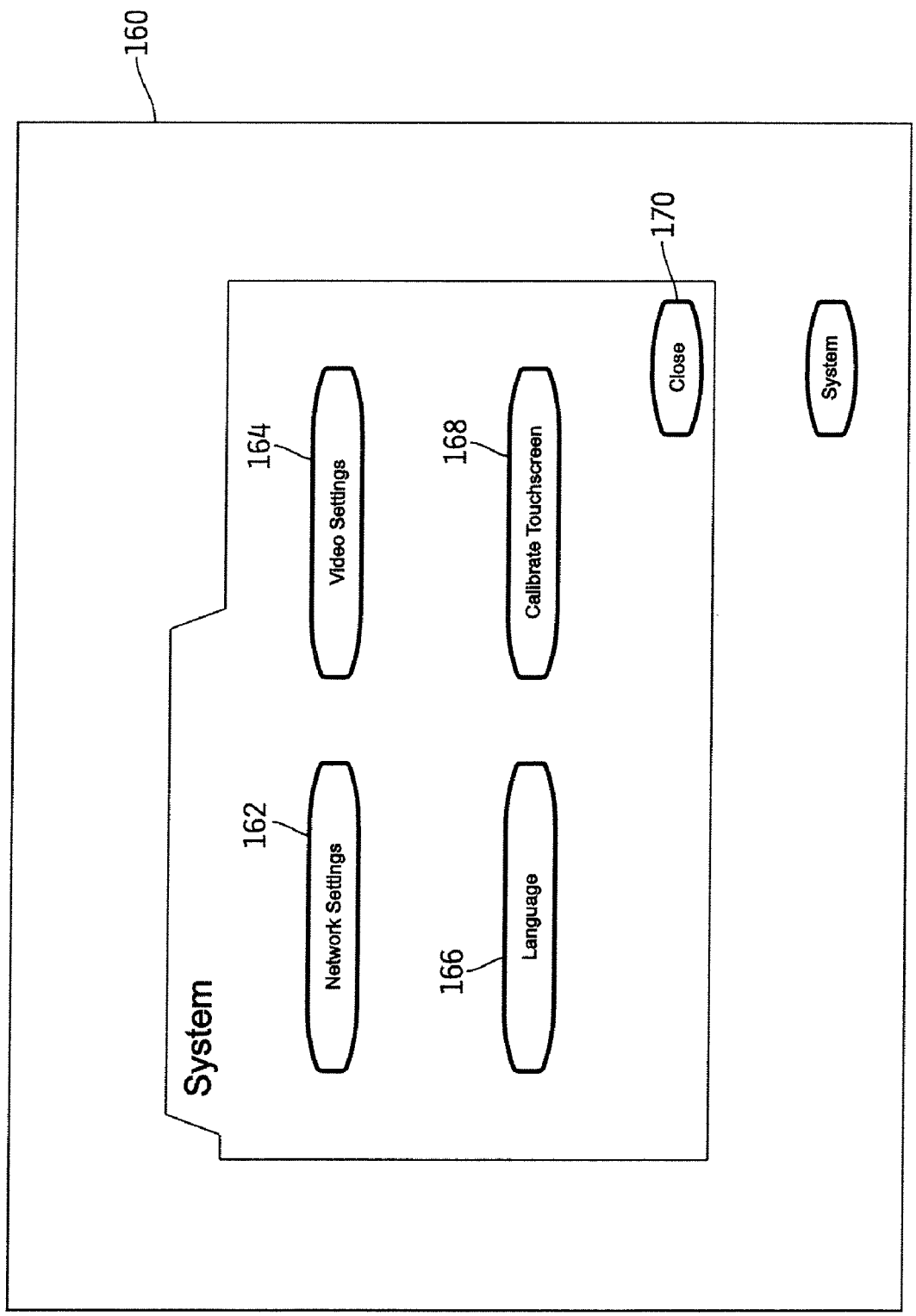
FIGS. 8-17 illustrate various screen images that are displayed to a surgeon during the operation of the system of FIG. 1

Once the pertinent bones have been registered in process step 106, the computer 12, in cooperation with the camera unit 16, 18, displays the images of the surgical steps of the orthopaedic surgical procedure and associated navigation data (e.g., location of surgical tools) in process step 108. To do so, the process step 108 includes a number of sub-steps 110 in which each surgical procedure step is displayed to the surgeon 50 in sequential order along with the associated navigational data. The particular sub-steps 110 that are displayed to the surgeon 50 may depend on the selections made by the surgeon 50 in the process step 104. For example, if the surgeon 50 opted to perform a particular procedure tibia-first, the sub-steps 110 are presented to the surgeon 50 in a tibia-first order Referring now to FIG. 7, in one particular embodiment, an algorithm 120 for assisting a surgeon in performing a total knee arthroplasty procedure may be executed by the computer 12. The algorithm 120 includes a process step 122 in which the CAOS system 10 is initialized. The process step 122 is similar to the process step 102 of the algorithm 100 described above in regard to FIG. 6. In process step 122, the preferences of the CAOS system 10 are selected and calibrations are set. To do so, the computer 12 displays a user initialization interface 160 to the surgeon 50 via the display device 44 as illustrated in FIG. 8. The surgeon 50 may interact with the interface 160 to select various initialization options of the CAOS system 10. For example, the surgeon 50 may select a network settings button 162 to change the network settings of the system 10, a video settings button 164 to change the video settings of the system 10, a language button 166 to change the language used by the system 10, and/or a calibration button 168 to change the calibrations of the touch screen of the display device 44. The surgeon 50 may select a button by, for example, touching an appropriate area of the touch screen of the display device 44, operating an input device such as a mouse to select the desired on-screen button, or the like.

Additional images and/or screen displays may be displayed to the surgeon 50 during the initialization process. For example, if the surgeon 50 selects the button 162, a network setting interface may be displayed on the device 44 to allow the surgeon 50 to select different values, connections, or other options to change the network settings. Once the CAOS system 10 has been initialized, the surgeon 50 may close the user initialization interface 160 by selecting a close button 170 and the algorithm 120 advances to the process step 124.

Figure 9:
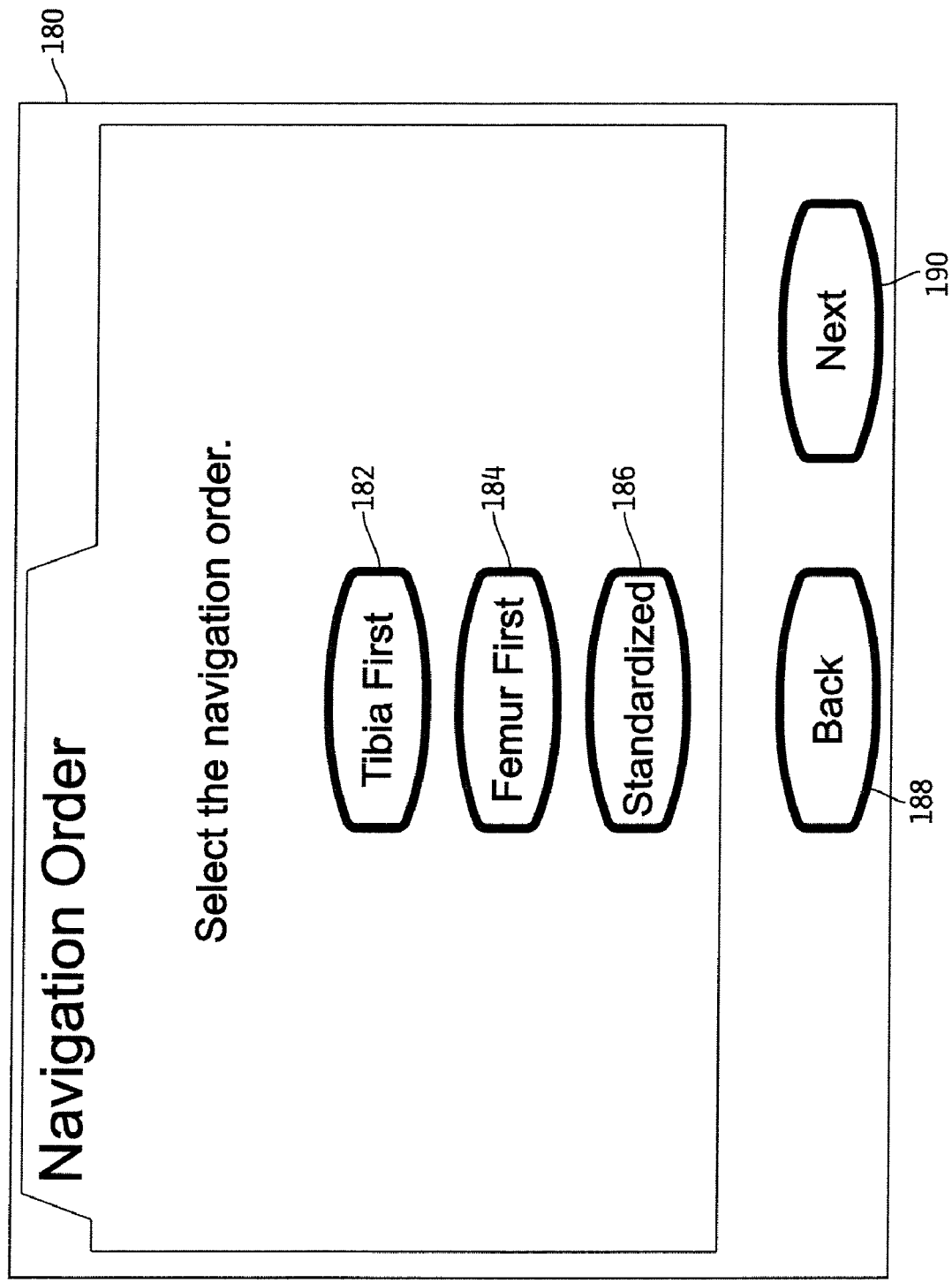

In process step 124, selections of the orthopaedic surgical procedure are chosen by the surgeon 50. The process step 124 is similar to the process step 104 of the algorithm 100 described above in regard to FIG. 6. For example, the selections made in the process step 104 may include, but are not limited to, the type of orthopaedic surgical procedure that is to be performed, the type of orthopaedic implant that will be used, and the sequence of operation, and the like. To do so, a number of procedure preference selection screens may be displayed to the surgeon 50 via the display device 44. For example, as illustrated in FIG. 9, a navigation order selection screen 180 may be displayed to the surgeon 50. The surgeon 50 may interact with the screen 180 to select the navigational (i.e., surgical) order of the orthopaedic surgical procedure being performed (i.e., a total knee arthroplasty procedure in the illustrative embodiment). For example, the surgeon 50 may select a button 182 to instruct the controller 12 that the tibia bone of the patient 56 will be operated on first, a button 184 to instruct the controller 12 that the femur bone will be operated on first, or a button 186 to select a standardized navigation order based on, for example, the type of orthopaedic implant being used. The surgeon 50 may also navigate among the selection screens by a back button 188 to review previously displayed orthopaedic surgical procedure set-up screens or a next button 190 to proceed to the next orthopaedic surgical procedure set-up screen. Once the surgeon 50 has selected the appropriate navigation order and/or other preferences and settings of the orthopaedic surgical procedure being performed, the algorithm 120 advances to the process step 126.

In the process step 126, the relevant bones of the patient 56 are registered. The process step 126 is similar to the registration process step 106 of the algorithm 100. The process step 126 includes a number of sub-steps 128-136 in which the bones of the patient 56 involved in the orthopaedic surgical procedure are registered. In process step 128, the relevant bones are initially registered. That is, in the illustrative algorithm 120, a tibia and a femur bone of the patient 56 are initially registered. To do so, a tibia array, such as the tibia array 60 illustrated in and described above in regard to FIG. 3, and a femur array are coupled with the respective bones. The tibia and femur arrays are coupled in the manner described above in regard to the tibia array 60. The camera head 24 of the camera unit 16 is adjusted such that the tibia and femur arrays are within the field of view 52 of the camera head 24. Once the arrays are coupled and the camera head 24 properly positioned, the tibia and femur of the patient 56 are initially registered.

Figure 10:
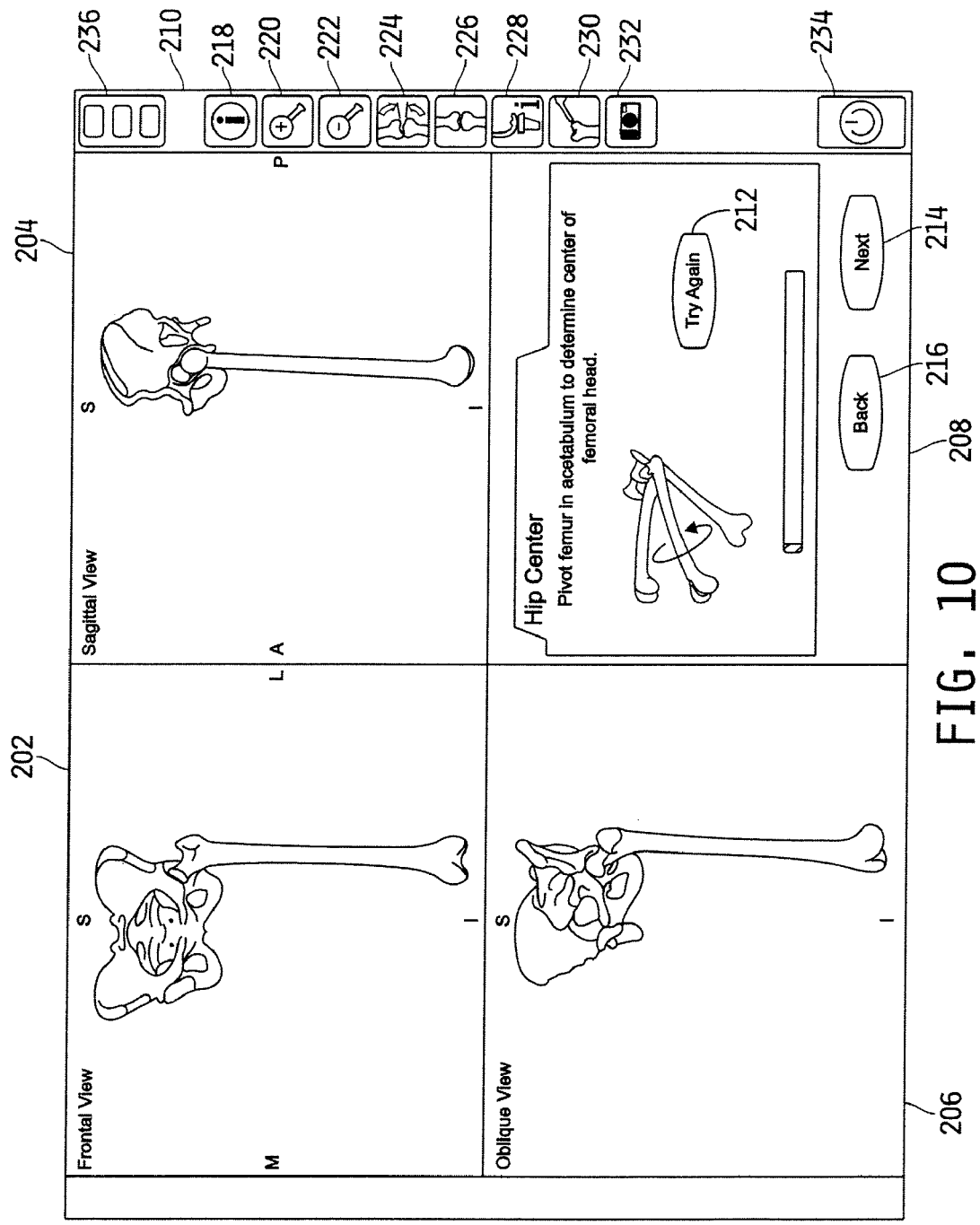

To do so, the controller 12 displays a user interface 200 to the surgeon 50 via the display device 44, as shown in FIG. 10. The interface 200 includes several navigation panes 202, 204, 206, a surgical step pane 208, and a tool bar 210. Navigational data is displayed to the surgeon 50 in the navigation panes 202, 204, 206. The computer 12 displays different views of the bone and/or surgical tools 58 in each of the panes 202, 204, 206. For example, a frontal view of the patient's 56 hip and femur bone is displayed in the navigation pane 202, a sagittal view of the patient's 56 bones is displayed in the navigation pane 204, and an oblique view of the patient's 56 bones is displayed in the navigation pane 206.

The computer 12 displays the surgical procedure steps in the pane 208. For example, in FIG. 10, the computer 12 is requesting the leg of the patient 56 be moved about in a circular motion such that the femur bone of the patient 56 is initially registered. In response, the computer 12 determines the base location and orientation of the femur bone (e.g., the femur head) of the patient 56 based on the motion of the sensor array 54 coupled with the bone (i.e., based on the image data of the sensor array 54 received from the camera head 24). Although only the femur bone is illustrated in FIG. 10 as being initially registered, it should be appreciated that the tibia bone is also initially registered and that other images and display screen are displayed to the surgeon 50 during such initial registration.

The surgeon 50 can attempt to initially register the bones as many times as required by selecting a "try again" button 212. Once the relevant bones have been initially registered, the surgeon 50 can advance to the next surgical procedure step of the registration step 126 by selecting the next button 214. Alternatively, the surgeon 50 can skip one or more of the initial registration steps by selecting the button 214 and advancing to the next surgical procedure step while not performing the initial registration step (e.g., by not initially registering the femur bone of the patient 56). The surgeon 50 may also go back to the previous surgical procedure step (e.g., the initial registration of the tibia) by selecting a back button 216. In this way, the surgeon 50 can navigate through the surgical setup, registration, and procedure steps via the buttons 214, 216.

The toolbar 210 includes a number of individual buttons, which may be selected by the surgeon 50 during the performance of the orthopaedic surgical procedure. For example, the toolbar 210 includes an information button 218 that may be selected to retrieve and display information on the application software program being executed by the computer 12 such as the version number, "hotline" phone numbers, and website links. The toolbar 210 also includes zoom buttons 220 and 222. The zoom button 220 may be selected by the surgeon 50 to zoom in on the rendered images displayed in the panes 202, 204, 206 and the zoom button 222 may be used to zoom out. A ligament balancing button 224 may be selected to proceed to a ligament balancing procedure, which is described in more detail below in regard to process step 152. A 3D model button 226 may be selected to alternate between the displaying of the rendered bone (e.g., femur or tibia) and displaying only the registered points of the rendered bone in the navigation panes 202, 204, and 206. An implant information button 228 may be selected to display information related to an orthopaedic implant selected during later steps of the orthopaedic surgical procedure (e.g., process steps 140 and 146 described below). Such information may include, for example, the make, type, and size of the orthopaedic implant. A registration verification button 230 may be selected by the surgeon 50 at any time during the procedure to verify the rendered graphical model of a bone if, for example, the sensor arrays 54 coupled with the bone are accidentally bumped or otherwise moved from their fixed position. A screenshot button 232 may also be selected by the surgeon 50 at any time during the performance of the orthopaedic surgical procedure to record and store a screenshot of the images displayed to the surgeon 50 at that time. The screenshots 50 may be recorded in a storage device, such as a hard drive, of the computer 12. A close button 234 may be selected to end the current navigation and surgical procedure walk-through. After selecting the button 234, any information related to the orthopaedic surgical procedure that has been recorded, such as screenshots and other data, are stored in the storage device of the computer 12 for later retrieval and review.

The toolbar 210 also includes a status display 236. The status display 236 displays different color lights that indicate whether the system 10 can "see" or otherwise detect the sensor arrays 54 coupled with the bones and/or surgical tools. The status display 236 is also a button that may be selected to view a help screen illustrating a graphical rendering of the field of view 52 of the camera head 24 such that the positioning of the camera unit 16 and the sensor arrays 54 and surgical tools 58 can be monitored and adjusted if needed.

Figure 11:
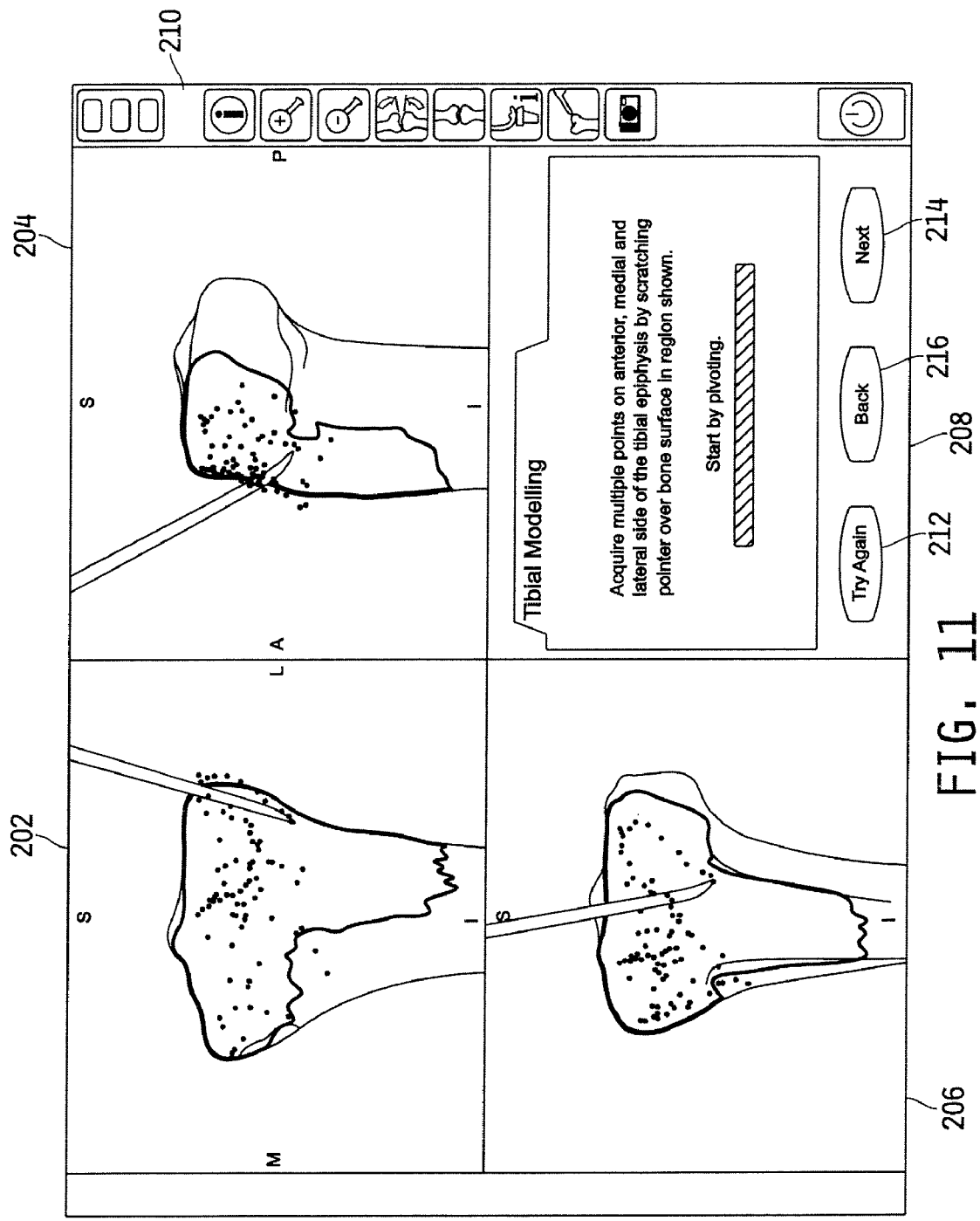

Once the initial registration of the tibia and femur bones of the patient 56 is complete, the algorithm 120 advances to process step 130 in which the contour of the proximal tibia of the patient 56 is registered. To do so, the surgeon 50 uses a registration tool, such as the registration tool 80 illustrated in and described above in regard to FIG. 4. As illustrated in FIG. 11, the surgeon 50 registers the proximal tibia by placing the pointer end 88 of the registration tool 80 on the surface of the tibia bone as instructed in the surgical step pane 208. Contour points of the tibia bone are recorded by the computer 12 periodically as the pointer end 88 is dragged across the surface of the tibia bone and/or placed in contact with the tibia bone. The surgeon 50 registers enough points on the proximal tibia such that the computer 12 can determine and display a relatively accurate rendered model of the relevant portions of the tibia bone. Portions of the tibia bone that are not registered, but rather rendered by the computer 12 based on a predetermined model of the tibia bone, are displayed to the surgeon 50 in a different color than the registered portions of the tibia bone. In this way, the surgeon 50 can monitor the registration of the tibia bone and ensure that all relevant portions of the tibia bone have been registered to improve the accuracy of the displayed model.

Figure 12:
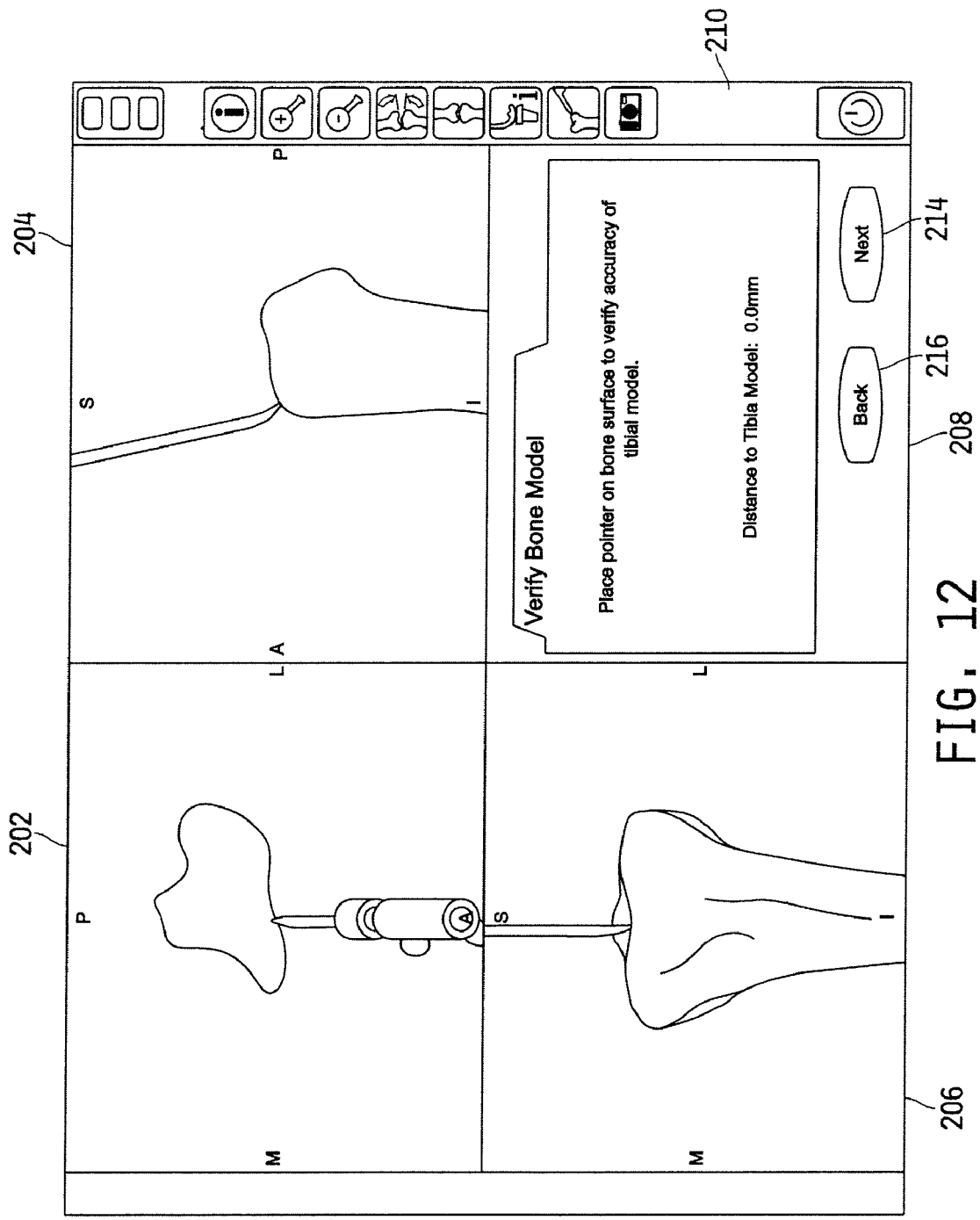

Once all the relevant portions of the proximal tibia have been registered in process step 130, the tibia model is calculated and verified in process step 132. To do so, the surgeon 50 follows the instructions provided in the surgical step pane 208. The proximal tibia is verified by touching the pointer end 88 of the registration tool 80 to the registered portions of the tibia bone and monitoring the distance data displayed in the pane 208 as illustrated in FIG. 12. Based on the distance data, the surgeon 50 can determine if the current tibia model is accurate enough for the orthopaedic surgical procedure. If not, the surgeon 50 can redo the registration of the proximal tibia or supplement the registration data with additional registration points by selecting the back button 216. Once the model of the patient's 56 tibia has been determined to be sufficiently accurate, the surgeon 50 may proceed by selecting the next button 214.

The distal femur of the patient 56 is registered next in the process step 134. The registration of the femur in process step 134 is similar to the registration of the tibia in the process step 130. That is, the registration tool 80 is used to registered data points on the distal femur. Once the registration of the femur is complete, the femur model is calculated and verified in process step 136. The verification of the femur in process step 136 is similar to the verification of the tibia in process step 132. The registration tool 80 may be used to touch pre-determined portions of the femur to determine the accuracy of the femur model. Based on the distance data displayed in the surgical step pane 208, the surgeon 50 may reregister the femur or add addition registration data points to the model by selecting the back button 216. Once the femur bone model is verified, the surgeon 50 can proceed with the orthopaedic surgical procedure by selecting the next button 214.

Figure 13:
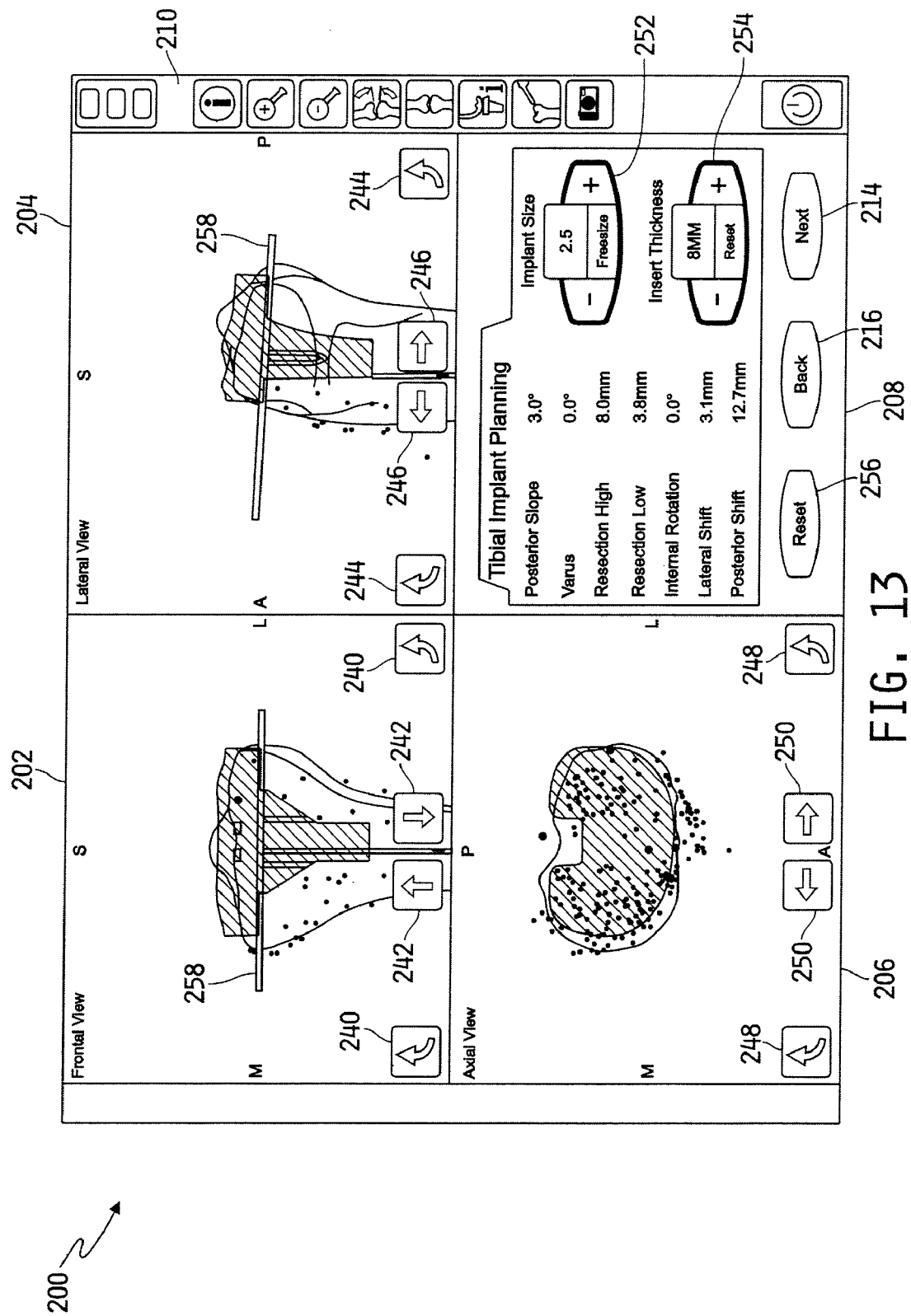

Once the relevant bones (i.e., the proximal tibia and distal femur) have been registered in process step 126, the algorithm 120 advances to process step 138 in which the computer 12 displays images of the individual surgical steps of the orthopaedic surgical procedure and the associated navigation data to the surgeon 50. To do so, the process step 138 includes a number of sub-steps 140-154. In process step 140 the planning for the tibial implant is performed. Typically, the selection of the tibial implant is performed in the process step 124, but may be modified in the process step 140 depending upon how well the selected implant fits with the proximal tibia. As illustrated in FIG. 13, a graphically rendered model of the tibial implant is displayed superimposed over the rendered model of the tibia bone in the navigation panes 202, 204, 206. The positioning of the tibial implant can be adjusted via the selection of a number of implant adjustment buttons. For example, the varus/valgus rotation of the orthopaedic implant may be adjusted via the buttons 240, the superior/inferior or proximal/distal translational of the orthopaedic implant may be adjusted via the buttons 242, the slope of the orthopaedic implant may be adjusted via the buttons 244, the anterior/posterior translational of the orthopaedic implant may be adjust via the buttons 246, the internal/external rotation of the orthopaedic implant may be adjusted by the buttons 248, and the medial/lateral translational of the orthopaedic implant may be adjusted by the buttons 250. Data related to the positioning of the orthopaedic implant is displayed in the surgical step panel 208. Some attributes of the implant, such as the orthopaedic implant size and thickness may be adjusted via the selection of button panels 252 and 254, respectively. Additionally the original location and orientation of the implant may be reset via selection of a reset button 256. Using the various implant adjustment buttons and the implant attribute button panels 252, 254, the surgeon 50 positions and orientates the tibial implant such that a planned resection plane 258 of the tibia bone is determined. Because the surgeon 50 can see a visual rendering of the planned resection plane and the location/orientation of the tibial implant, the surgeon 50 can alter the location and orientation of the resection plane and/or tibial implant until the surgeon 50 is satisfied with the final fitting of the tibial implant to the resected proximal tibia. Once so satisfied, the surgeon 50 may proceed to the next surgical step by selecting the next button select the next button 214.

Figure 14:
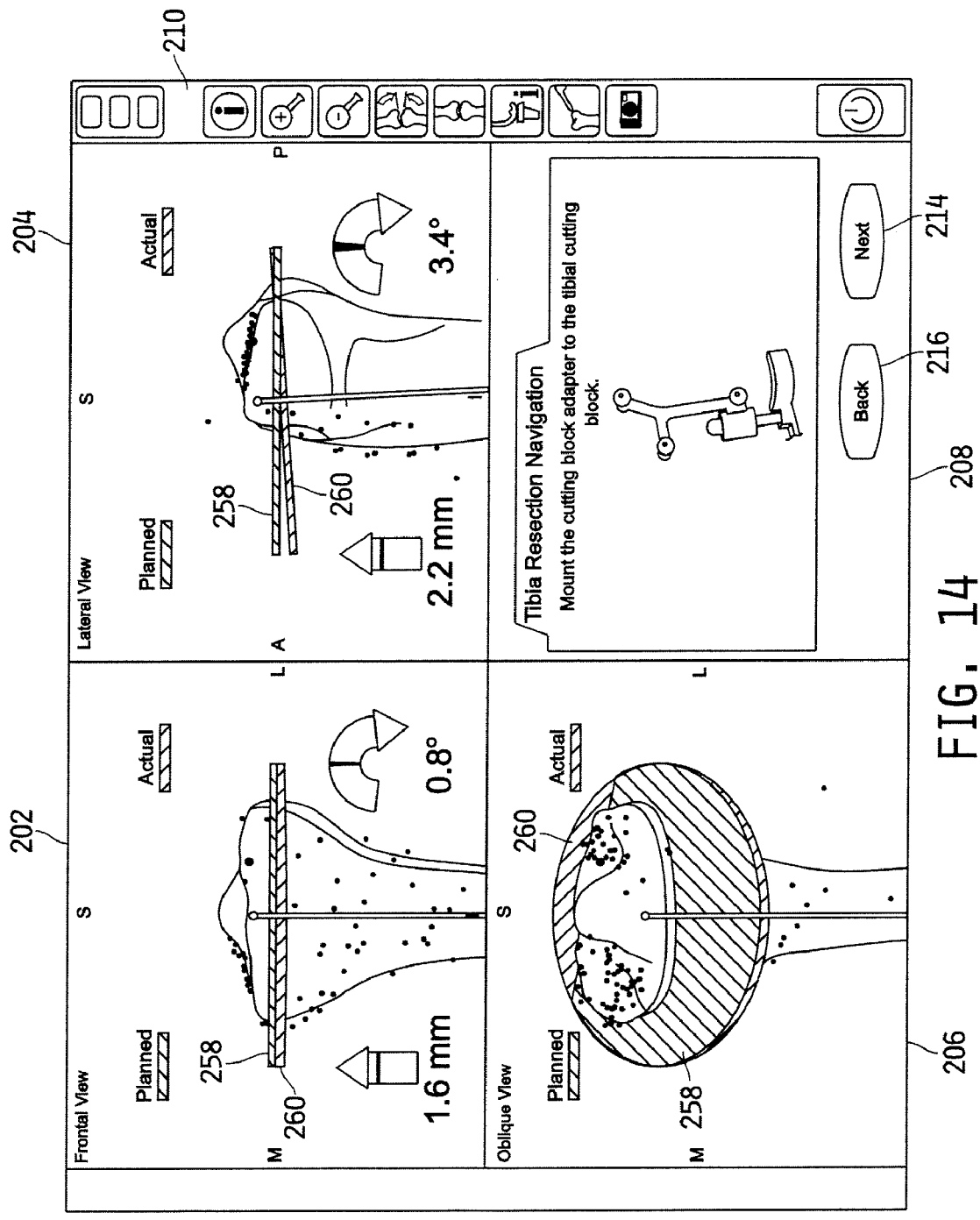

In process step 142 the resectioning of the proximal tibia is planned. To do so, a resection jig, such as the tibial resection jig 90 illustrated in and described above in regard to FIG. 5, is coupled with the tibia bone of the patient 56 near the desired resection location of the proximal tibia. As illustrated in FIG. 14, the computer 12 displays the correct surgical tool to use in the present step in the surgical step pane 208. In response, the computer 12 displays an actual resection plane 260 to the surgeon 50 on the navigation panes 202, 204, 206. As shown, a planned resection plane 258, as determined in step 140, is also displayed. The surgeon 50 may then adjust the coupling of the jig 90 with the tibia bone of the patient 56 such that the actual resection plane 260 overlaps or nearly overlaps the planned resection plane 258. In this way, the surgeon 50 is able to visually monitor the actual resection plane 260 while adjusting the jig 90 such that an accurate resection of the tibia can occur. The surgeon 50 may advance to the next surgical step by selecting the next button 214.

Figure 15:
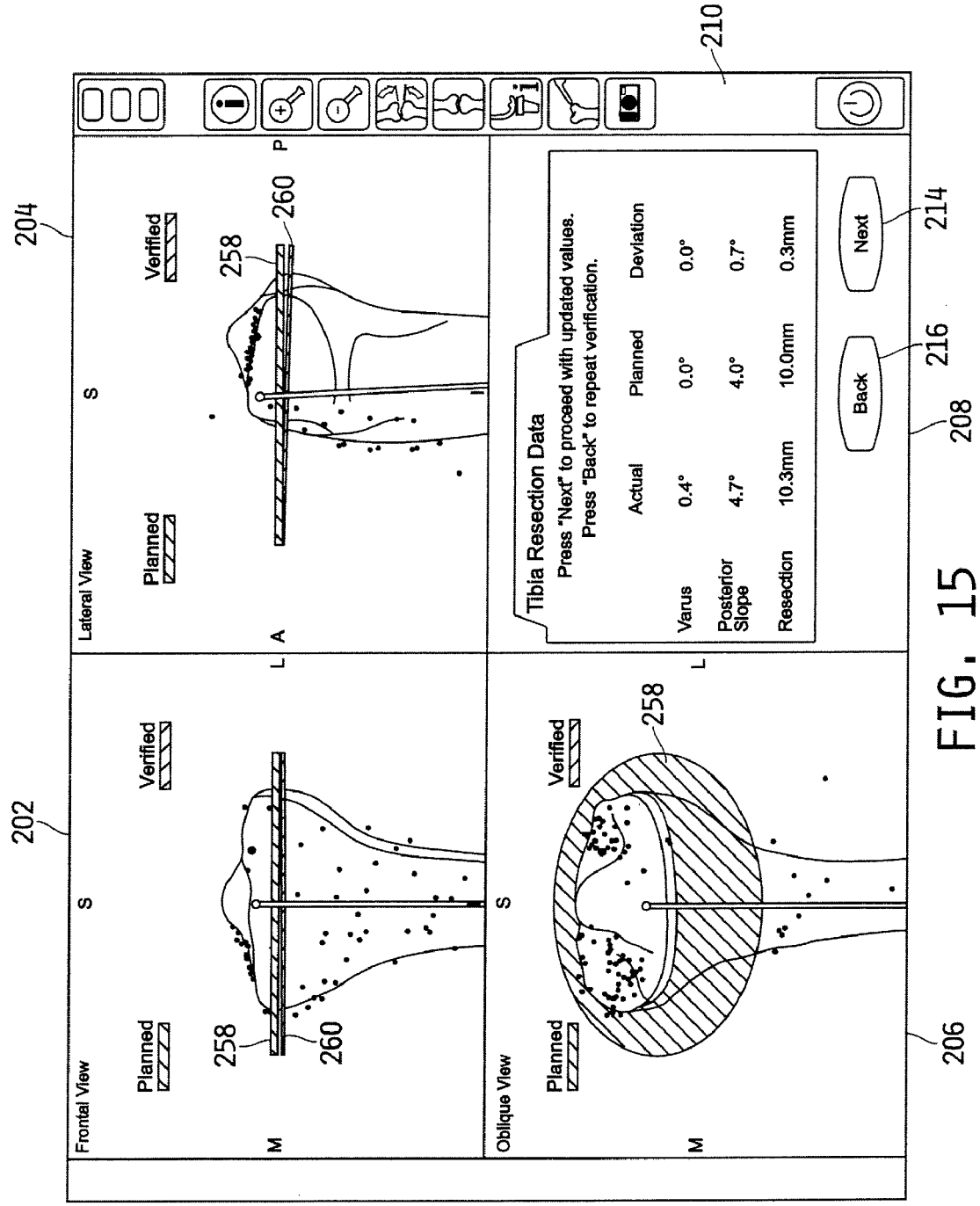

Once the surgeon 50 has reviewed and adjusted the actual resection plane 260 in process step 142, the algorithm 120 advances to process step 144. In process step 144, the tibia is resected using the appropriate resection tool and the jig 90 coupled with the tibia bone of the patient 56. After the proximal tibia has been resected, the computer 12 displays a verified resection plane 260 superimposed with the planned resection plane 258 as illustrated in FIG. 15. The computer 12 also displays data related to the resection of the proximal tibia, including actual, planned, and deviation measurements, in the surgical step panel 208. In this way, the surgeon 50 can compare the final resection of the tibia and the planned resection. If needed, the surgeon 50 can repeat the resectioning process to remove more the proximal tibia. Once the surgeon 50 is satisfied with the resection of the tibia bone, the surgeon 50 may advance to the next surgical step by selecting the next button 214.

Once the tibia bone of the patient 56 has been resected, the relevant distal femur bone is resected in process steps 146-150. In process step 146, the planning for the femoral implant is performed. The femoral implant planning of process step 146 is similar to the tibial implant planning performed in process step 124. During process step 146, the surgeon 50 positions and orients the femoral implant such that a planned resection plane of the distal femur is determined and may also select relevant implant parameters (e.g., size, type, etc.). Because the surgeon 50 can see a visual rendering of the planned resection plane and the location/orientation of the femoral implant, the surgeon 50 can alter the location and orientation of the planned resection plane and/or femoral implant until the surgeon 50 is satisfied with the final fitting of the femoral implant to the resected distal femur.

Once the femoral implant planning is complete, the algorithm 120 advances to process step 148. In process step 148, the resectioning of the distal femur of the patient 56 is planned. The resection planning of the process step 148 is similar to the planning of the tibia resection performed in the process step 142. During the process step 148, a femoral resection jig is coupled with the femur bone of the patient 56. In response, the computer 12 displays an actual resection plane superimposed on the planned resection plane developed in process step 146. By repositioning the femoral resection jig, the surgeon 50 is able to alter the actual resection plane such that an accurate resection of the femur can occur.

Once the surgeon 50 has reviewed and adjusted the actual resection plane of the femur bone, the algorithm 120 advances to process step 150 in which the distal femur is resected using the appropriate resection tool and femoral jig. After the distal femur has been resected, the computer 12 displays a verified resection plane superimposed with the planned resection plane determined in process step 146. In this way, the surgeon 50 can compare the final resection of the femur with the planned resection. Again, if needed, the surgeon 50 can repeat the resectioning process to remove more the distal femur.

Figure 16:
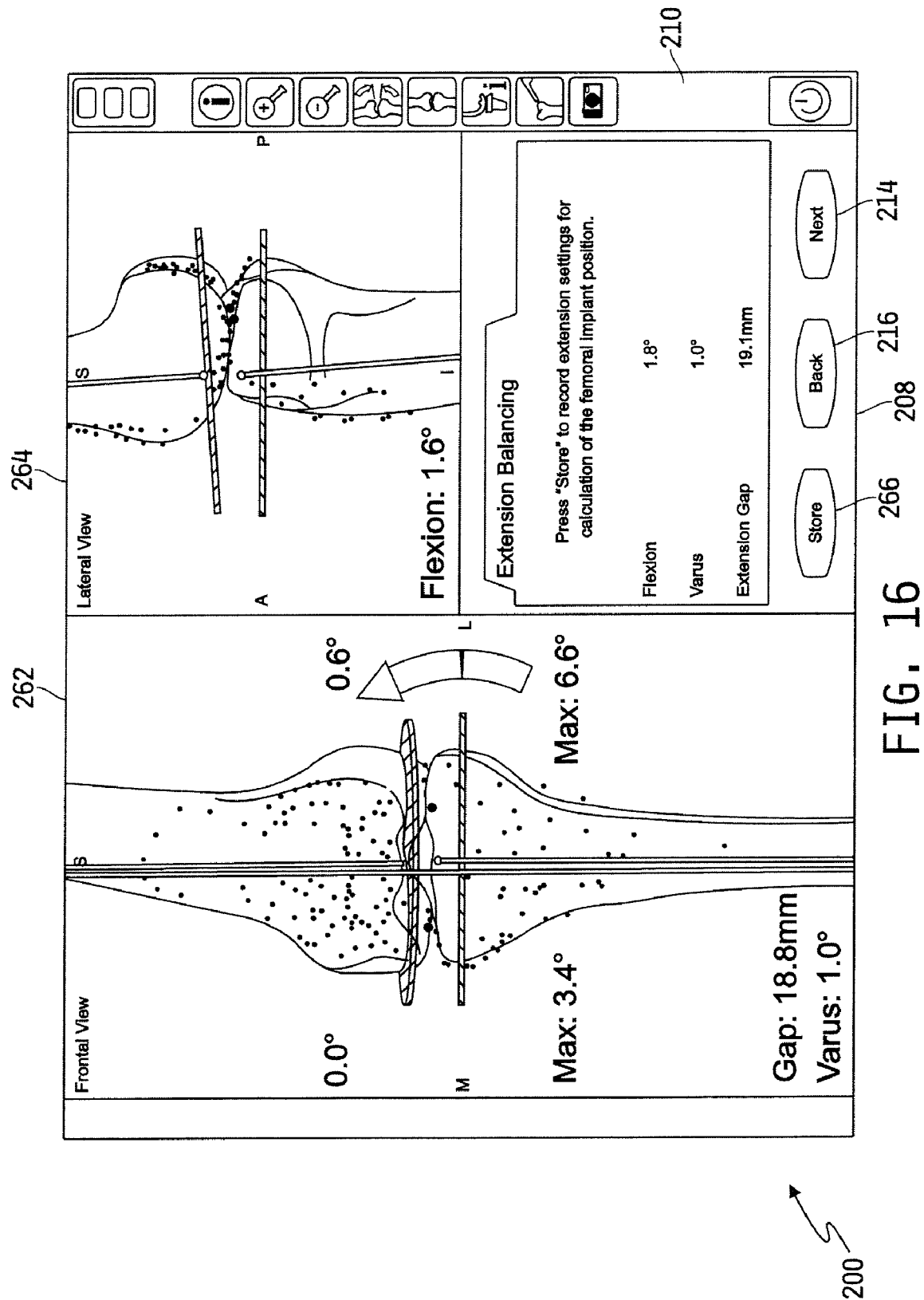

Once the distal femur of the patient 56 has been resected, the algorithm 120 advances to process step 152. In process step 152, ligament balancing of the patient's 56 tibia and femur is performed. Although illustrated as occurring after the resectioning of the tibia and femur bones in FIG. 7, ligament balancing may occur immediately following any resection step (e.g. after the tibia bone is resected) in other embodiments. In process step 152, orthopaedic implant trials (i.e., temporary orthopaedic implants similar to the selected orthopaedic implants) are inserted between the resected ends of the femur and tibia of the patient 56. As illustrated in FIG. 16, the computer 12 displays alignment data of the femur and tibia bone to the surgeon 50 via the display device 44. Specifically, the computer 12 displays a frontal view of the femur bone and tibia bone of the patient 56 in a frontal view pane 262 and a lateral view of the femur and tibia bones in a lateral view pane 264. Each of the panes 262, 264 display alignment data of the femur and tibia bones. Additional alignment data is displayed in the surgical step pane 208. The alignment data may be stored (e.g., in a data storage device included in the computer 20) by selection of a store button 266. The alignment data may subsequently be retrieved and reviewed or used in another procedure at a later time.

Ligament balancing is performed to ensure a generally rectangular shaped extension gap and a generally rectangular shaped flexion gap at a predetermined joint force value has been established between the patient's 56 proximal tibia and the distal femur. To do so, a ligament balancer may be used to measure the medial and lateral joint forces and the medial and lateral gap distances when the patient's 56 leg is in extension (i.e., the patient's 56 tibia is positioned at about 0 degrees relative to the patient's femur) and in flexion (i.e., the patient's 56 tibia is positioned at about 90 degrees relative to the patient's femur). An exemplary ligament balancer that may be used to perform these measurements is described in U.S. patent application Ser. No. 11/094,956, filed on Mar. 31, 2005, the entirety of which is expressly incorporated herein by reference. In either extension or flexion, if the medial and lateral gap distances are not approximately equal (i.e., do not form a generally rectangular shaped joint gap) at the predetermined joint force value, ligament release (i.e., cutting of a ligament) may be performed to equalize the medial and/or lateral gap distances. Additionally or alternatively, the orthopaedic implant trial may be replaced with an alternative implant trial. In this way, the surgeon 50 ensures an accurate alignment of the tibia bone and femur bone of the patient 56.

Figure 17:
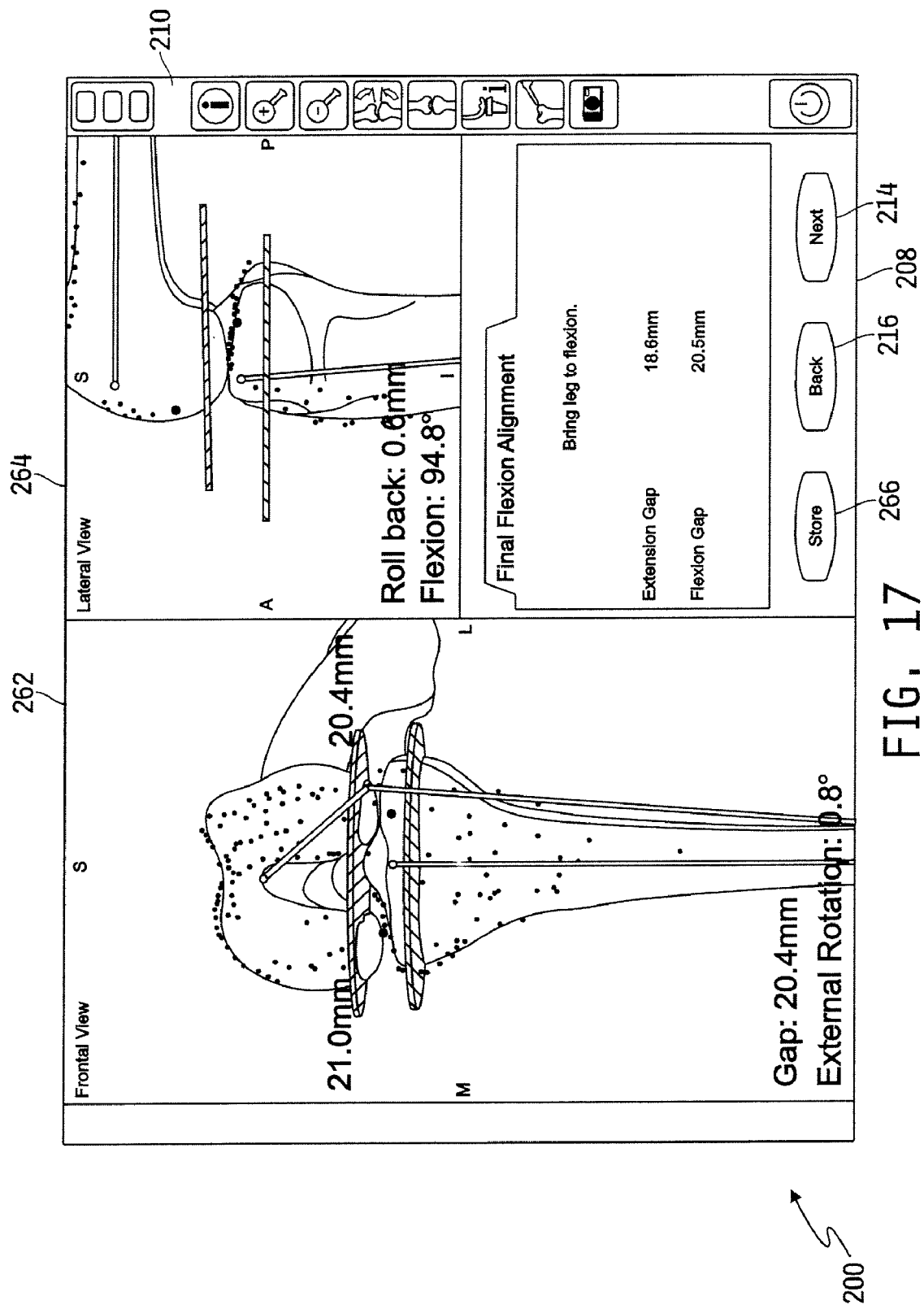

Once any desired ligament balancing is completed in process step 152, the algorithm 120 advances to process step 154 in which a final verification of the orthopaedic implants is performed. In process step 154, the orthopaedic implants are coupled with the distal femur and proximal tibia of the patient 56 and the alignment of the femur and tibia bones are verified in flexion and extension. To do so, the computer 12 displays the rendered images of the femur bone and tibia bone and alignment data to the surgeon 50 via the display device 44, as illustrated in FIG. 17. As indicated in the surgical step pane 208, the surgeon 50 is instructed to move the patient's 56 leg to flexion and extension such that the overall alignment can be determined and reviewed. If the femur and tibia bones of the patent 56 are not aligning (i.e., the flexion and/or extension gap is non-rectangular) to the satisfaction of the surgeon 50, the surgeon may perform additional ligament balancing as discussed above in regard to process step 152. Once the surgeon 50 has verified the final alignment of the femur and tibia bones (i.e., the flexion and extension gaps), the surgeon 50 may store the final alignment data via selecting the store button 266. The surgeon 50 may subsequently complete the orthopaedic surgical procedure by selecting the next button 214.

Figure 18:
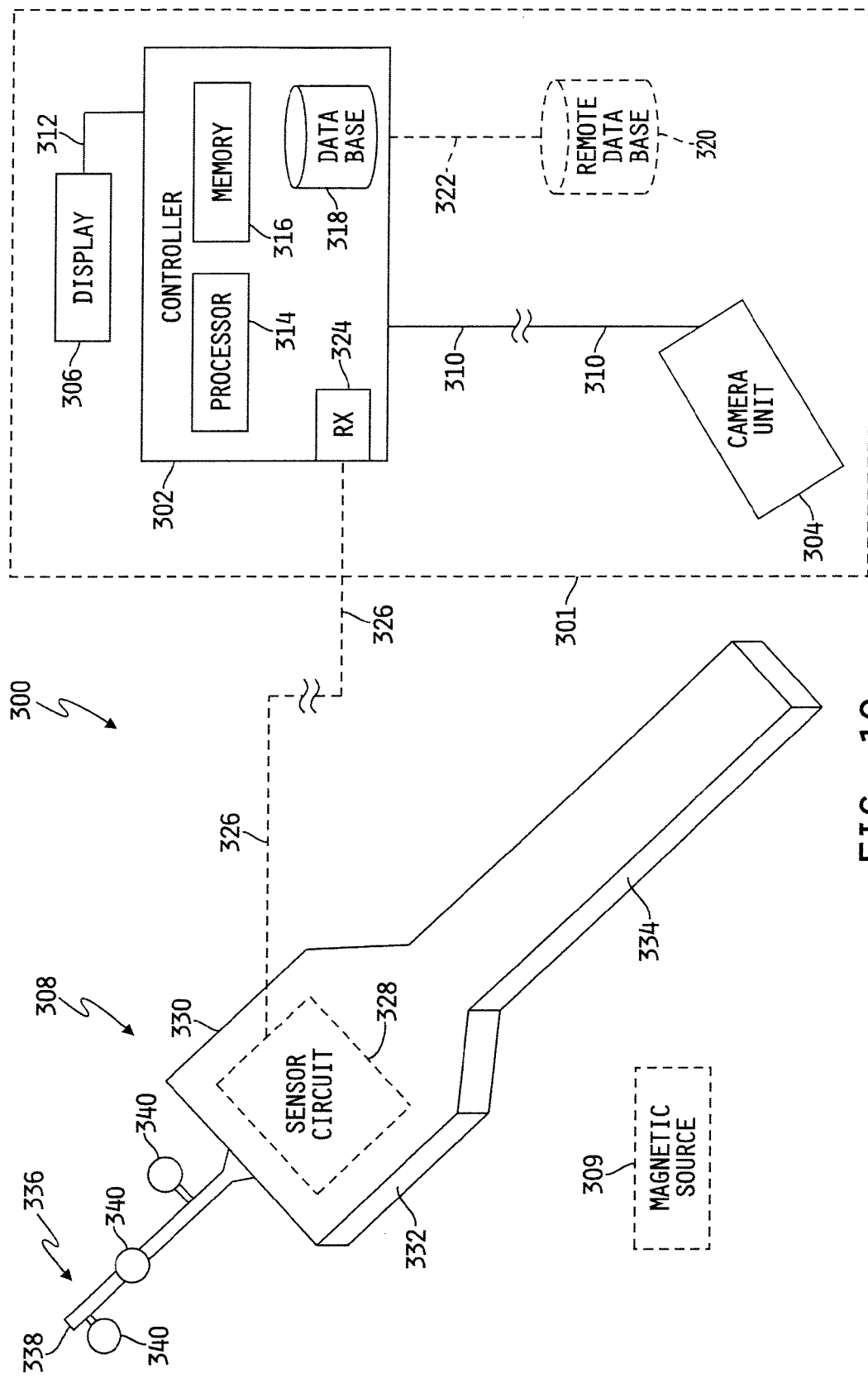
FIG. 18 is a simplified diagram of another CAOS system including a magnetic sensor array.

Referring now to FIG. 18, in another embodiment, a system 300 for pre-operatively registering a bone or bony anatomy (i.e., one or more bones) of a patient includes a computer assisted orthopaedic surgery (CAOS) system 301, a magnetic sensor array 308, and one or more magnetic sources 309. The computer assisted orthopaedic surgery (CAOS) system 301 includes a controller 302, a camera unit 304, and a display device 306. The controller 302 is communicatively coupled with the camera unit 304 via a communication link 310. The communication link 310 may be any type of communication link capable of transmitting data (i.e., image data) from the camera unit 304 to the controller 302. For example, the communication link 310 may be a wired or wireless communication link and use any suitable communication technology and/or protocol to transmit the image data. In the illustrative embodiment, the camera unit 304 is similar to and operates in a similar manner as the camera unit 16 of the system 10 described above in regard to FIG. 1. For example, the camera unit 304 includes a number of cameras (not shown) and may be used in cooperation with the controller 302 to determine the location and orientation of a number of sensor arrays positioned in the field of view of the camera unit 304, as discussed in detail above in regard to the camera unit 16. The sensor arrays may include a number of reflective elements and may be coupled with bones of a patient and/or various medical devices, such as probes, saw guides, ligament balancers, and the like, used during the orthopaedic surgical procedure. Alternatively, in some embodiments, the camera unit 304 may be replaced or supplemented with a wireless receiver (which may be included in the controller 302 in some embodiments) and the sensor arrays may be embodied as wireless transmitters (e.g., electromagnetic transmitters). Additionally, the medical devices may be embodied as "smart" medical devices such as, for example, smart surgical instruments, smart surgical trials, smart surgical implants, and the like. In such embodiments, the controller 302 is configured to determine the location of the medical devices based on wireless data signals received from the smart medical devices.

The controller 302 is communicatively coupled with the display device 306 via a communication link 312. Although illustrated in FIG. 18 as separate from the controller 302, the display device 306 may form a portion of the controller 302 in some embodiments. Additionally, in some embodiments, the display device 306 may be positioned away from the controller 302. For example, the display device 306 may be coupled with a ceiling or wall of the operating room wherein the orthopaedic surgical procedure is to be performed. Additionally or alternatively, the display device 306 may be embodied as a virtual display such as a holographic display, a body mounted display such as a heads-up display, or the like. The controller 302 may also be coupled with a number of input devices such as a keyboard and/or a mouse. However, in the illustrative embodiment, the display device 302 is a touch-screen display device capable of receiving inputs from a surgeon using the CAOS system 301. That is, the surgeon can provide input data to the display device 306 and controller 302, such as making a selection from a number of on-screen choices, by simply touching the screen of the display device 306.

The controller 302 may be embodied as any type of controller including, but not limited to, a computer such as a personal computer, a specialized microcontroller device, a collection of processing circuits, or the like. The controller 302 includes a processor 314 and a memory device 316. The processor 314 may be embodied as any type of processor including, but not limited to, discrete processing circuitry and/or integrated circuitry such as a microprocessor, a microcontroller, and/or or an application specific integrated circuit (ASIC). The memory device 316 may include any number of memory devices and any type of memory such as random access memory (RAM) and/or read-only memory (ROM). Although not shown in FIG. 18, the controller 302 may also include other circuitry commonly found in a computer system.

The controller 302 may also include a database 318. The database 318 may be embodied as any type of database, electronic library, and/or file storage location. For example, the database 318 may be embodied as a structured database or as an electronic file folder or directory containing a number of separate files and an associated "look-up" table. Further, the database 318 may be stored on any suitable device. For example, the database 318 may be stored in a set of memory locations of, for example, the memory device 316 and/or a stored on a separate storage device such as a hard drive or the like.

Additionally or alternatively, the controller 302 may be coupled to a remote database 320 via a communication link 322. The remote database 320 may be similar to the database 318 and may be embodied as any type of database, electronic library, and/or a file storage location. The remote database 320 may be located apart from the controller 302. For example, the controller 302 may be located in an orthopaedic surgery room while the remote database 318 may form a part of a hospital network and be located in a separate room or building apart from the orthopaedic surgery room. As such, the communication link 322 may be embodied as any type of communication link capable of facilitating data transfer between the controller 302 and the remote database 320. For example, in some embodiments, the communication link 322 may form a portion of a network such as a Local Area Network (LAN), a Wide Area Network (WAN), and/or a global, publicly-accessible network such as the Internet. In use, the database(s) 318, 320 is accessed by the controller 302 to store and/or retrieve images of a bone(s) of a patient as discussed in more detail in regard to FIG. 21.

The controller 302 also includes a receiver or transceiver 324. The receiver 324 is used by the processor 314 to communicate with the magnetic sensor array 308 via a communication link 326. The communication link 326 may be embodied as any type of communication link capable of transmitting data from the magnetic sensor array 308 to the controller 302. For example, the communication link 326 may be a wired or wireless communication link and use any suitable communication technology and/or protocol to transmit the data. As such, the receiver 324 may be embodied as any type of receiver capable of facilitating communication between the controller 302 and the magnetic sensor array 308 including, for example, a wired or wireless receiver.

The illustrative magnetic sensor array 308 of FIG. 18 includes a housing 330 having a sensing head portion 332 and a handle 334 coupled to the head portion 332. The handle 334 may be used by a user of the system 300, such as an orthopaedic surgeon, to move and position the magnetic sensor array 308. The magnetic sensor array 308 also includes a sensor circuit 328 located in the head portion 332. As discussed in more detail below in regard to FIGS. 19-33, the sensor circuit 328 is configured to sense a magnetic field generated by the magnetic source 309 and determine data indicative of a position of the magnetic source 309 relative to the magnetic sensor array 308 and transmit such data via the communication link 326 and receiver 324 to the controller 302. It should be understood that, as used herein, the term "position" is intended to refer to any one or more of the six degrees of freedom which define the location and orientation of a body (e.g., the magnetic source 309) in space or relative to a predetermined point or other body.

In some embodiments, the magnetic sensor array 308 may also include a reflective sensor array 336. The reflective sensor array 336 includes a support frame 338 and a number of reflective sensor elements 340. The reflective sensor array 336 is similar to the sensor arrays 54, 62, 82, 96 described above in regard to FIGS. 2, 3, 4, and 5, respectively. The reflective sensor elements 340 are positioned in a predefined configuration that allows the controller 302 to determine the identity and position (i.e., three dimensional location and orientation) of the magnetic sensor array 308 based on the configuration. That is, when the magnetic sensor array 308 is positioned in the field of view of the camera unit 304, the controller 302 is configured to determine the identity and position of the magnetic sensor array 308 relative to the camera 304 and/or controller 302 based on the images received from the camera unit 304 via the communication link 310. In other embodiments, the reflective sensor array 336 may replaced or complimented with a wireless transmitter. In such embodiments, the controller 302 includes a wireless receiver and is configured to determine the position and identity of the magnetic sensor array based on transmitted data received from the wireless transmitter.

Figure 19:
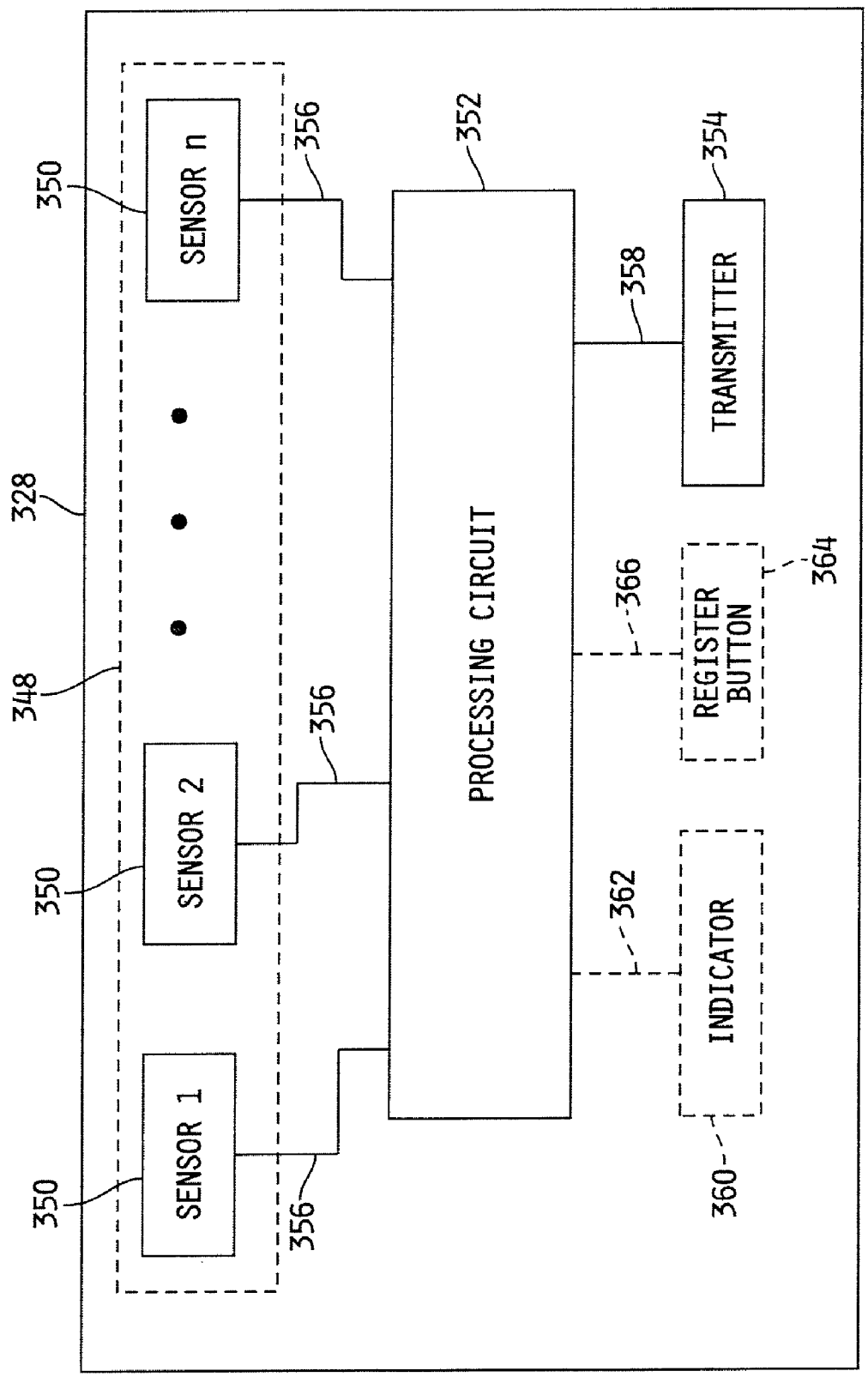
FIG. 19 is a simplified circuit diagram of one embodiment of a sensor circuit of the magnetic sensor array of FIG. 18.

To sense the magnetic field(s) of the magnetic source 309, the sensor circuit 328 includes a magnetic sensor arrangement 348 as illustrated in FIG. 19. The magnetic sensor arrangement 348 includes one or more magnetic sensors 350. The sensor circuit 328 also includes a processing circuit 352 and a transmitter 354. The magnetic sensors 350 are electrically coupled to the processing circuit 352 via a number of interconnects 356. The processing circuit 352 is also electrically coupled to the transmitter 354 via an interconnect 358. The interconnects 356, 358 may be embodied as any type of interconnects capable of providing electrical connection between the processing circuit 352, the sensors 350, and the transmitter 354 such as, for example, wires, cables, PCB traces, or the like.

The number of magnetic sensors 350 that form the magnetic sensor arrangement 348 may depend on such criteria as the type of magnetic sensors used, the specific application, and/or the configuration of the magnetic sensor array 308. For example, the magnetic sensors 350 are configured to measure a three-dimensional magnetic field of the magnetic source 309. As such, the sensor circuit 328 may include any number and configuration of one-dimensional, two-dimensional, and/or three-dimensional magnetic sensors such that the sensor circuit 328 is capable of sensing or measuring the magnetic field of the magnetic source 309 in three dimensions. Additionally, the magnetic sensor(s) 350 may be embodied as any type of magnetic sensor capable of sensing or measuring the magnetic field generated by the magnetic source 309. For example, the magnetic sensors 350 may be embodied as superconducting quantum interference (SQUID) magnetic sensors, anisotropic magnetoresistive (AMR) magnetic sensors, giant magnetoresistive (GMR) magnetic sensors, Hall-effect magnetic sensors, or any other type of magnetic sensors capable of sensing or measuring the three-dimensional magnetic field of the magnetic source. In one particular embodiment, the magnetic sensor(s) are embodied as X-H3X-xx_E3C-25HX-2.5-0.2T Three Axis Magnetic Field Transducers, which are commercially available from SENIS GmbH, of Zurich, Switzerland. Regardless, the magnetic sensors 350 are configured to produce a number of data values (e.g., voltage levels) which define one or more of the components (e.g., X-, Y-, and Z-components) of the three-dimensional magnetic flux density of the magnetic field of the magnetic source 309 at the point in space where each sensor is located and in the orientation of each sensor's active sensing element. These data values are transmitted to the processing circuit 352 via the interconnects 356.

Figure 20:
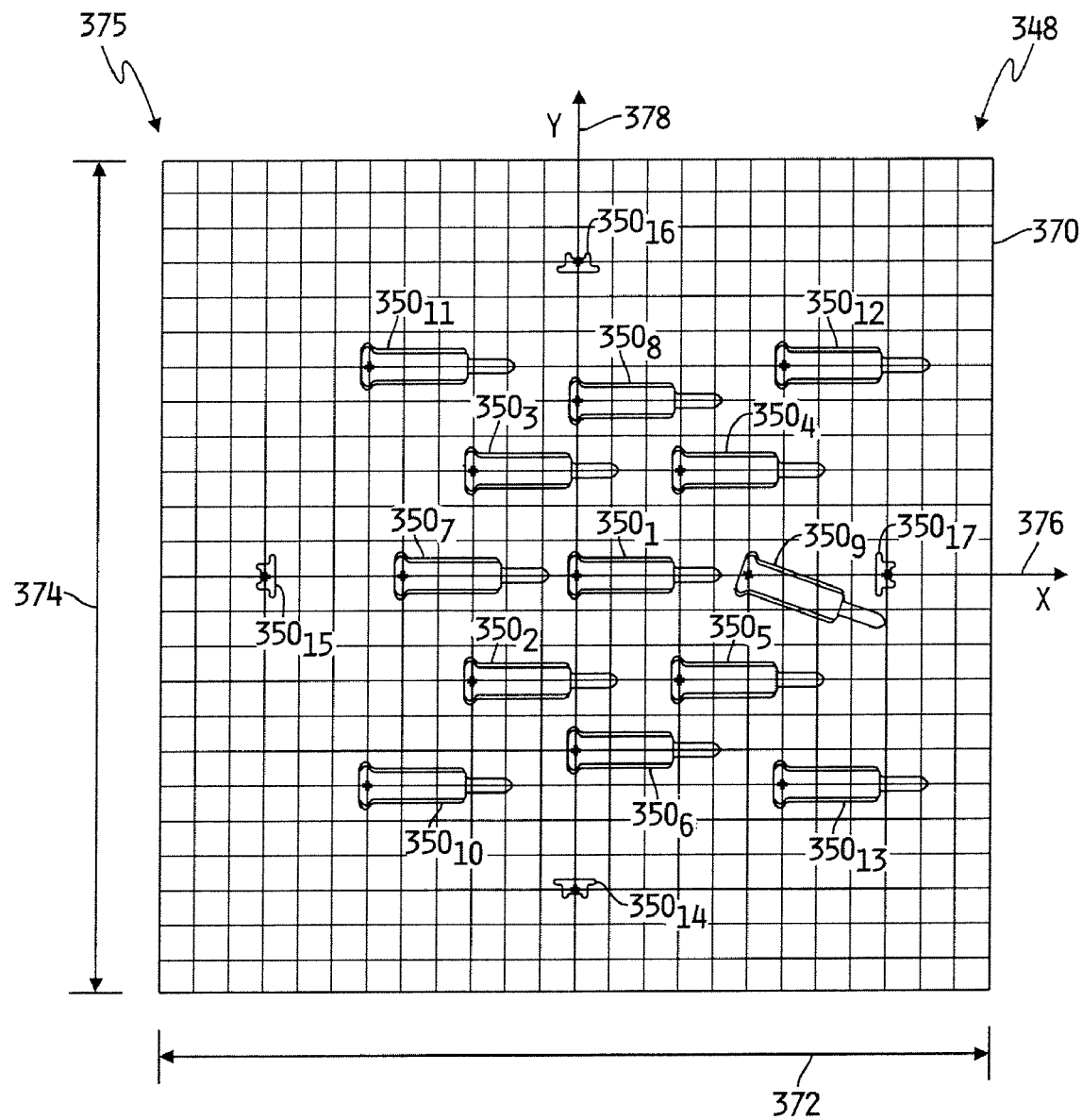
FIG. 20 is a plan view of one embodiment of a magnetic sensor arrangement of the sensor circuit of FIG. 19.

In one particular embodiment, the magnetic sensor arrangement 348 includes seventeen magnetic sensors $350_1$-$350_{17}$ configured as illustrated in FIG. 20. The magnetic sensors $350_1$-$350_{17}$ are secured to a sensor board 370. The sensor board 370 may be formed from any non-magnetic material capable of supporting the magnetic sensors $350_1$-$350_{17}$ in the desired configuration. For example, in the illustrative embodiment, the sensor board 370 is formed from FR4. The magnetic sensors $350_1$-$350_{17}$ may be mounted on or in the sensor board 370. As such, the sensor board 370 forms the sensing face of the sensor circuit 328 and may be located inside the head portion 332 of the magnetic sensor array 308 (i.e., located behind the housing material) or mounted to the head portion 332 such that the sensor board 370 is exposed.

The illustrative sensor board 370 has a width 372 of about 12 centimeters, a length 374 of about 12 centimeters, and a thickness (not shown) of about 1.25 centimeters. However, sensor boards having other dimensions that allow the mounting of the desired number of magnetic sensors 350 may be used. The magnetic sensors 350 are mounted to or in the sensor board 370 according to a predetermined configuration. For clarity of description, a grid 375 having an X-axis 376 and a Y-axis 378 is illustrated over the sensor board 370 in FIG. 20. In the illustrative embodiment, each unit of the grid 375 has a measurement of about 5 millimeters. Each of the magnetic sensors $350_1$-$350_{17}$ may be a one dimensional, two dimensional, or three dimensional sensor. As such, each of the magnetic sensors $350_1$-$350_{17}$ may include one, two, or three active sensing elements, respectively. Each sensing element of the magnetic sensors $350_1$-$350_{17}$ is capable of measuring at least one component of the magnetic flux density of a magnetic source at the position (i.e., location and orientation) of the particular magnetic sensor. To do so, each magnetic sensor 350 includes a field sensitive point, denoted as a "+" in FIG. 20, wherein the magnetic flux density is measured. The configuration of the magnetic sensors $350_1$-$350_{17}$ will be described below in reference to the field sensitive point of each magnetic sensor with the understanding that the body of the sensor may be positioned in numerous orientations wherein each orientation facilitates the same location of the field sensitive point.

As illustrated in FIG. 20, the first magnetic sensor $350_1$ is located at a central point (0, 0) on the grid 375. The first magnetic sensor $350_1$ is a three-dimensional magnetic sensor having three channels and generates data values (i.e., voltage levels) indicative of the X-, Y-, and Z-components of the measured magnetic flux density at the position of the sensor $350_1$. Four additional three-dimensional magnetic sensors $350_2$-$350_5$ are positioned around the first magnetic sensor $350_1$. The magnetic sensor $350_2$ is located at point (−15, 15), the magnetic sensor $350_3$ is located at point (−15, 15), the magnetic sensor $350_4$ is located at point (15, 15), and the magnetic sensor $350_5$ is located at point (15, −15), wherein each graduation mark of the grid 375 is defined as 5 units (e.g., 5 millimeters).

The magnetic sensor arrangement 348 also includes a number of single-dimensional magnetic sensors $350_6$-$350_{17}$. The magnetic sensors $350_6$-$350_{13}$ are positioned on the sensor board 370 such that the sensors $350_6$-$350_{13}$ measure the Z-component of the measured magnetic flux density (i.e., the magnetic flux generated by the magnetic source 309). In particular, the magnetic sensor $350_6$ is located at point (0, −25), the magnetic sensor $350_7$ is located at point (−25, 0), the magnetic sensor $350_8$ is located at point (0, 25), the magnetic sensor $350_9$ is located at point (25, 0), the magnetic sensor $350_{10}$ is located at point (−30, −30), the magnetic sensor $350_{11}$, is located at point (−30, 30), the magnetic sensor $350_{12}$ is located at point (30, 30), and the magnetic sensor $350_{13}$ is located at point (30, −30).

Conversely, the one-dimensional magnetic sensors $350_{14}$, $350_{16}$, and the magnetic sensors $350_{15}$, $350_{17}$ are positioned on the sensor board 370 such that the one-dimensional sensors $350_{14}$, $350_{16}$ and $350_{15}$, $350_{17}$ measure the magnitude of the Y-axis and X-axis components of the magnetic flux density of the measured magnetic field, respectively. In particular, the magnetic sensor $350_{14}$ is located at point (0, −45), the magnetic sensor $350_{15}$ is located at point (−45, 0), the magnetic sensor $350_{16}$ is located at point (0, 45), and the magnetic sensor $350_{17}$ is located at point (45, 0). As illustrated in FIG. 20, the magnetic sensors $350_{14}$-$350_{17}$ are positioned in or embedded in the sensor board 370 such that the magnetic sensors $350_{14}$-$350_{17}$ are positioned orthogonally to the measurement surface of the sensor board 370. Conversely, the magnetic sensors $350_1$-$350_{13}$ are positioned on the sensor board 370 coplanar with the measurement surface of the sensor board 370 or otherwise substantially parallel therewith.

In some embodiments, the magnetic sensors 350 may have differing magnetic field sensitivities (i.e., the ability to detect a change in the measured magnetic flux density) and sensing ranges. For example, in some embodiments, the magnetic sensors 350 located toward a central location of the sensor board 370 may have a lower magnetic field sensitivity but a greater sensing range than the magnetic sensors 350 located farther from the central location. In the illustrative embodiment of FIG. 20, the three-dimensional magnetic sensors $350_1$-$350_5$, which are located toward the center of the sensor board 370, have a lower magnetic field sensitivity and a greater sensing range than the one-dimensional magnetic sensors $350_6$-$350_{17}$ For example, in one particular embodiment, the three-dimensional magnetic sensors $350_1$-$350_5$ have a magnetic sensitivity of about 50 µT (micro-Tesla) and a sensing range of about 20 mT (milli-Tesla) while the one-dimensional magnetic sensors $350_6$-$350_{17}$ have a magnetic sensitivity of about 5 µT and a sensing range of about 2 mT. However, in other embodiments, there may be additional levels or differences of magnetic sensitivity and/or sensing range based on the particular distance of each magnetic source 350 from a predetermined location on the sensor board 370.

Because of such differences in magnetic field sensitivity and sensing range of the magnetic field sensors 350, the magnetic sensor arrangement 348 may be less susceptible to positioning variances of the magnetic sensor array 308 and/or the accuracy of the magnetic flux density measurements may be improved by having magnetic sensors 350 capable of measuring the magnetic flux density of the magnetic source 309 while the magnetic sensor array is positioned close to the magnetic source 309 without going into saturation. Additionally, the magnetic sensor arrangement 348 may be less susceptible to positioning variances of the magnetic sensor array 308 and/or the accuracy of the magnetic flux density measurements may be improved by having magnetic sensors 350 capable of measuring the magnetic field of the magnetic source 309 while the magnetic sensor array 308 is positioned far from the magnetic source 309 in spite of the increase in magnetic "noise" (i.e., undesirable magnetic field effects from sources other than the magnetic source 309). To further improve the measurement accuracy of the magnetic sensor array 308, the measurements of the array 308 may be verified as discussed in detail below in regard to process step 402 of algorithm 400 shown in FIG. 24.

It should be appreciated that the magnetic sensor arrangement 348 is only one illustrative embodiment and that, in other embodiments, the sensor arrangement 348 of the sensor circuit 328 may include any number of magnetic sensors 350 positioned in any configuration that allows the magnetic sensors 350 to measure the three-dimensional X-, Y-, and Z-components of the measured magnetic flux density. For example, in some embodiments, the magnetic sensor arrangement 348 may include a single three-dimensional magnetic sensor. Alternatively, in other embodiments, the magnetic sensor arrangement 348 may include additional magnetic sensors 350 arranged in various configurations. It should be appreciated that by increasing the number of magnetic sensors, an amount of redundancy is developed. That is, magnitudes of the individual components of the measured magnetic flux densities are determined using measurements from a number of magnetic sensors 350 positioned in different locations. For example, referring to the illustrative magnetic sensor arrangement 348 illustrated in FIG. 20, the magnitudes of the Z-component of the measured magnetic flux densities are determined using the measurements from magnetic sensors $350_1$-$350_{13}$. As such, it should be appreciated that the accuracy of the characterization of the three-dimensional magnetic field generated by the magnetic source 309 may be increased by including additional magnetic sensors in the magnetic sensor arrangement 348.

Further, although the magnetic sensors 350 are embodied as separate magnetic sensors apart from the processing circuit 352 in the illustrative embodiment of FIGS. 18-20, in some embodiments, the magnetic sensors 350 and the processing circuit 352, or portions thereof, may be embodied as a single electronic device. For example, the magnetic sensors 350 and portions of the processing circuit 352 may be embodied as one or more complimentary metal oxide semiconductor (CMOS) device(s). By embedding the magnetic sensors 350 and processing circuit 352 in a semiconductor device, the required space of the sensor circuit 328 is reduced. Additionally, such a semiconductor device may be less susceptible to outside influences such as temperature variation of the individual magnetic sensors 350.

Referring back to FIG. 19, the processing circuit 352 may be embodied as any collection of electrical devices and circuits configured to determine the position of the magnetic source 309. For example, the processing circuit 352 may include any number of processors, microcontrollers, digital signal processors, and/or other electronic devices and circuits. In addition, the processing circuit 352 may include one or more memory devices for storing software/firmware code, data values, and algorithms.

In some embodiments, the processing circuit 352 is configured to determine position data indicative of the position of the magnetic source 309 relative to the magnetic sensor array 308 based on the measurements of magnetic sensors 350. To do so, the processing circuit 352 may execute an algorithm for determining the position of the magnetic source 309 relative to the magnetic sensor array 308 as discussed in detail below in regard to algorithms 820 and 830 and illustrated in FIGS. 26 and 27. The position data may be embodied as coefficient values or other data usable by the controller 302, along with pre-operative images of the relevant bones and magnetic sources 309, to determine the position (i.e., location and orientation) of the magnetic source 309. The processing circuit 352 controls the transmitter 354 via interconnect 358 to transmit the position data to the controller 302 via the communication link 326. Alternatively, in other embodiments, the processing circuit 332 is configured only to transmit the measurements of the magnetic sensors 350 to the controller 302 via the transmitter 354. In response, the controller 302 executes the algorithm for determining the position of the magnetic source 309 using the measurements received from the magnetic sensor array 308. In such embodiments, the overall footprint (i.e., size) of the sensor circuit 328 may be reduced because some of the circuitry of the processing circuit 352 may not be required since the processing circuit 352 is not configured to determine the position data.

In some embodiments, the sensor circuit 328 may also include an indicator 360. The indicator 360 may be embodied as any type of indicator including a visual indicator, an audible indicator, and/or a tactile indicator. The indicator 360 is electrically coupled to the processing circuit 352 via an interconnect 362, which may be similar to interconnects 356, 358. In such embodiments, the processing circuit 352 is configured to activate the indicator 360 when the magnetic sensor array 308 (i.e., the magnetic sensors 350) is positioned in a magnetic field of a magnetic source 309. For example, the processing circuit 352 may be configured to monitor the magnetic flux densities sensed by the magnetic sensor(s) 350 in one or more of the X-, Y-, and/or Z-directions shown in FIG. 20 and activate the indicator 360 when the magnetic flux density in one or more of the X-, Y-, and/or Z-directions reaches or surpasses a predetermined threshold value. In this way, the magnetic sensor array 308 is capable of notifying the surgeon or other user of the array 308 when the array 308 has been properly positioned such that the magnetic sensor array 308 can accurately sense or measure the magnetic flux density of the magnetic source 309.

Further, in some embodiments the sensor circuit 328 may include a register button 364. The register button 364 may be located on an outside surface of the magnetic sensor array 308 such that the button 364 is selectable by a user (e.g., an orthopaedic surgeon) of the array 308. The button 364 may be embodied as any type of button such as a push button, toggle switch, software implemented touch screen button, or the like. The register button 364 is electrically coupled to the processing circuit 352 via an interconnect 366, which may be similar to interconnects 356, 358. The register button 364 may be selected by a user, such as an orthopaedic surgeon, of the magnetic sensor array 308 to transmit the position data and/or measurement values of the magnetic sensors 350 to the controller 302. That is, as discussed in more detail below in regard to algorithm 820, once the magnetic sensor array is properly positioned to measure the magnetic field of the magnetic source 309, the surgeon may select the register button 364 to cause the magnetic sensor array to transmit the data. In some embodiments, the register button 364 is only operable while the magnetic sensor array 308 is properly positioned. For example, the register button 364 may be selected to transmit the position data/measured values only while the processing circuit 352 has determined that the measured magnetic flux density (e.g., in the Z-axis direction) is above a predetermined threshold value or within a predetermined range of values. As discussed above in regard to the indicator 360, the surgeon is notified when the magnetic sensor array is properly positioned by the activation of the indicator 360.

Although the illustrative magnetic sensor array 308 is illustrated as a hand-held device including the sensor circuit 328 located therein, in other embodiments, the magnetic sensor array 308 may be embodied as a single magnetic sensor, a number of magnetic sensors, or a collection of magnetic sensors and other circuitry. Additionally, in other embodiments, the magnetic sensor array 308 may include one or more remote magnetic sensors located apart from the sensor circuit 328. By displacing the remote magnetic sensor(s) from the sensor circuit 328, unwanted magnetic interferences caused by environmental magnetic fields such as magnetic effects caused from the Earth's magnetic field, stray magnetic fields in the operating room, and the like, may be adjusted out of or otherwise compensated for in the sensor circuit 328 as discussed in more detail below in regard to process step 831 of algorithm 830 described below in regard to and illustrated in FIG. 27.

As illustrated in FIG. 21, in some embodiments, the magnetic sensor array 308 may include a remote magnetic sensor housing 380. The remote magnetic sensor housing 380 includes a support frame 382 extending a distance 383 up from the head portion 332 of the magnetic sensor array 308. The remote magnetic sensor housing 380 includes a head portion 384 coupled to the top of the support frame 382. A remote magnetic sensor 386 is located in the head portion 382 and electrically coupled to the sensor circuit 328 via an interconnect 388. The interconnect 388 may be any type of interconnect capable of providing communication between the remote magnetic sensor 386 and the sensor circuit 328. In some embodiments, the remote magnetic sensor housing 380 is capable of being mechanically decoupled from the magnetic sensor array 308 such that the housing 380 and remote magnetic sensor 386 may be positioned further away from or in an alternative position in relation to the sensor circuit 328.

The remote magnetic sensor 386 is similar to the magnetic sensors 350 and may be a one-, two-, or three-dimensional magnetic sensor. In one particular embodiment, the remote magnetic sensor 386 is a three-dimensional sensor configured to measure the X-, Y-, and Z-components of the magnetic field at the position of the remote magnetic sensor 386. The remote magnetic sensor 386 is spaced apart from the sensor circuit 328 such that interfering magnetic fields (i.e., magnetic fields other than the desired magnetic field) may be measured. That is, the remote magnetic sensor 386 is located such that it is far enough away from the magnetic source 309 such that the magnetic field generated by the magnetic source 309 has minimal impact on the measurements of the remote magnetic sensor 386. As such, the remote magnetic sensor 386 is configured to measure magnetic fields generated by sources other than the magnetic source 309. The measurements generated by the remote magnetic sensor 386 are transmitted to the sensor circuit 328 via the interconnect 388. The sensor circuit 328 may be configured to compensate or adjust the magnetic field measurements of the magnetic sensors 350 based on the measurements of the remote magnetic sensor 386. In this way, unwanted magnetic field effects can be subtracted out of the measurements of the magnetic sensors 350 or otherwise accounted for.

Additionally, other embodiments of the magnetic sensor array 308 may include a housing having different configurations than that illustrated in FIG. 18. For example, as illustrated in FIG. 22, a magnetic sensor array 390 may include a sensing head portion 392 having the sensor circuit 328 located therein. A handle 394 is coupled to the head portion 392 and includes the remote magnetic sensor 386, which is electrically coupled to the sensor circuit 328 via an interconnect 396. The interconnect 396 is similar to the interconnect 388 and may be embodied as any type of interconnect capable of providing communication between the remote magnetic sensor 386 and the sensor circuit 328. In the illustrative embodiments, the handle 394 is a closed loop handle and is coupled to the sensing head portion 392 at each distal end. As discussed above in regard to FIG. 21, the sensor circuit 328 uses the measurements generated by the remote magnetic sensor 386 to compensate or calibrate the magnetic sensors 350 of the sensor circuit 328.

Figure 23:
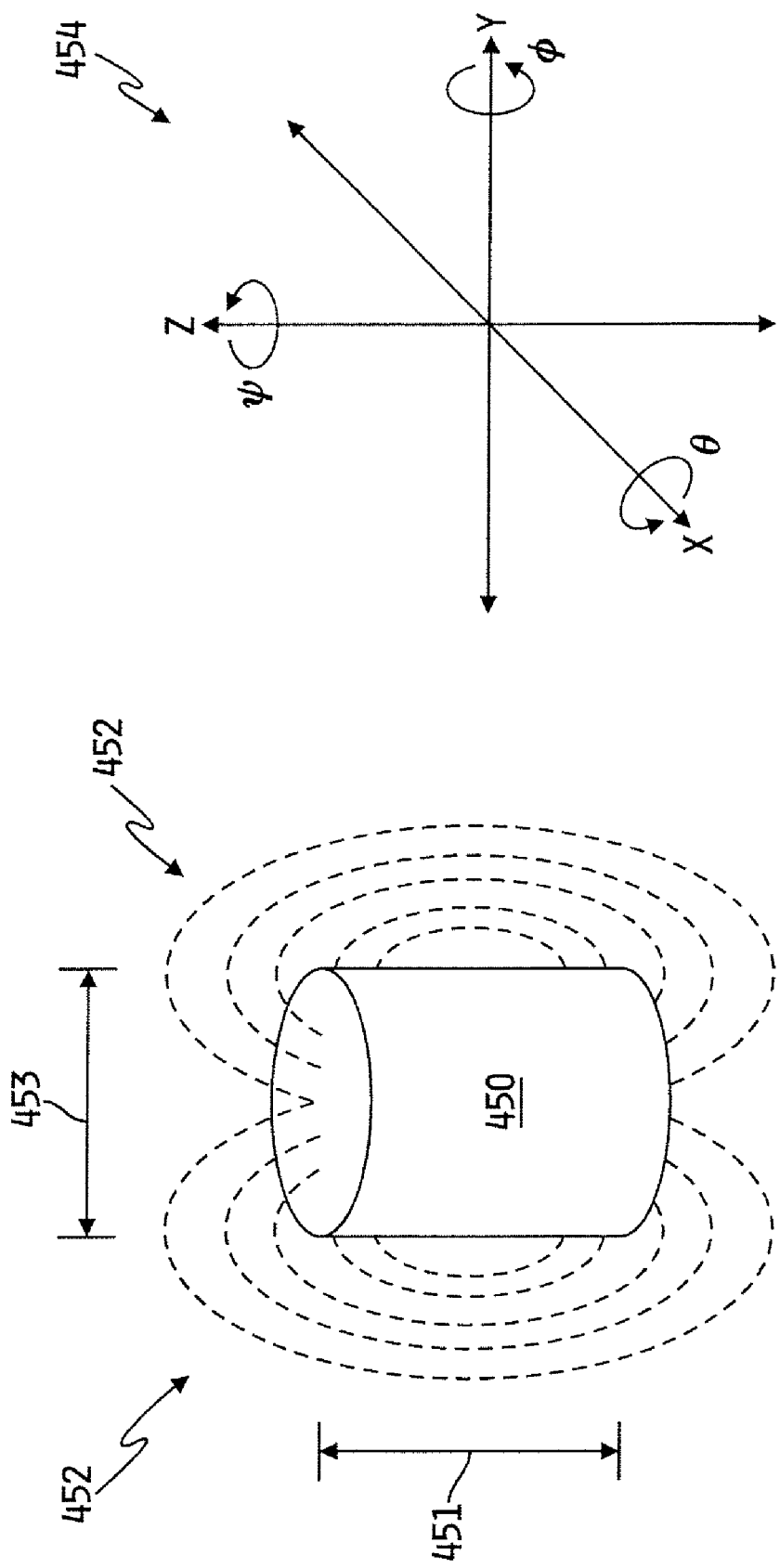
FIG. 23 is a perspective view of one embodiment of a magnetic source.

Referring now to FIG. 23, the magnetic source 309 may be embodied as one or more magnets. In the illustrative embodiment, the magnetic source 309 is embodied as two or more cylindrical, dipole magnets 450. The magnet(s) 450 generate a magnetic field having a number a magnetic flux lines 452. It should be appreciated that only a subset cross-section of the generated flux lines 452 is illustrated in FIG. 23 and that the flux lines (and magnetic field) circumferentially surround the magnet(s) 450. When coupled to a bone(s) of a patient, the position (i.e., location and orientation) of the magnets 450 is defined by six degrees of freedom. That is, the position of the magnet(s) 450 can be defined by three Cartesian coordinate values and three rotational values (i.e., one about each Cartesian axis). For example, as illustrated in FIG. 23 by coordinate axes 454, the position of the magnet(s) 450 can be defined in three-dimensional space by an X-coordinate value, a Y-coordinate value, a Z-coordinate value, a (theta) θ-rotational value about the X axis, a (phi) φ-rotational value about the Y axis, and a (psi) ψ-rotational value about the Z axis.

The magnet 450 may be formed from any magnetic material capable of generating a magnetic field of sufficient magnetic flux density or strength to be sensed or measured by the sensor circuit 328 through the relevant tissue of a patient. For example, the magnet 450 may be formed from ferromagnetic, ferrimagnetic, antiferromagnetic, antiferrimagnetic, paramagnetic, or superparamagnetic material. In one particular embodiment, the magnet 450 is formed from a neodymium ferrite boron (NdFeB) grade 50 alloy material. The illustrative magnet 450 is a cylindrical magnet having a length 451 of about five millimeters and a diameter 453 of about two millimeters. However, in other embodiments, magnets 450 having other configurations, such as rectangular and spherical magnets, and sizes may be used.

To improve the accuracy of the measurements of the magnetic sensors 350, in some embodiments, the plurality of magnets 450 which embody the magnetic source 309 are formed or manufactured such that the magnetic qualities of each magnet 450 are similar. To do so, in one embodiment, the magnetic field generated by each magnet 450 is measured and determined. Only those magnets 450 having similar magnetic fields are used. Additionally, in some embodiments, the magnetic moment of each magnet 450 may be determined. Only those magnets 450 with magnetic moments on-axis or near on-axis with the magnet's 450 longitudinal axis are used. That is, if the magnetic moment of the magnet 450 is determined to extend from the magnet 450 from a location substantially off the longitudinal axis of the magnet 450, the magnet 450 may be discarded. In this way, the magnetic fields generated by each of the magnets 450 are similar and, as such, measurements of the magnetic fields and calculated values based thereon may have increased accuracy.

Figure 28:
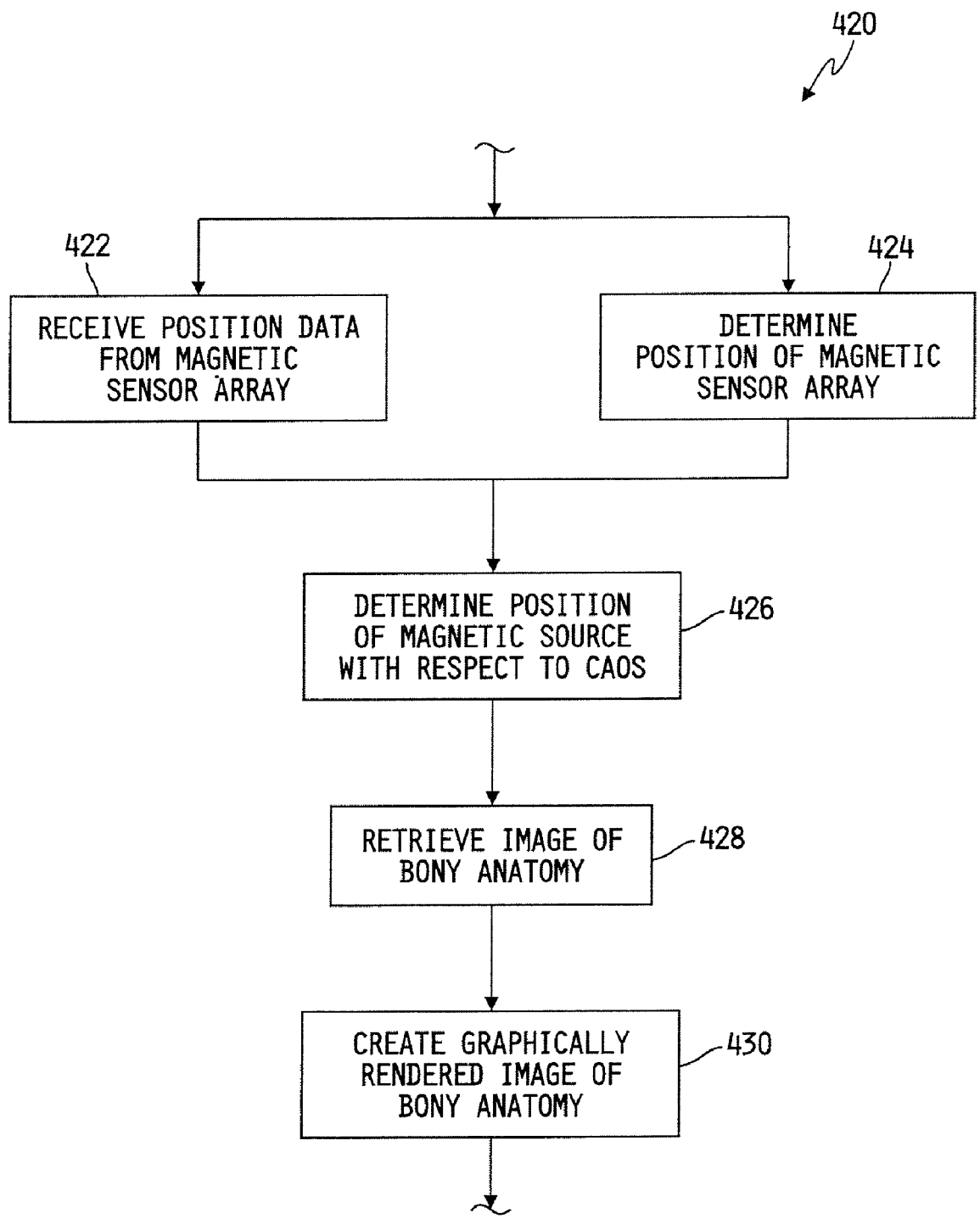
FIG. 28 is a simplified flowchart of an algorithm for determining a position of a bony anatomy of a patient.
Figure 29:
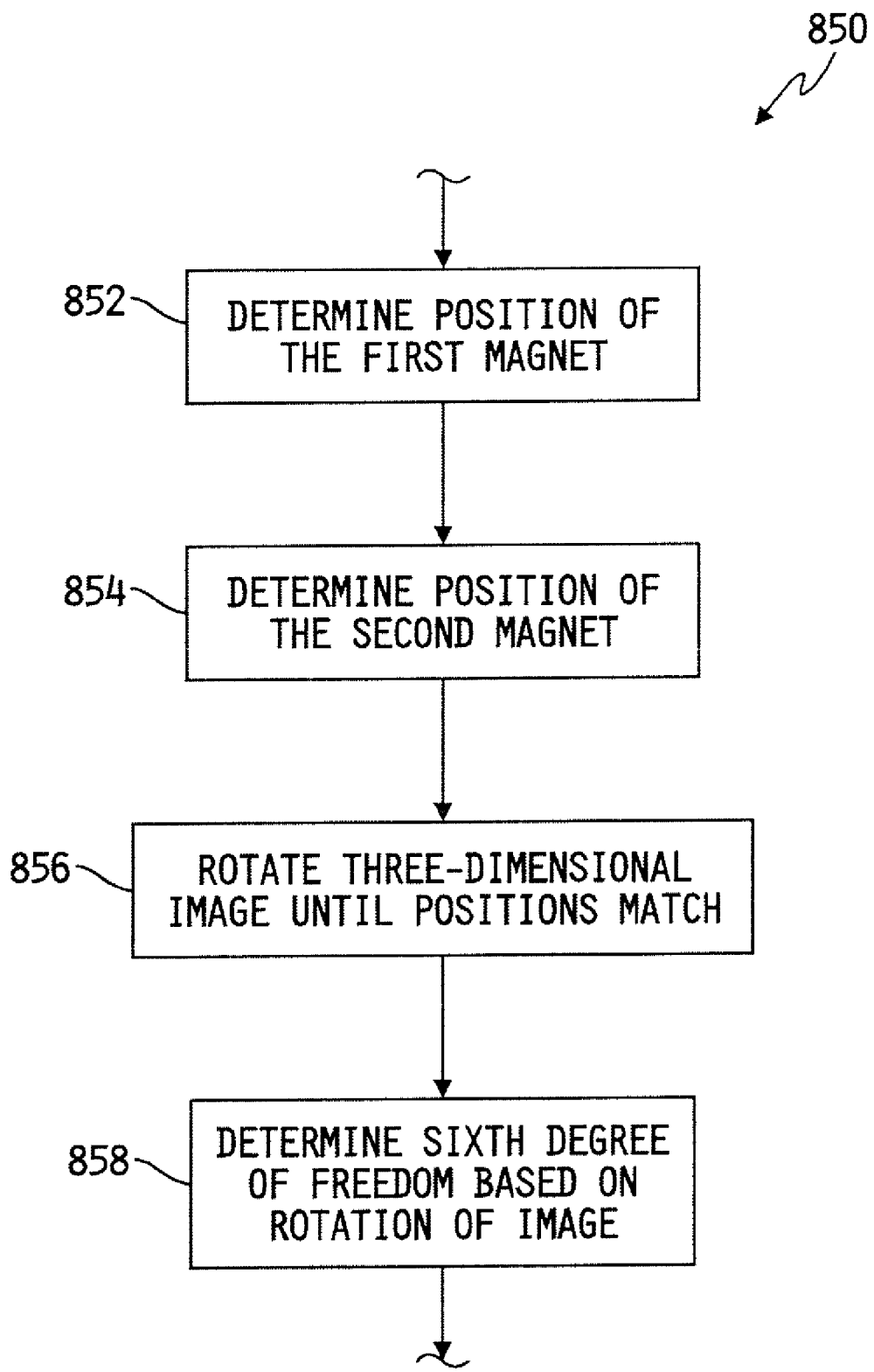
FIG. 29 is a simplified flowchart of an algorithm for determining a translation and rotation matrix relating the positions of two or more magnets.
Figure 30:
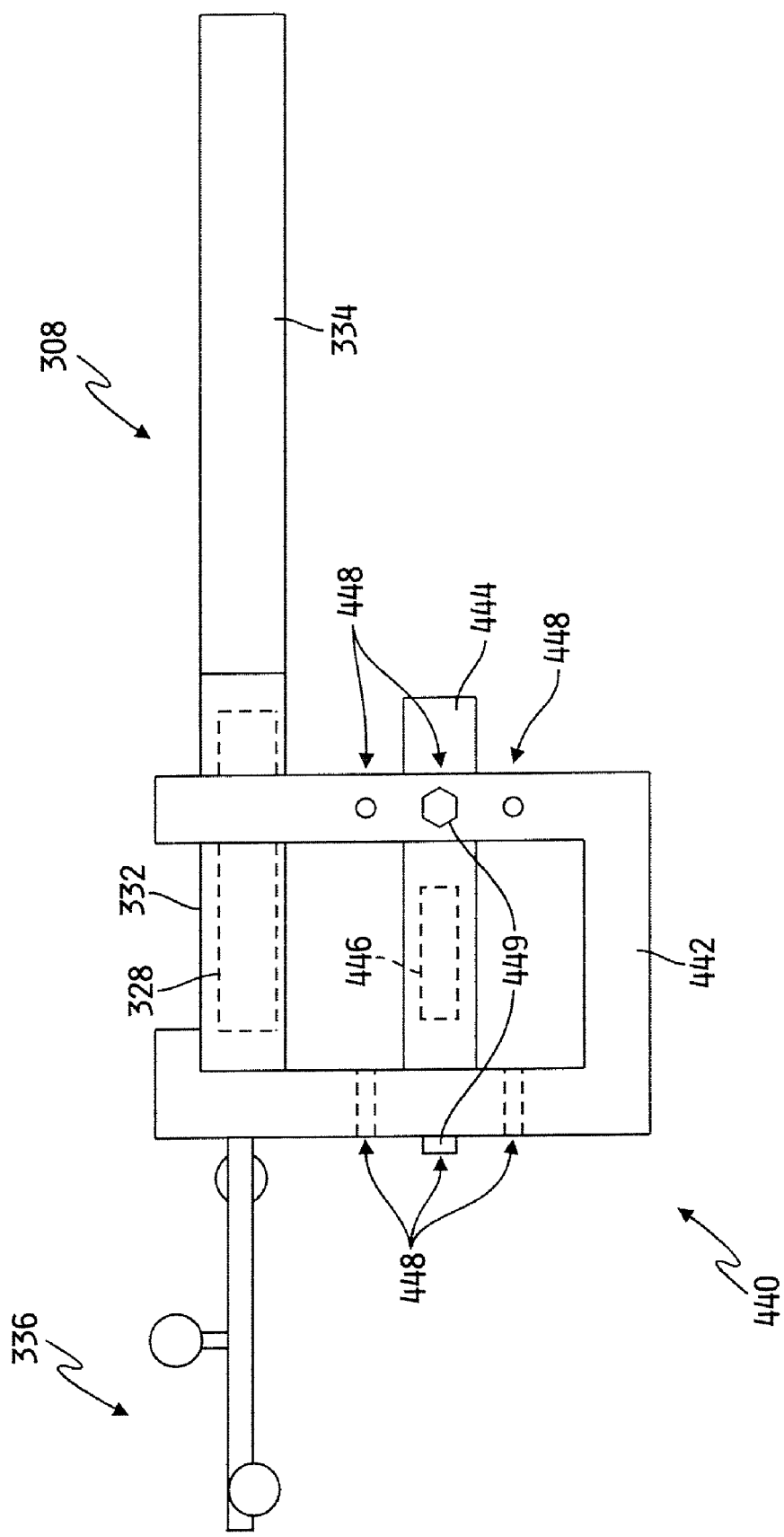
FIG. 30 is a side elevation view of a test apparatus coupled to the magnetic sensor array of FIG. 18.

Referring now to FIGS. 24-29, an algorithm 400 for registering a bone of a patient with a computer assisted orthopaedic surgery (CAOS) system begins with an optional process step 402 in which the accuracy of the magnetic sensor array 308 is verified (e.g., the accuracy of the measurements of the magnetic sensors 350 may be verified). Such verification process may be executed before each registration procedure or as part of a maintenance routine such as a monthly or weekly maintenance procedure. To verify the accuracy of the magnetic sensor array 308, a test apparatus 440 may be coupled to the sensing head portion 332 of the magnetic sensor array 308 as illustrated in FIG. 30. The test apparatus 440 includes a frame 442 and a magnetic source housing 444. A test magnetic source 446 is located in the housing 444. The frame 442 has a number of mounting apertures 448. The magnetic source housing 444 may be mounted to the frame 442 via the apertures 448 and mounting devices 449, such as screws or bolts. Because the frame 442 includes a number of mounting apertures 448, the housing 444, and thereby the test magnetic source 446, may be positioned at a number of different distances from the sensing head portion 332. Accordingly, because the magnetic flux density (or magnetic strength) of the test magnetic source 446 is known and the distance of the source 446 from the sensing head portion 332 (i.e., from the sensor circuit 328 located in the sensing head 332) is known, an expected magnetic flux density measurement value for each magnetic sensor 350 can be determined. The actual measured magnetic field values of each magnetic field sensor 350 (i.e., the output voltage levels of the magnetic sensors 350 indicative of one or more axes of the three-dimensional magnetic flux density components at each sensor's position) may then be compared to the expected magnetic flux density values. Any error above a predetermined threshold may be indicative of malfunction of the magnetic sensor array 308. To further improve the verification procedure, expected and measured magnetic flux density values may be determined for each location of the magnetic source housing 444 on the frame 442. The illustrative test apparatus 440 is but one embodiment of a test apparatus which may be used with the magnetic sensor array 308. In other embodiments, test apparatuses having other configurations may be used.

Next, in process step 404, the magnetic source 309 is coupled to the relevant bony anatomy of the patient. The magnetic source 309 may be implanted in or otherwise fixed to the bone or bones of the patient upon which the orthopaedic surgical procedure is to be performed. For example, if a total knee arthroplasty (TKA) surgical procedure is to be performed, one or more magnetic sources 309 may be coupled to the relevant tibia bone, the relevant femur bone, or both the relevant tibia and femur bones of the patient. As discussed above, each magnetic source 309 may be embodied as one or more magnets 450.

Figure 31:
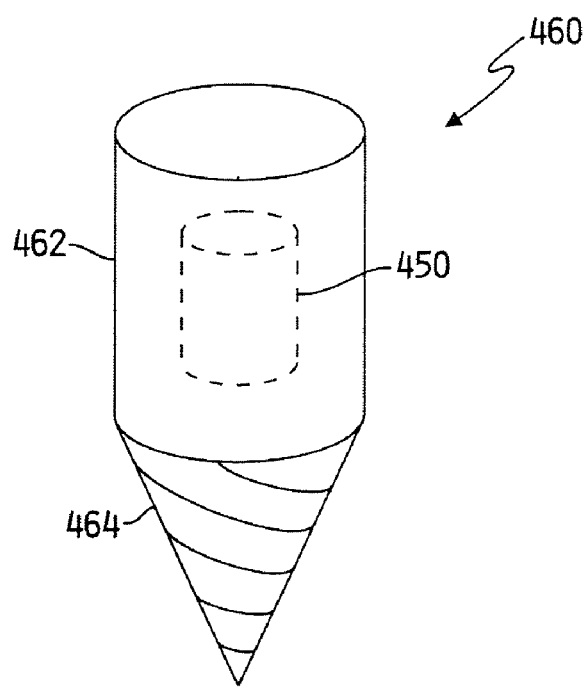
FIG. 31 is a perspective view of an implantable capsule for use with the magnetic source of FIG. 23.
Figure 32:
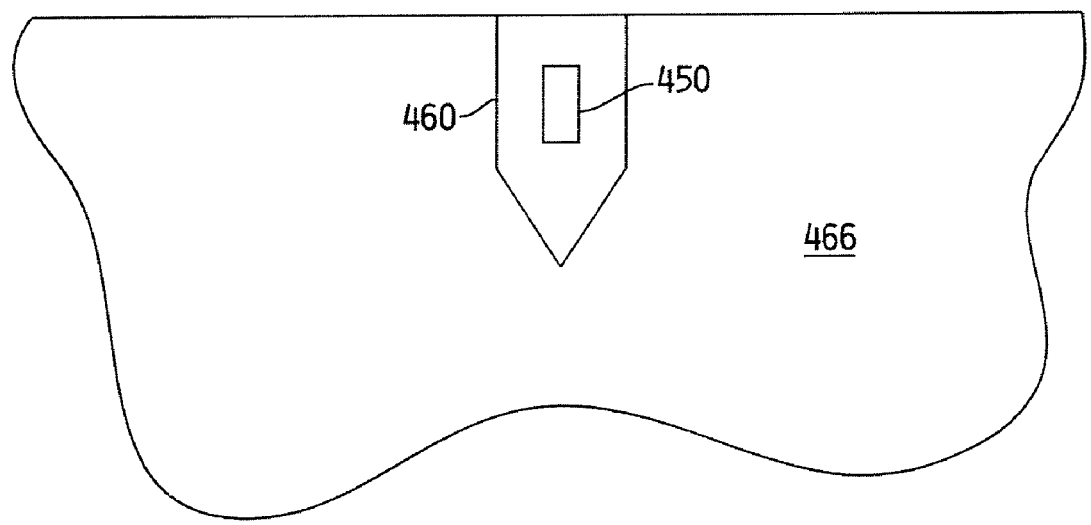
FIG. 32 is a side cross-sectional view of the implantable capsule of FIG. 31 implanted into a bone of a patient.

The magnet(s) 450 which embody the magnetic source 309 may be coupled to the bone of the patient using any suitable fixation means that secures the magnet(s) 450 to the bone such that the magnet(s) 450 do not move or otherwise propagate about before and during the performance of the orthopaedic surgical procedure. In one embodiment, the magnet(s) 450 are coupled to the bone of the patient by implanting the magnet(s) 450 in the bone. To do so, as illustrated in FIG. 31, an implantable capsule 460 may be used. The capsule 460 includes a body portion 462 in which a magnet 450 is located and a threaded screw portion 464 at a distal end of the body portion 462. The capsule 460 may be formed from any non-magnetic material, such as a plastic material, such that the magnetic field generated by the magnet 450 is not degraded by the capsule 460. As shown in FIG. 32, the capsule 460 (and the magnet 450) may be implanted in a bone 466 of the patient by first boring a suitable hole into the bone and subsequently inserting the capsule 350 by, for example, screwing the capsule 350 into the bored hole. In other embodiments, implantable capsules having other configurations may be used. For example, in some embodiments, the implantable capsule may include threads that cover the entire body of the capsule.

As discussed above in regard to FIG. 23, the position of the magnet 450 once coupled to the bone of the patient is defined by six degrees of freedom. However, because the magnetic field of the illustrative magnet 450 is circumferentially symmetric about the magnet 450, only five degrees of freedom can be determined using a single illustrative magnet 450 as the magnetic source 309. That is, the values for the three Cartesian coordinates (i.e., X-coordinate, Y-coordinate, and Z-coordinate values of FIG. 23) and two rotational values (i.e., the (theta) θ-rotational value about the X axis and the (phi) φ-rotational value about the Y axis of FIG. 23) can be determined. To provide for the determination of the sixth degree of freedom (i.e., the (psi) ψ-rotational value about the Z axis of FIG. 23), at least one additional magnet 450 may be used.

The two or more magnets 450 that form the magnetic source 309 may be coupled or implanted into the bone of the patient at any angle with respect to each other. Due to bone density inconsistencies and other factors the three angles (theta, phi, and psi) between the magnets 450 may be uncontrollable and, therefore, unknown. In such embodiments, the sixth degree of freedom of the magnetic source may be determined based on images of the bone(s) and the magnetic source 309 coupled thereto as discussed in detail below in regard to algorithm 800.

In other embodiments, the magnets 450 may be coupled or implanted into the bone of the patient at a predetermined, known position (location and/or rotation) relative to each other. For example, the two magnets 450 may be implanted into the bone of the patient such that the magnets 450 are substantially orthogonal to each other. Because the magnetic fields of the two magnets 450 have different magnetic field vectors due to the difference in orientation and because the angle between the magnets 450 is known, the six degrees of freedom of the magnetic source 309 (i.e., the two magnets 450) may be determined based on the measured five degrees of freedom of each magnet 450 and the known position of the magnets 450 relative to each other.

Regardless as to the angles of rotation defined between the magnets 450, the magnets 450 are implanted a distance apart from each other such that the magnetic fields generated by the magnets 450 do not interfere with each other. That is, the magnets 450 are separated by a sufficient distance such that the magnetic field of one magnet 450 does not constructively or destructively interfere with the magnetic field of another magnet 450. In one particular embodiment, the magnets 450 are implanted a distance of two times or more the maximum desired measuring distance (e.g, the maximum Z-axis distance from the magnets 450 that the magnetic sensor array 308 can be positioned while still accurately measuring the magnetic field of the magnets 450).

Figure 33:
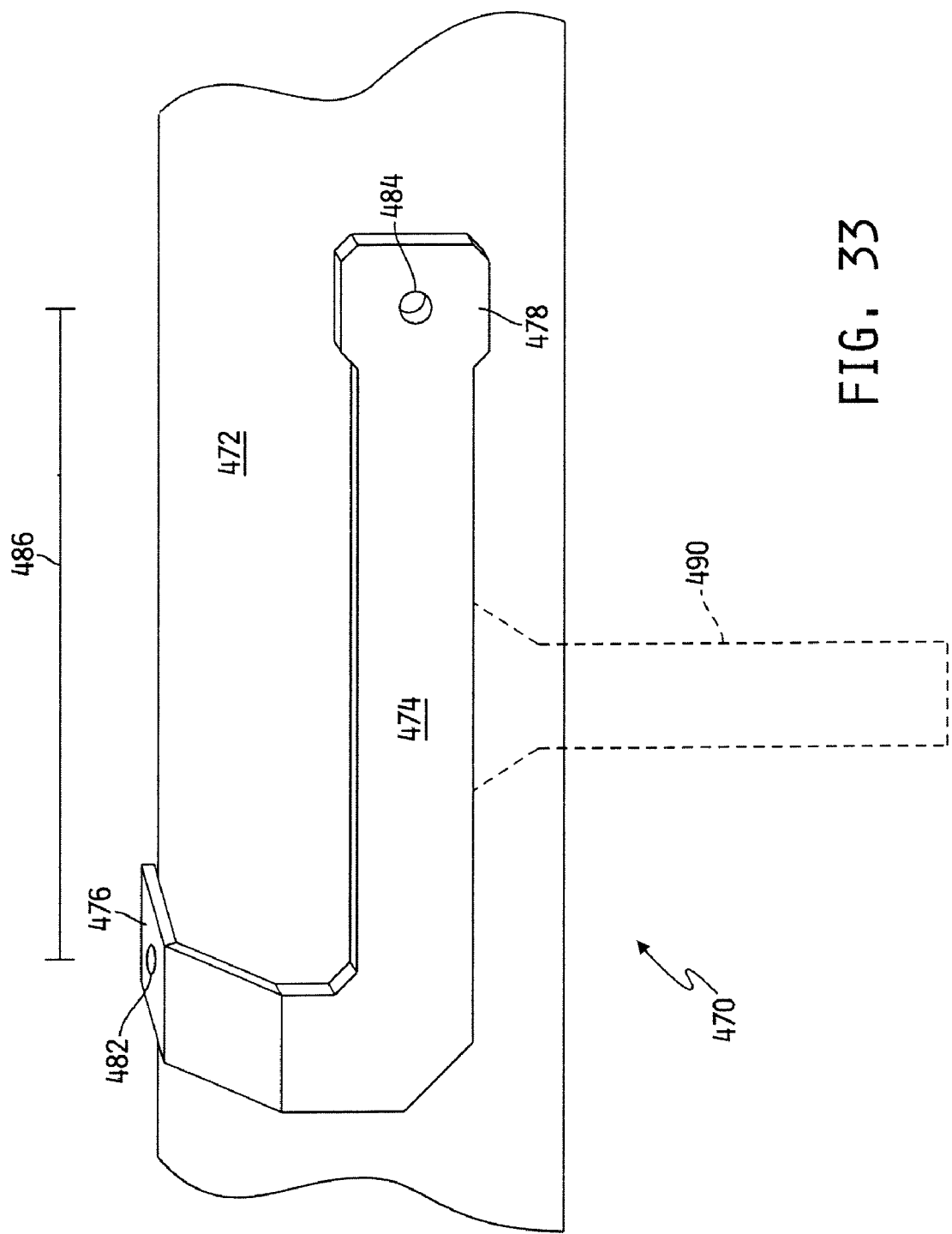
FIG. 33 is a perspective view of a jig assembly for implanting the capsule of FIG. 31.

In some embodiments, a jig or guide may be used to facilitate the implanting of two or more magnets 450 at a predetermined distance from each other (and predetermined angles of rotation relative to each other if so desired). For example, as illustrated in FIG. 33, a jig 470 may be used to facilitate the implanting of two magnets 450 into a bone 472 of the patient. The jig 470 includes a frame 474 having a first mounting pad 476 and a second mounting pad 478. The mounting pads 476, 478 are positioned at a predetermined set of rotation angles in three dimensions with respect to each ensuring the desired rotational configuration between the magnets 450. In the illustrative jig 470, the mounting pads 476, 478 are positioned substantially orthogonal to each other about only one axis of a three-dimensional coordinate system such that the magnets 450 implanted using the jig 470 will be implanted substantially orthogonal to each other about this single axis. The mounting pad 476 includes a mounting aperture 482. Similarly, the mounting pad 478 includes a mounting aperture 484. The apertures 482, 484 are separated from each other by a distance 486 equal to the desired distance of the magnets 450 once implanted into the bone 472. As such, the apertures 482, 484 may be used as guides when implanting the magnets 450 (i.e., the magnets 450 may be implanted through the apertures 482, 484) such that the magnets 450 are implanted into the bone 472 ensuring a predetermined configuration (i.e., location and orientation with respect to each other and the bone 472).

In some embodiments, the jig 470 may also include a handle 490 coupled to the frame 474 to allow the positioning of the jig 470 by the surgeon. Alternatively, the jig 470 may be secured to a rigid body such as a surgical table to reduce the likelihood that the jig 470 moves or becomes repositioned between or during the implantation of each magnet 450. Although the illustrative jig 470 is illustrated in FIG. 32 as being abutted or next to the bone 472 of the patient, it should be appreciated that in use the jig 470 may be positioned on the outside of the skin of the patient such that only incisions or punctures for the mounting holes 482, 484 need to be made. In this way, the magnets 450 may be implanted into the bone of the patient ensuring a predetermined configuration (i.e., location and orientation with respect to each other and the bone 472) with reduced surgical exposure to the patient.

In yet other embodiments, the two or more magnets 450 that form the magnetic source 309 may be secured to each other via a fixed brace or support member. The support member secures the magnets 450 at a predetermined three-dimensional position (i.e., location and orientation) with respect to each other. In such embodiments, the jig 470 may not be required. However, because the magnetic source 309 is structurally larger in such embodiments, a larger incision may be required to implant the magnetic source 309 into the bone of the patient.

In embodiments wherein the magnetic source 309 is formed from two or more magnets 450, the magnetic sensor array 308 may be used by positioning the array 308 (i.e., the sensor circuit 328) in the magnetic field of the one of the magnets 450, sensing the magnetic field of the that magnet 450 to determine position data indicative of its position relative to the magnetic sensor array 308, and then positioning the magnetic sensor array 308 in the magnetic field of the next magnet 450 relative to the magnetic sensor array 308, sensing the magnetic field of the next magnet 450, and so on.

Figure 34:
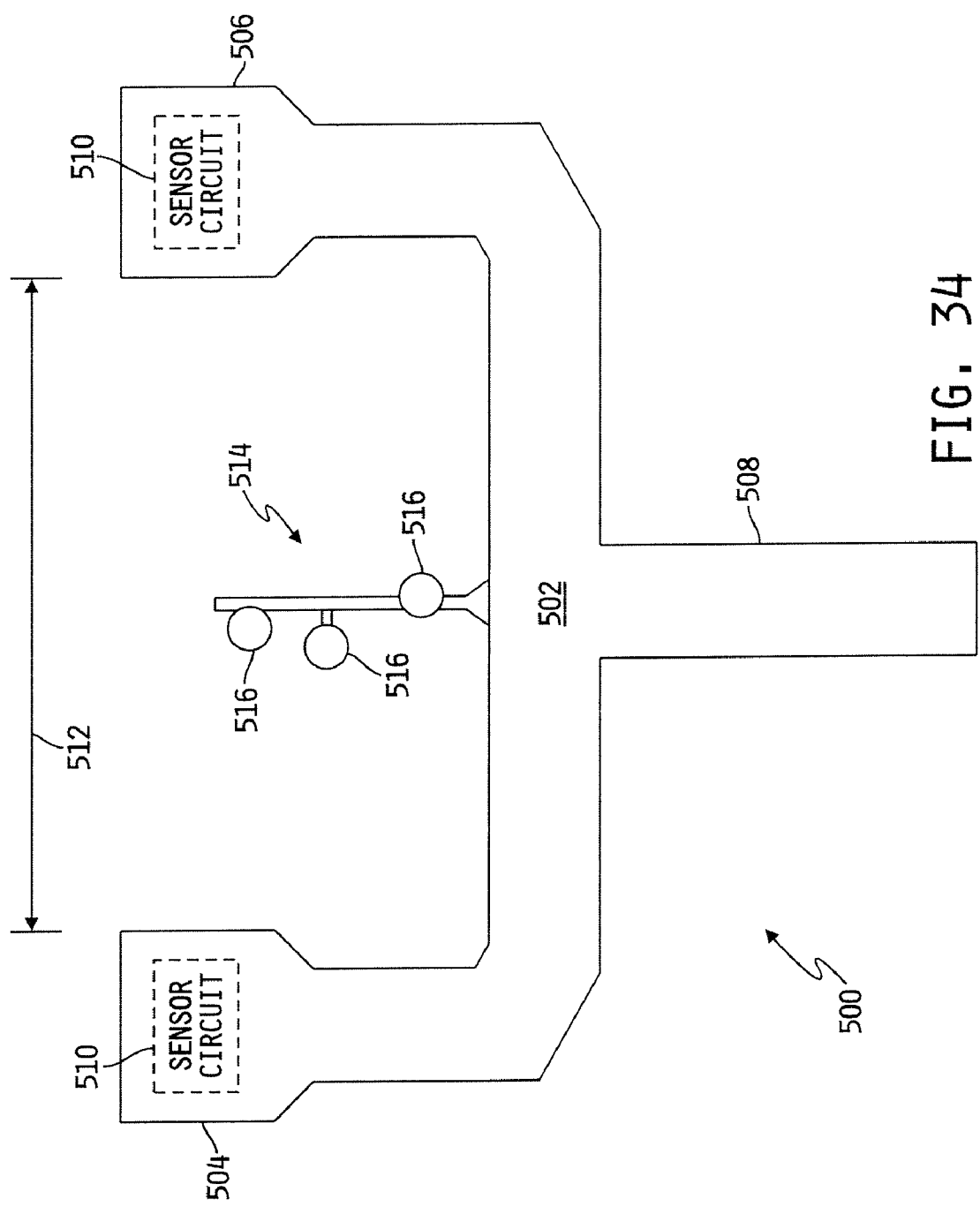
FIG. 34 is a side elevation view of another embodiment of a magnetic sensor array.

Alternatively, as illustrated in FIG. 34, a magnetic sensor array 500 may be used. The magnetic sensor array 500 includes a frame 502 and two sensing head portions 504, 506. The head portions 504, 506 are positioned a distance 512 from each other. The distance 512 is substantially equal to the distance 486 by which the magnets 450 are separated after being implanted into the bone 472 of the patient. Each sensing head portion 504, 506 includes a sensor circuit 510, which is similar to the sensor circuit 328 of the magnetic sensor 308. The magnetic sensor array 500 also includes a reflective sensor array 514, which is similar to the reflective sensor array 336 of the magnetic sensor array 308. The reflective sensor array 514 includes a number of reflective elements 516 and is used by the controller 302 to determine the relative position of the magnetic sensor array 500.

Additionally, the magnetic sensor array 500 includes a handle 508 to allow positioning of the magnetic sensor array 500. That is, a surgeon can use the handle 508 to position the magnetic sensor array 500 such that each of the head portions 504, 506, and the respective sensor circuits 510, are each positioned in a magnetic field of one of the magnets 450. Because the distance 512 between the sensing head portions 504, 506 is substantially equal to the distance 486 between the magnets 450, each of the head portions 504, 506 may be positioned in the magnetic field of one of the magnets 450 at the same time. In this way, the magnetic sensor array 500 may be used to measure the magnetic field of the two magnets 450, which embody the magnetic source 309, simultaneously or contemporaneously rather than measuring one magnetic field and then the next magnetic field as done when using the magnetic sensor array 308. In some embodiments, the sensing head portions 504, 506 may be configured to pivot with respect to the frame 502 so as to adjust the distance 512 and accommodate a variety of distances 486 between the magnets 450.

Figure 24:
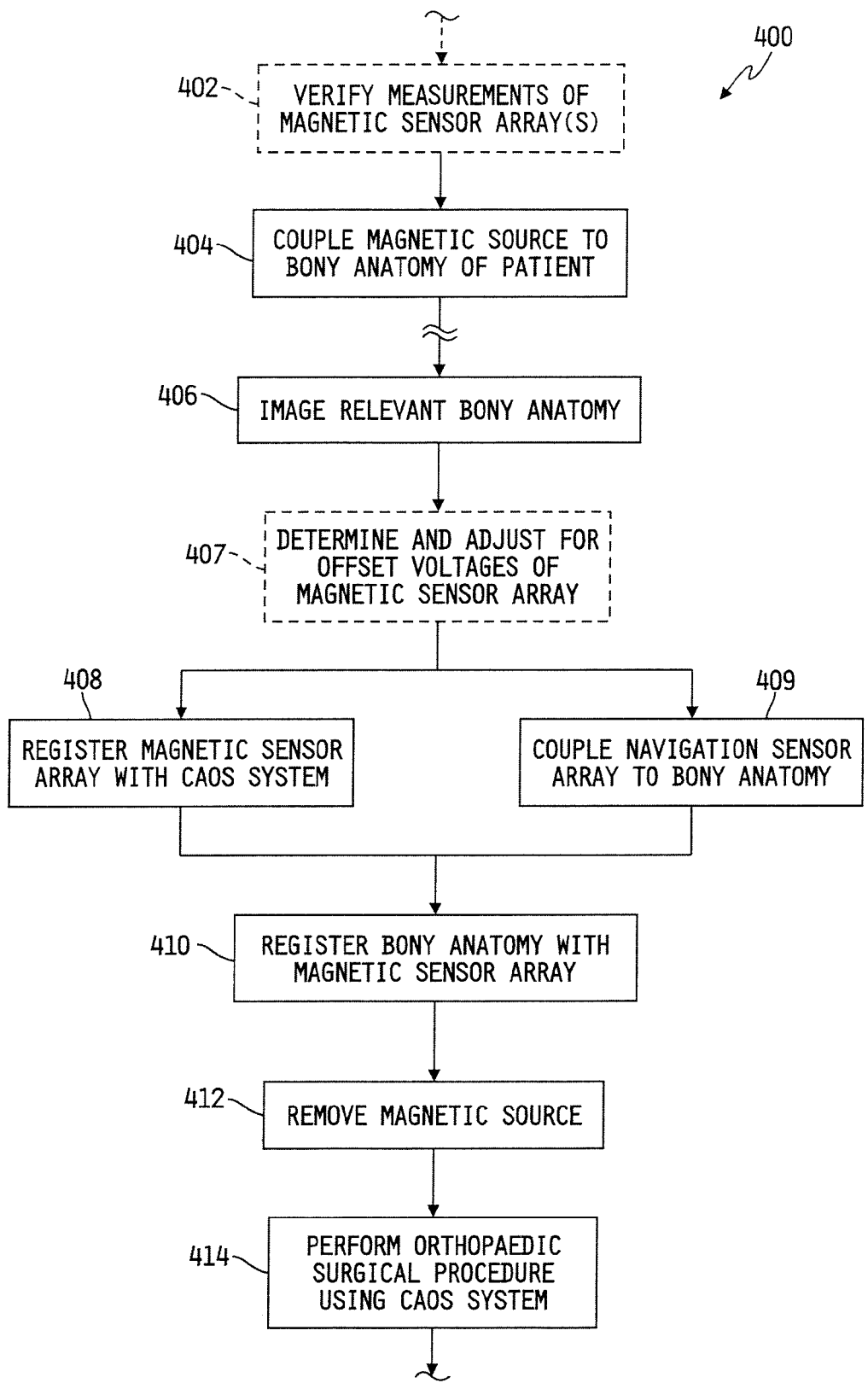
FIG. 24 is a simplified flowchart of an algorithm for registering a bone with a CAOS system.

Referring now back to FIG. 24, after the magnetic source 309 has been coupled to the bone of the patient in process step 404, an image of the bone or bones having the magnetic source 309 coupled thereto is generated in process step 406. It should be appreciated that the magnetic source 309 is coupled to the bone of the patient prior to the performance of the orthopaedic surgical procedure. As such, the magnetic source 309 may be coupled to the bone of the patient well in advance of the date or time of the orthopaedic surgical procedure or immediately preceding the procedure. Accordingly, the image of the bone or bony anatomy of the patient may be generated any time after the coupling step of process step 404. For example, the bone(s) of the patient may be imaged immediately following process step 404, at some time after the completion of process step 404, or near or immediately preceding the performance of the orthopaedic surgical procedure.

The relevant bone(s) of the patient (i.e., the bone(s) which have the magnetic source 309 coupled thereto) may be imaged using any suitable bony anatomy imaging process. The image so generated is a three-dimensional image of the relevant bone(s) of the patient and includes indicia of the magnetic source 309 coupled to the bone(s). That is, the image is generated such that the position (i.e., location and orientation) of the magnets 450 implanted or otherwise fixed to the relevant bone(s) is visible and/or determinable from the image. To do so, any image methodology capable of or usable to generate a three-dimensional image of the relevant bone(s) and magnetic source 309 may be used. For example, computed tomography (CT), fluoroscopy, and/or X-ray may be used to image the bone.

Figure 25:
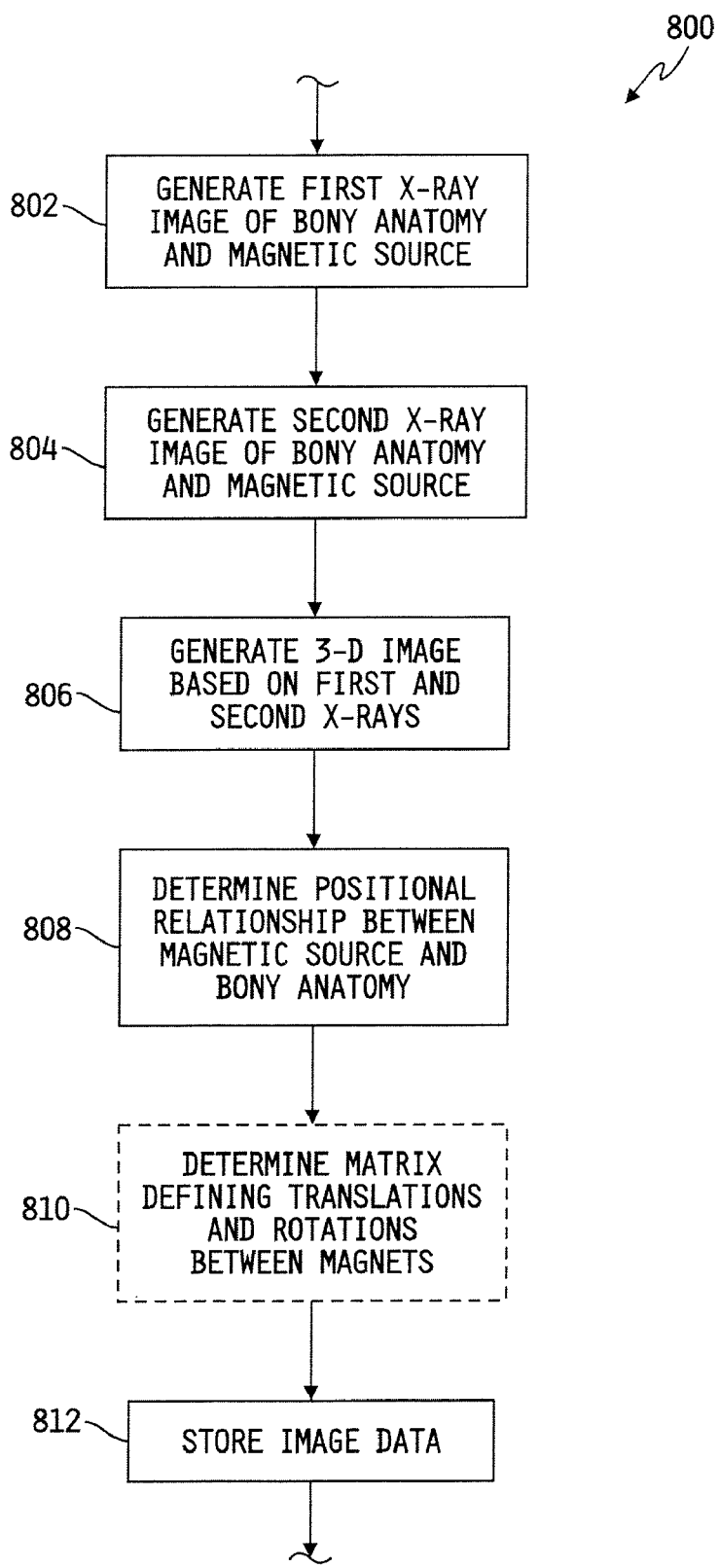
FIG. 25 is a simplified flowchart of an algorithm for generating a three-dimensional image of a bone.

In one particular embodiment, two non-coplanar X-ray images are used to form a three-dimensional image of the relevant bone(s) and magnetic source 309. To do so, as illustrated in FIG. 25, an algorithm 800 for generating an image of the relevant bony anatomy may be used. The algorithm 800 begins with process step 802 in which a first X-ray image of the relevant bony anatomy is generated. The first X-ray image includes indicia of the magnetic source 309. Next, in process step 804, a second X-ray image of the relevant bony anatomy and magnetic source 309 is generated. It should be appreciated that the first and second X-ray images are generated such that the first and second X-ray images are non-coplanar with each other.

Subsequently, in process step 806, a three-dimensional image of the relevant bone and magnetic source 309 is generated based on the first and second X-ray images. As discussed above, the first and second X-ray images are non-coplanar and may be compared with each other to determine the three-dimensional image. To do so, any two-dimensional-to-three-dimensional morphing algorithm may be used. For example, any one or combination of the morphing algorithms disclosed in U.S. Pat. Nos. 4,791,934, 5,389,101, 6,701,174, U.S. Patent Application Publication No. US2005/0027492, U.S. Patent Application Publication No. US2005/0015003A1, U.S. Patent Application Publication No. US2004/0215071, PCT Patent No. WO99/59106, European Patent No. EP1348394A1, and/or European Patent No. EP1498851A1 may be used.

Once the three-dimensional image of the relevant bone(s) and magnetic source 309 coupled thereto has been generated, data indicative of the positional relationship between the magnetic source 309 (i.e., the two or more magnets 450) and the bone(s) is determined in process step 808. To do so, a computer or computing device (such as the controller 302, a computer couple to the imaging device, or other computer or processing device) may execute an image analysis algorithm to determine, for example, the centroid and orientation of the magnets 450 forming the magnetic source 309 (i.e., the position of the magnets to five degrees of freedom) and vector data relating such centroid to the surface contours and/or fiducial points of the relevant bone(s). As such, the data indicative of the positional relationship between the magnetic source 309 and the relevant bone(s) may be embodied as a collection of vectors, scalar data, equations, or the like. As discussed below in regard to algorithm 420, such data is used by the controller 302 in conjunction with the position data received from the magnetic sensor array 309 to determine the location and orientation of the relevant bone(s).

In some embodiments, a matrix of components defining the translations and rotations relating the position of the first magnet 450 to the second magnet 450 is determined in process step 810. Typically, in such embodiments, the magnets 450 were implanted or coupled to the relevant bones without the use of a jig or the like such that the positional relationship between the magnets 450 is unknown at the time of implantation. However, in process step 810, the translation and rotation matrix may be determined based on the three-dimensional image generated in process step 806. To do so, a computer or computing device (such as the controller 302, a computer couple to the imaging device, or other computer or processing device) may be configured to determine the five degrees of freedom of each magnet 450 identified in the three-dimensional image. The five degrees of freedom of the magnets 450 may be determined in reference to any coordinate system. In one particular embodiment, the five degrees of freedom of the magnets 450 is determined in reference to a coordinate system defined by the relevant bone(s). To do so, data indicative of the positional relationship between the magnetic source 309 and the relevant bone(s) as determined in process step 808 may be used. Once the five degrees of freedom for each magnet 450 have been determined, these values are compared to determine a 1×5 matrix including the three components of the translation vector between the centroids of the magnets 450 and two angular rotations defining the spatial relationship between the two magnets 450. The matrix, therefore, defines the magnetic source 309. Once so determined, the matrix may be stored by the controller 302 in, for example, the memory device 316 or the database 318, 320. The translation/rotation matrix may be used in later computations to determine the six degrees of freedom of the magnetic source as discussed in more detail below in regard to algorithm 420.

Subsequently, in process step 812, the three-dimensional images and associated data, such as the data determined in steps 808 and 810, are stored. In one embodiment, the images and associated data are stored by the controller 302 in the memory device 316, the database 318, and/or the remote database 320 (shown in FIG. 18), which as discussed above may form a portion of the hospital network and be located apart form the computer assisted orthopaedic surgery (CAOS) system 301. In such embodiments, the controller 302 may be configured to retrieve the three-dimensional images from the remote database 320 when required for processing. In other embodiments, the three-dimensional images may be stored in a database or other storage location that is not in communication with the controller 302. In such embodiments, the three-dimensional images may be supplied to the controller 302 when required via a portable media such as a compact disk, a flash memory card, a floppy disk, or the like.

The three-dimensional images may be stored in any format that facilitates later retrieval and/or regeneration of the three-dimensional image. For example, the three-dimensional image may be stored as a collection of vector data usable to recreate the three-dimensional image. Alternatively, only particular points defining the contours of the relevant bone and the magnetic source 309 may be stored. In such embodiments, an algorithm may be used later to recreate the relevant bone(s) and magnetic source using the stored data points.

Although the illustrative algorithm 800 utilizes two non-coplanar X-ray images of the relevant bone(s) and magnetic source 309, other imaging methods may be used in other embodiments. For example, a computed tomography scan may be used to generate a three-dimensional image of the relevant bone(s) and magnetic source 309 coupled thereto. As with typical computed tomography technology, a three-dimensional image is generated from a plurality of two-dimensional images produced from the computed tomography scan. Utilizing appropriate software filters and imaging algorithms, the counters of the relevant bones, the position of the magnetic source 309, and the positional relationship between the magnetic source 309 and the relevant bone(s) may be determined based on the computed tomography, three-dimensional image in a manner similar to that used in the algorithm 800 described above.

Referring back to FIG. 24, once the relevant bony anatomy has been imaged in process step 406, errors due to the magnetic sensors 350 themselves may be determined and compensated for in process step 407. Due to manufacturing tolerances, ageing, damage, use, and other factors, the magnetic sensors 350 may generate an offset output signal (i.e., offset voltage) in the absence of a magnetic field. If the offset output signal of the magnetic sensors 350 is known, the accuracy of the magnetic sensor 308 can be improved by subtracting the offset of the magnetic sensors 350 from the measurements of the magnetic sensors 350. To do so, the magnetic sensor array 308 may be positioned in a magnetically shielded case or housing. The magnetically shielded case is configured to block a significant amount of outside magnetic fields such that the environment contained inside the case is substantially devoid of any magnetic fields. In one embodiment, the magnetically shielded case is formed from a mu-metal material such as particular nickel alloys, from ceramics, or from other materials having suitable shielding properties. To compensate for the offset voltage of the magnetic sensors 350, the magnetic sensor array 308 may be positioned in the magnetically shielded case and operated remotely, or autonomously via an error compensation software program, to measure the output signals of the magnetic sensors 350. Because there is no significant magnetic field inside the magnetically shielded case, the output signals of the magnetic sensors 350 are indicative of any offset voltage errors. Once the offset voltage errors are so determined, the accuracy of the magnetic sensor array 308 may be improved. That is, the sensor circuit 328 may be configured to subtract such offset voltages from the measurements of the magnetic sensors 350 to thereby account for the offset errors. It should be appreciated that the process step 407 may be performed any time prior to the performance of the registration of the bone or bony anatomy (see process step 410 below). In one particular embodiment, the process step 407 is executed just prior to the registration of the relevant bone(s) such that the reduced time lapse between the process step 407 and the registration process reduces the likelihood that the errors drift or change.

Subsequently, the magnetic sensor array 308, 500 is registered with the controller 302 in process step 408 and a navigation sensor array is coupled to the relevant bony anatomy in process step 409. As shown in FIG. 24, the process steps 408, 409 may be executed contemporaneously with each other or in any order. Unlike process steps 404 and 406, the process step 408 is typically performed immediately prior to the performance of the orthopaedic surgical procedure. To register the magnetic sensor array 308, 500, the array 308, 500 is positioned in the field of view 52 of the camera unit 304 such that the reflective sensor array 336, 514 is viewable by the camera unit 304. Appropriate commands are given to the controller 302 such that the controller 302 identifies the magnetic sensor array 308, 500 via the reflective sensor array 336, 514 coupled thereto. The controller 302 is then capable of determining the position of the magnetic sensor array 308, 500 using the reflective sensor array 336, 514.

In process step 409, a navigation sensor array is coupled to the relevant bone or bones of the patient. The navigation sensor array is similar to sensor array 54 illustrated in and described above in regard to FIG. 2. Similar to sensor array 54, the navigation sensor array may be a reflective sensor array similar to reflective sensor arrays 336 and 514 or may be an electromagnetic or radio frequency (RF) sensor array and embodied as, for example, a wireless transmitter. Regardless, the navigation sensor array is coupled to the relevant bony anatomy of the patient such that the navigation sensor array is within the field of view of the camera unit 304. The controller 302 utilizes the navigation sensor array to determine movement of the bony anatomy once the bony anatomy has been registered with the computer assisted orthopaedic surgery (CAOS) system 301 as discussed below in regard to process step 410.

Figure 26:
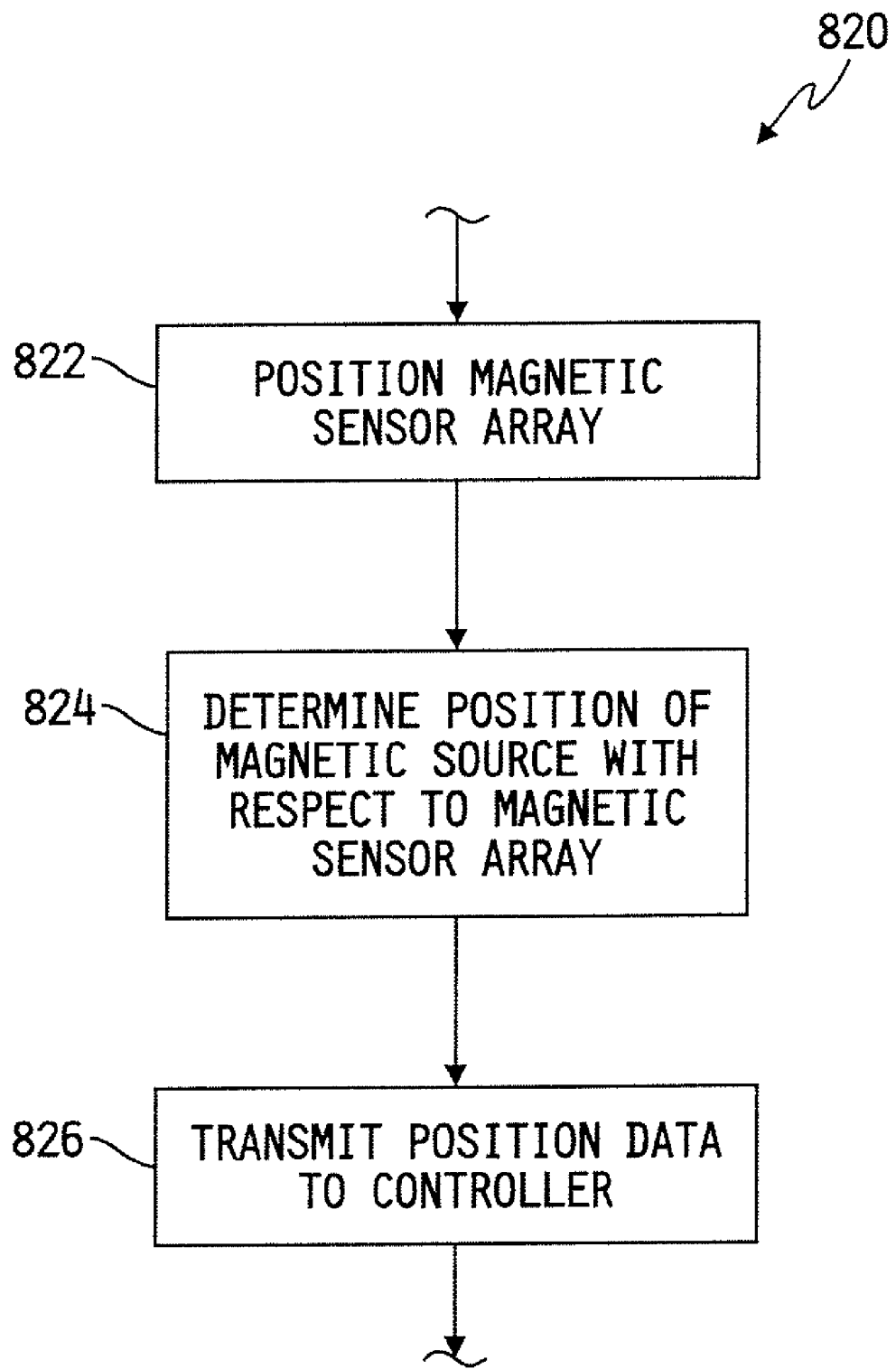
FIG. 26 is a simplified flowchart of an algorithm for operating a magnetic sensor array.

After the magnetic sensor array 308, 500 has been registered with the controller 302 in process step 408 and the navigation sensor array has been coupled to the relevant bony anatomy, the bone or bony anatomy of the patient having the magnetic source 309 coupled thereto is registered with the controller 302 in process step 410. To do so, as illustrated in FIG. 26, an algorithm 820 for operating a magnetic sensor array 308, 500 may be used. The algorithm 820 will be described below in regard to a magnetic source 309 embodied as two magnets 450 with the understanding that the algorithm 820 may be used and/or readily adapted for use with magnetic sources embodied as any number of magnetic sources.

The algorithm 820 begins with process step 822 in which the magnetic sensor array 308, 500 is positioned. If the magnetic sensor array 308 is used, the magnetic sensor array 308 is positioned in the magnetic field of the first magnet 450 in process step 822 such that the sensor circuit 328 of the magnetic sensor array 308 is positioned over a magnetic moment of the magnet 450. In one particular embodiment, the magnetic sensor array 308 may be positioned such that the central magnetic sensor $350_1$ (see FIG. 20) is substantially on-axis with the magnetic moment of the magnet 450. To do so, the sensor circuit 328 may be configured to monitor the output of the magnetic sensor $350_1$. For example, in the illustrative embodiment, the sensor circuit 328 may be configured to monitor the X-component and the Y-component outputs of the centrally located, three-dimensional magnetic sensor $350_1$. The magnetic sensor array 308 is determined to be positioned over the magnetic moment of the magnet 450 (i.e., the field sensitive point of the magnetic sensor $350_1$ is on-axis or near on-axis with the magnetic moment of the magnet 450) when the measured X-component and Y-component measurements are at a minimum value (or below a threshold value).

In other embodiments, sensor circuit 328 may be configured to monitor the X-component and the Y-component outputs of additional magnetic sensors 350. For example, the sensor circuit 328 may be configured to monitor the output of all magnetic sensors 350 configured to measure the X-component of the three-dimensional magnetic flux density of the magnet 450 at a given position (e.g., magnetic sensors $350_1$-$350_5$, $350_{15}$, and $350_{17}$) and the output of all the magnetic sensors 350 configured to measure the Y-component of a three-dimensional magnetic flux density of the magnet 450 at a given position (i.e., magnetic sensors $350_1$-$350_5$, $350_{14}$, and $350_{16}$). For example, the sensor circuit 328 may be configured to sum the output of such sensors and determine the location at which such sums are at a minimum value.

To assist the surgeon in positioning the magnetic sensor array 308, the sensor circuit 328 may be configured to provide feedback to the surgeon via the indicator 360. For example, when the sensor circuit 328 determines that the sum of the X-component measurements and the sum of the Y-component measurements have reached minimum values, the sensor circuit 328 may be configured to activate the indicator 360. In this way, the surgeon knows when the magnetic sensor array is properly positioned in the X-Y plane relative to the magnet 450.

In other embodiments, the sensor circuit 328 may be configured to adapt to non-alignment of the magnetic sensor array 308. For example, based on the X-component and Y-component measurement outputs of the magnetic sensors $350_1$-$350_5$ and $350_{14}$-$350_{17}$, the sensor circuit 328 may be configured to determine which magnetic sensor 350 is on-axis or closest to on-axis with the magnetic moment of the magnet 450. For example, if the X-component and Y-component measurement outputs of the magnetic sensor $350_5$ (see FIG. 20) is near zero or at a minimum, the sensor circuit 328 may be determine that the field sensitive point of the magnetic sensor $350_5$ is on-axis or near on-axis with the magnetic moment of the magnet 450. Rather than forcing the surgeon or user to reposition the magnetic sensor 308, the sensor circuit 328 may be configured to adjust measurement values of the magnetic sensors 350 for the X-Y offset of the magnetic moment of the magnet 450 relative to the sensor board 370.

In process step 822, the magnetic sensor array 308 is also positioned along the Z-axis relative to the magnet 450. That is, the magnetic sensor array 308 is positioned a distance away from the magnet 450 along the Z-axis as defined by the magnetic moment of the magnet 450. The magnetic sensor array 308 is position at least a minimum distance away from the magnet 450 such that the magnetic sensors 350 do not become saturated. Additionally, the magnetic sensor array 308 is positioned within a maximum distance from the magnet 450 such that the measured magnetic flux density is above the noise floor of the magnetic sensors 350 (i.e., the magnetic flux density if sufficient to be discerned by the magnetic sensors 350 from background magnetic "noise"). The sensor circuit 328 may be configured to monitor the output of the magnetic sensors 350 to determine whether the magnetic sensors 350 are saturated or if the output of the magnetic sensors 350 is below the noise floor of the sensors 350. The sensor circuit 328 may be configured to alert the surgeon or user of the magnetic sensor array 308 if the magnetic sensor array 308 is properly positioned with respect to the Z-axis relative to the magnet 450. As discussed above in regard to process step 404 of algorithm 400, the maximum distance at which the magnetic sensor array 308 will be used also determines the minimum distance between the individual magnets 450 that form the magnetic source 309 (i.e., the magnets 450 are separated by a distance of two times or more the maximum measurement distance of the magnetic sensor array 308 in one embodiment).

Alternatively, the magnetic sensor array 500 may be used to register the bone(s) of the patient by positioning the array 500 such that each of the sensing heads 504, 506 (and sensor circuits 510) is positioned in a magnetic field of one of the magnets 450. That is, the magnetic sensor array 500 is positioned such that each sensor circuit 510 is on-axis with the magnetic moment of the respective magnet 450. As discussed above in regard to the magnetic sensor array 308, each of sensing heads 504, 506 may be positioned such that a central magnetic sensor $350_1$ is substantially on axis with the magnetic moment of each magnet 450. To do so, each sensor circuit 510 may be configured to monitor the X-component and Y-component measurement outputs of the respective magnetic sensor $350_1$ and determine when such measurements are at a minimum magnitude or below a predetermined threshold. Alternatively, as discussed above in regard to the magnetic sensor array 308, the sensor circuits 510 may be configured to adapt to non-alignment of the sensor circuits 510 with respect to the magnets 450 by determining which individual magnetic sensor 350 is on-axis or closest to on-axis with the magnetic moments of the magnets 450 and adjusting the magnetic field measurements of the remaining magnetic sensors 350 accordingly. Further, similar to magnetic sensor array 308, the sensor circuits 510 of the magnetic sensor array 500 may be configured to determine when the magnetic sensor array 500 is properly positioned in the Z-axis with respect to the magnets 450. That is, the sensor circuits 510 may be configured to monitor the output of the magnetic sensors 350 to determine whether the magnetic sensors 350 are saturated or if the output of the magnetic sensors 350 are below the noise floor of the sensors and determine if the magnetic sensor array 500 is properly positioned based thereon.

Figure 27:
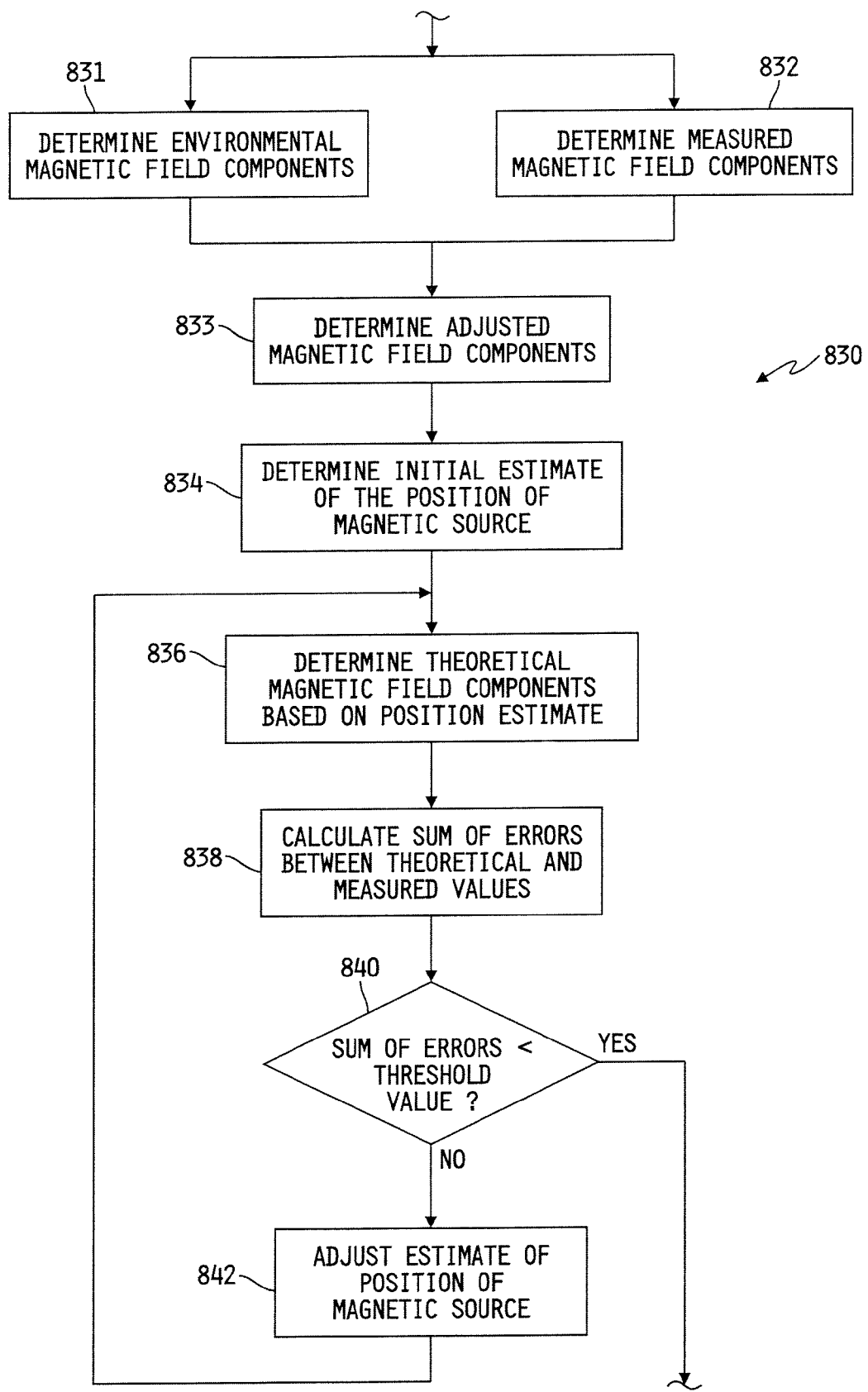
FIG. 27 is a simplified flowchart of an algorithm for determining a position of a magnetic source.

Once the magnetic sensor array 308, 500 has been properly positioned, the position of the magnetic source 309 (i.e., the magnets 450) with respect to the magnetic sensor array 308, 500 is determined in process step 824. To do so, the magnetic sensor array 308, 500 (i.e., sensor circuits 328, 510) may execute an algorithm 830 for determining a position of a magnetic source as illustrated in FIG. 27.

The algorithm 830 begins with process steps 831 and 832. As illustrated in FIG. 27, the process steps 831 and 832 may be executed contemporaneously with each other or in any order. In process step 831, undesirable environmental magnetic fields which may cause errors in the measurements of the magnetic sensors 350 are measured. The accuracy of the measurements of the magnetic sensors 350 may be improved by compensating the magnetic sensor array 308 for these undesirable, adverse factors. The environmental magnetic fields which are measured in process step 831 may include the Earth's magnetic field and magnetic fields generated from other equipment located in the surgical room, electrical cables, iron constructions, vehicles, and other stray or undesirable magnetic fields generated by sources other than the magnetic source 309 which may interfere with the magnetic fields generated by the magnetic source 309. For example, the Earth's magnetic field may adversely affect the measurements of the magnetic sensors 350 by interfering (i.e., constructively or destructively) with the magnetic field generated by the magnetic source 309. Because the Earth's magnetic field is continuously changing, a fixed adjustment value or offset for the magnetic sensors 350 is not available. However, as discussed above in regard to FIGS. 21 and 22, by using a remote magnetic sensor 386, the effects of the Earth's magnetic field can be accounted for. That is, because the remote magnetic sensor 386 is located apart from the sensor circuit 328 of the magnetic sensor array 308, the magnetic field generated by the magnetic source 309 has minimal impact on the measurements of the remote magnetic sensor 386. As such, the measurements of the remote magnetic sensor 386 are generated primarily in response to the Earth's magnetic field and other environmental magnetic fields such as those caused by other surgical equipment located in the operating room and the like. Therefore, in process step 831, the measurements of the remote magnetic sensor 386 are sampled.

In process step 832, the components of the three-dimensional magnetic flux density of the magnet 450 at various positions is measured. To do so, the output of each of the magnetic sensors 350 is sampled. As discussed above in regard to FIG. 20, some of the magnetic sensors 350 are three-dimensional magnetic sensors and, as such, measure the magnitude of each component at a given position of the magnetic flux density of the magnet 450. Other magnetic sensors 350 are one-dimensional magnetic sensors and are configured to measure the magnitude of only one component of the magnetic flux density. In the illustrative embodiment of FIG. 20, a total of twenty seven component measurements are generated by the magnetic sensors 350 (i.e., five three-dimensional magnetic sensors and twelve one-dimensional magnetic sensors). The magnetic field measurements may be stored in a suitable memory device for subsequent processing as described below. The sampling rate of the magnetic sensors 350 may be of rate useable or sustainable by the processing circuit 352

Contemporaneously with or during predetermined periods of the measurement process of the magnetic sensors 350 (e.g., during the positioning of the magnetic sensor array 308 in process step 822 of the algorithm 820 or during the process step 832 of algorithm 830), the sensor circuit 328 may be configured to perform a number of test procedures. To do so, the sensor circuit 328 may include one or more test circuits configured to perform one or more test algorithms. For example, the test circuits may be configured to measure the supply voltage of the sensor circuit 328 and produce an error if the supply voltage is below a predetermined minimum threshold or above a predetermined maximum threshold. Additionally, the sensor circuit 328 may be configured to monitor the output of the magnetic sensors 350 and produce an error (e.g., activate an indicator to alert the user of the magnetic sensor array 308) if the voltage levels of the output signals of the sensors 350 are above a predetermined maximum threshold (i.e., the magnetic sensors 350 are in saturation) or below a predetermined minimum threshold (i.e., below the noise floor of the magnetic sensors 350). Additionally, in some embodiments, the sensor circuit 328 may include one or more compensation circuits to compensate or adjust the measurement values of the magnetic sensors 350 for such factors as temperature or the like.

Subsequently, in process step 833, the measurements of the magnetic sensors 350 are compensated or adjusted for the undesirable environmental magnetic fields. To do so, in one embodiment, the measurements of the magnetic sensors 350 are adjusted by subtracting the measurements of the remote magnetic sensor 386. In this way, the magnetic field errors caused by the Earth's magnetic field and other environmental magnetic fields are adjusted out of the measurement data produced by the magnetic sensors 350 and the overall accuracy of the magnetic sensor array 308 in measuring the magnetic flux density generated primarily from the magnetic source 309 is improved.

In process step 834, an initial estimate of the position of the magnet 450 is determined. The initial estimate includes an estimate of the values of the five degrees of freedom of the magnet 450. That is, the initial estimate includes an X-coordinate value, a Y-coordinate value, a Z-coordinate value, a (theta) θ-rotational value about the X-axis, and a (phi) φ-rotational value about the Y-axis of the magnet 450. In one particular embodiment, the X-, Y-, and Z-coordinate values are the coordinate values of the particular magnetic sensor 350 with respect to the centroid of the magnet 450. That is, the X-, Y-, and Z-coordinate values are estimates of the position of the magnetic sensor 350 in a three-dimensional coordinate system wherein the centroid of the magnet 450 is defined as the center of the coordinate system (i.e., the centroid of the magnet 450 lies at point (0, 0, 0)). Estimating the location of the magnet 450 in this manner allows calculations of the magnetic flux density using positive values for the X-, Y-, and Z-coordinate estimated values.

The estimated values may be any values and, in some embodiments, are predetermined seeded values that are used for measurement processes. However, by selecting an initial estimate closer to the actual position of the magnet 450, the speed and accuracy of the algorithm 830 may be improved. To do so, knowledge of the position of the magnetic sensor array 308, 500 with respect to the magnet 450 may be used. That is, as discussed above in process step 822 of algorithm 820, the magnetic sensor arrays 308, 500 are positioned such that the arrays 308, 500 are on-axis or near on-axis with the magnetic moment of the magnet 405. As such, in one embodiment, the initial estimate of the location of the magnet 405 with respect to the magnetic sensor array 308, 500 includes an estimated X-coordinate value of zero and an estimate Y-coordinate value of zero. Additionally, the (theta) θ-rotational value and the a (phi) φ-rotational value of the magnet 450 may be estimated as zero (e.g., it may be assumed that the sensor board 370 of the magnetic sensor array 308, 500 is positioned orthogonal to the longitudinal axis of the magnet 405). The Z-coordinate value may also be estimated at zero. However, for additional accuracy, the Z-coordinate value may be estimated based on the average magnetic flux density of the Z-vector of the magnetic flux density of the magnet 450 as measured by the magnetic sensors 350 (i.e., those magnetic sensors 350 configured to measure the Z-vector of the three-dimensional magnetic field of the magnet 450). However, other estimated values may be used in other embodiments.

Once the initial estimated position of the magnet 450 is determined in process step 834, the components of the theoretical three-dimensional magnetic flux density of the magnet 450 at various points in space are calculated in process step 836. During the first iteration of the algorithm 830, the five degrees of freedom values of the magnet 450 estimated in process step 834 are used to determine each component of the theoretical three-dimensional magnetic flux density. However, as discussed below in regard to process step 842, in subsequent iterations of the algorithm 830, revised estimated values of the five degrees of freedom of the magnet 450 are used in process step 836.

The theoretical three-dimensional magnetic flux density of the magnet 450 at each sensor's 350 position at a point in space about the magnet 450 may be calculated using any suitable equation (s) and/or algorithms. In one particular embodiment, the following equations are used to calculate the magnitude of the magnetic flux density components (i.e., the X-, Y-, and Z-components) of the magnet 450.

$$B_x = \frac{\mu m \left[ \frac{3x \left( x\sin(\Theta)\cos(\Phi) + y\sin(\Theta)\sin(\Phi) + z\cos(\Theta) \right)}{r^2} - \sin(\Theta)\cos(\Phi) \right]}{4\pi r^3}$$

$$B_y = \frac{\mu m \left[ \frac{3y \left( x\sin(\Theta)\cos(\Phi) + y\sin(\Theta)\sin(\Phi) + z\cos(\Theta) \right)}{r^2} - \sin(\Theta)\sin(\Phi) \right]}{4\pi r^3}$$

$$B_z = \frac{\mu m \left[ \frac{3z \left( x\sin(\Theta)\cos(\Phi) + y\sin(\Theta)\sin(\Phi) + z\cos(\Theta) \right)}{r^2} - \cos(\Phi) \right]}{4\pi r^3}$$

wherein μ is the permeability of free space (i.e., about $4*\pi*10^{-17}$ WbA$^{-1}$m$^{-1}$), m is the magnitude of the magnetic moment of the magnet 450 in units of Am$^2$, and $r=\sqrt{x^2+y^2+z^2}$ (in distance units).

Once the theoretical magnetic flux densities are calculated in process step 836, the sum of the error between the theoretical magnetic flux density component values and the measured magnetic flux density values as determined in process step 832 is calculated in process step 838. That is, the difference between the theoretical magnetic flux density component values and the measured magnetic flux density component values for each magnetic sensor 350 is calculated. The calculated differences for each magnetic sensor 350 is then summed. To do so, in one particular embodiment, the following objective function may be used.

$$F = \sum_{i=0}^{n} w_i (B_{th_i} - B_{me_i})^2$$

wherein n is the number of magnetic flux density components measured, $B_{th}$ is the theoretical magnitude of the ith magnetic flux density component of the magnet 450 at a given sensor position, $B_{me}$ is the measured magnitude of the ith magnetic flux density component of the magnet 450 at a given position, and $w_i$ is a weighting factor for the ith magnetic flux density component. The weighting factor, $w_i$, may be used to emphasize or minimize the effect of certain magnetic sensors 350. For example, in some embodiments, the magnetic sensors 350 positioned toward the center of the sensor board 370 may be given a higher weighting factor than the magnetic sensors 350 positioned toward the perimeter of the sensor board 370. In one particular embodiment, the weighting factors, $w_i$, are normalized weighting factors (i.e., range from a value of 0 to a value of 1). Additionally, other weighting schemes may be used. For example, each weighting factors, $w_i$, may be based on the magnetic field sensitivity of the particular magnetic sensor 350 measuring the ith magnetic flux density component. Alternatively, the weighting factors, $w_i$, may be based on the standard deviation divided by the mean of a predetermined number of samples for each magnetic sensor 350. In other embodiments, the weighting factors, $w_i$, may be used to selectively ignore sensors that are saturated or under the noise floor of the magnetic sensor 350. Still further, a combination of these weighting schemes may be used in some embodiments.

In process step 840, the algorithm 830 determines if the value of the objective function determined in process step 838 is below a predetermined threshold value. The predetermined threshold value is selected such that once the objective function falls below the threshold value, the position of the magnetic source 309 (i.e., the magnet 450) with respect to the magnet sensor array 308, 500 is known within an acceptable tolerance level. In one particular embodiment, the predetermined threshold value is 0.0. However, to increase the speed of convergence of the algorithm 830 on or below the predetermined threshold value, threshold values greater than 0.0 may be used in other embodiments.

If the objective function (i.e., the sum of errors) is determined to be below the predetermined threshold value, the algorithm 830 completes execution. However, if the objective function is determined to be greater than the predetermined threshold value in process step 840, the algorithm advances to process step 842. In process step 842, the estimate of the position of the magnetic source is adjusted. That is, in the first iteration of the algorithm 830, the initial estimate for the X-coordinate value, the Y-coordinate value, the Z-coordinate value, the (theta) θ-rotational value about the X axis, and the (phi) φ-rotational value about the Y axis of the magnet 450 are adjusted. A local optimization algorithm or a global optimization algorithm may be used. Any suitable local or global optimization algorithm may be used.

Once a new estimate for the position of the magnet 460 (in five degrees of freedom) has been determined, the algorithm 830 loops back to process step 836 in which the theoretical magnetic flux density component values are determined using the new estimates calculated in process step 842. In this way, the algorithm 830 performs an iterative loop using the local/global optimization algorithm until the objective function converges to or below the predetermined threshold value. As discussed above, once the objective function has so converged, the five degrees of freedom of the magnet 450 is known.

It should be appreciated that in some embodiments the algorithm 800 is executed solely by the magnetic sensor array 308, 500. However, in other embodiments, the magnetic sensor arrays 308, 500 may be configured only to measure the magnetic flux density components of the magnet 450 in process step 832. In such embodiments, the process steps 834-842 are executed by the controller 302. To do so, the sensor circuits 328, 510 of the magnetic sensor arrays 308, 500 are configured to transmit the magnetic field measurement values of each magnetic sensor 350 to the controller 302.

Referring now back FIG. 26, once the position (i.e., the five degrees of freedom) of each magnet 450 of the magnetic source 309 has been determined in process steps 822 and 824, the position data indicative of the five degrees of freedom of the magnetic source 309 (i.e., the magnets 450) is transmitted to the controller 302 in process step 826. The position data may be embodied as any type of data capable of representing the determined five degrees of freedom (i.e., the magnitude of the X-coordinate value, the Y-coordinate value, the Z-coordinate value, the (theta) θ-rotational value, and the (phi) φ-rotational value of the magnet(s) 450).

In response to the position data received by the magnetic sensor array 308, 500, the controller 302 determines the position (i.e., the six degrees of freedom) of the relevant bony anatomy of the patient. To do so, the controller 302 may execute an algorithm 420 as illustrated in FIG. 28. The algorithm 420 may be embodied as software or firmware stored in, for example, the memory device 316. The algorithm 420 begins with process steps 422 and 426. As shown in FIG. 28, the process steps 422, 426 may be executed contemporaneously with each other or in any order.

In process step 422, the controller 302 receives the position data from the magnetic sensor array 308, 500 via the communication link 326. As discussed above, the position data is indicative of the position of the magnetic source 309 (i.e., the magnets 450) relative to the magnetic sensor array 308, 500. In the illustrative embodiment, the position data is embodied as coefficient values that define the five degrees of freedom (i.e., X-coordinate, Y-coordinate, Z-coordinate, (theta) θ-rotational, and (phi) φ-rotational values) of the magnetic source 309. Once the position data is received from the magnetic sensor array 308, 500, the controller 302 may store the position data in the memory device 316.

In process step 424, the controller 302 determines the position of the magnetic sensor array 308, 500. To do so, the controller 302 receives images from the camera unit 304 via the communication link 310. By analyzing the position of the reflective sensor array 336, 514 in the images, the controller 302 determines the position of the associated magnetic sensor array 308, 500 relative to the computer assisted orthopaedic surgery (CAOS) system 301 (e.g., relative to the camera 304 and/or the controller 302).

Subsequently, in process step 426, the controller 302 determines the position (i.e., to five degrees of freedom) of the magnetic source 309 with respect to the computer assisted orthopaedic surgery (CAOS) system 301. To do so, the controller 302 uses the position data indicative of the five degrees of freedom of the magnetic source 309 relative to the magnetic sensor array 308, 500 and the position of the magnetic sensor array 308, 500 relative to the computer assisted orthopaedic surgery (CAOS) system 301 as determined in process step 424. That is, because the controller 302 has determined the position of the magnetic sensor array 308, 500 within the coordinate system of the computer assisted orthopaedic surgery (CAOS) system 301 and the magnetic sensor array 308, 500 has determined the position of the magnetic source 309 relative to the array 308, 500 itself, the controller 302 can determine the position of the magnetic source 309 in the coordinate system of the computer assisted orthopaedic surgery (CAOS) system 301 (i.e., with respect to the CAOS system 301) by combining the two forms of position data an appropriate algorithm (e.g., a vector addition algorithm).

However, because the magnetic sensor array 308, 500 has determined only the five degrees of freedom of the magnetic source 309 (i.e., each of the magnet(s) 450 that embody the magnetic source 309), the controller 302 is configured to determine the sixth degree. In furtherance thereof, in process step 428, the controller 302 retrieves the three-dimensional image(s) of the bony anatomy that was generated in process step 406 of the algorithm 400. As discussed above in regard to the process step 406, the controller 302 may retrieve the image from the database 318 and/or from the remote database 320. The image may be so retrieved based on any suitable criteria. For example, in one embodiment, the image is retrieved based on patient identification data. In such embodiments, the patient identification data may be supplied to the controller 302 prior to the performance of the orthopaedic surgical procedure. The controller may also retrieve any number of generated images. The generated images include indicia or images of the magnetic source 309 (i.e., the two magnets 450) and its position with respect to the bony anatomy.

In process step 430, the controller 302 creates a graphically rendered image of the bony anatomy having a location and orientation based on the position of the magnetic source 309 determined in process step 426 and surface contours based on the image(s) of the bone(s) retrieved in process step 428.

However, as discussed above, because only five degrees of freedom of the magnetic source 309 were determined and transmitted to the controller 302 in algorithm 820, the controller 302 must determine (or retrieve) the sixth degree of freedom of the magnetic source 309. In some embodiments, the sixth degree of freedom is already determined or known by the controller 302. For example, in embodiments wherein the magnets 450 are implanted into the relevant bone(s) at a predetermined angle with respect to each other, such predetermined angle may be supplied to the controller 302 as the sixth degree of freedom. Alternatively, in embodiments wherein the three dimensional image(s) of the relevant bony anatomy and magnetic source 309 is determined using algorithm 800 described above in regard to FIG. 25, the matrix locating the magnets 450 with respect to each other may have been determined in process step 810.

However, in some embodiments, the controller 302 may be configured to determine the matrix locating the magnets 450 with respect to each other in process step 430. To do so, the controller 302 may execute an algorithm 850 for determining the sixth degree of freedom of the magnets 450 as illustrated in FIG. 29. The algorithm 850 begins with process step 852 in which the controller 302 determines the position of a first one of the magnets 450. The position of the magnet 450 is defined by the five degrees of freedom of the magnet 450. The five degrees of the freedom of the first magnet 450 with respect to the computer assisted orthopaedic (CAOS) system 301 has been determined previously by the controller 302 in process step 426. As such, if value(s) defining the five degrees of freedom were stored by the controller 302, such value(s) are retrieved by the controller 302 in process step 852. Next, in process step 854, the controller 302 determines the position of a second one of the magnets 450. Again, the controller 302 has already determined the five degrees of freedom of the second magnet 450 in process step 426 and, if stored, retrieves the values indicative thereof in process step 854.

Subsequently, in process step 856, the controller 302 is configured to mathematically rotate the three-dimensional image retrieved in process step 428 of algorithm 420. The three-dimensional image is rotated about the fixed position of the first magnet 450 until the position of the second magnet 450 is equal to the initial position, as determined in step 854, of the second magnet 450. In process step 858, the controller 302 determines the sixth degree of freedom based on the amount of rotation required. It should be appreciated that the three-dimensional image may be rotated about all three orthogonal axes to determine the sixth degree of freedom.

Once the six degrees of freedom of the magnetic source 309 have been determined, the rendered image of the bony anatomy may be generated in process step 430 based on the six degrees of freedom of the magnetic source 309 and the data indicative of the positional relationship between the magnetic source and the bony anatomy as determined in process step 808. That is, because the six degrees of freedom of the magnetic source 309 are known and the positional relationship between the bony anatomy and the magnetic source 309 is known, the six degrees of freedom of the bony anatomy may be determined. The rendered image may be displayed to the surgeon or other user of the system 300 on the display device 306 using the communication link 312.

Referring back to algorithm 400 in FIG. 24, after the bony anatomy has been registered in process step 410, the magnetic source 309 may be decoupled from the bone(s) of the patient in process step 412. To do so, the magnetic sensor array 308, 500 may be used to determine the location of the magnets 450 which form the magnetic source 309. For example, the magnetic sensor array 308, 500 may be passed over the skin of the patient until the indicator 360 of the magnetic sensor array 308, 500 is activated, which indicates the magnetic sensor array 308, 500 is in the magnetic field of at least one of the magnets 450. The magnets 450 may then be removed using an appropriate surgical procedure. In this way, the magnetic fields of the magnets 450 are prevented from interfering with the performance of the orthopaedic surgical procedure. For example, in embodiments wherein the navigation sensor arrays are embodied as wireless transmitters (i.e., electromagnetic sensor arrays) rather than reflective sensor arrays, the magnetic source 309 may be decoupled from the bone(s) of the patient prior to the performance of the orthopaedic surgical procedure so as to avoid any magnetic interference with the operation. of the sensor arrays 54. Alternatively, if the magnetic source 309 is left coupled to the bone(s) of the patient during the performance of the orthopaedic surgical procedure, the bone(s) may be reregistered at any time and as often as necessary during the procedure.

Subsequently, in process step 414, the orthopaedic surgical procedure may be performed. The orthopaedic surgical procedure is performed using the images of the relevant bony anatomy, which are displayed on the display device 306 in a position and orientation based on the visual data received from the navigation sensor array coupled to the bony anatomy, the relative orientation and position with respect to the navigation sensor array being determined based on the position data received from the magnetic sensor array 308, 500, and the generated images of the bony anatomy having indicia of the position of the magnetic source 309 coupled therewith. The surgeon may use the system 300 to navigate and step through the orthopaedic surgical process in a similar manner as the CAOS system 10 illustrated in and described above in regard to FIGS. 1-17. For example, navigation with respect to the bony anatomy may be facilitated by the use of a reflective sensor array, such as one similar to the tibial array 60 of FIG. 3, coupled to the bony anatomy. It should be appreciated, however, that the present algorithm 400 for registering the bone anatomy of a patient may completely or partially replace the process step 106 of the algorithm 100 illustrated in and described above in regard to FIG. 6.

Figure 35:
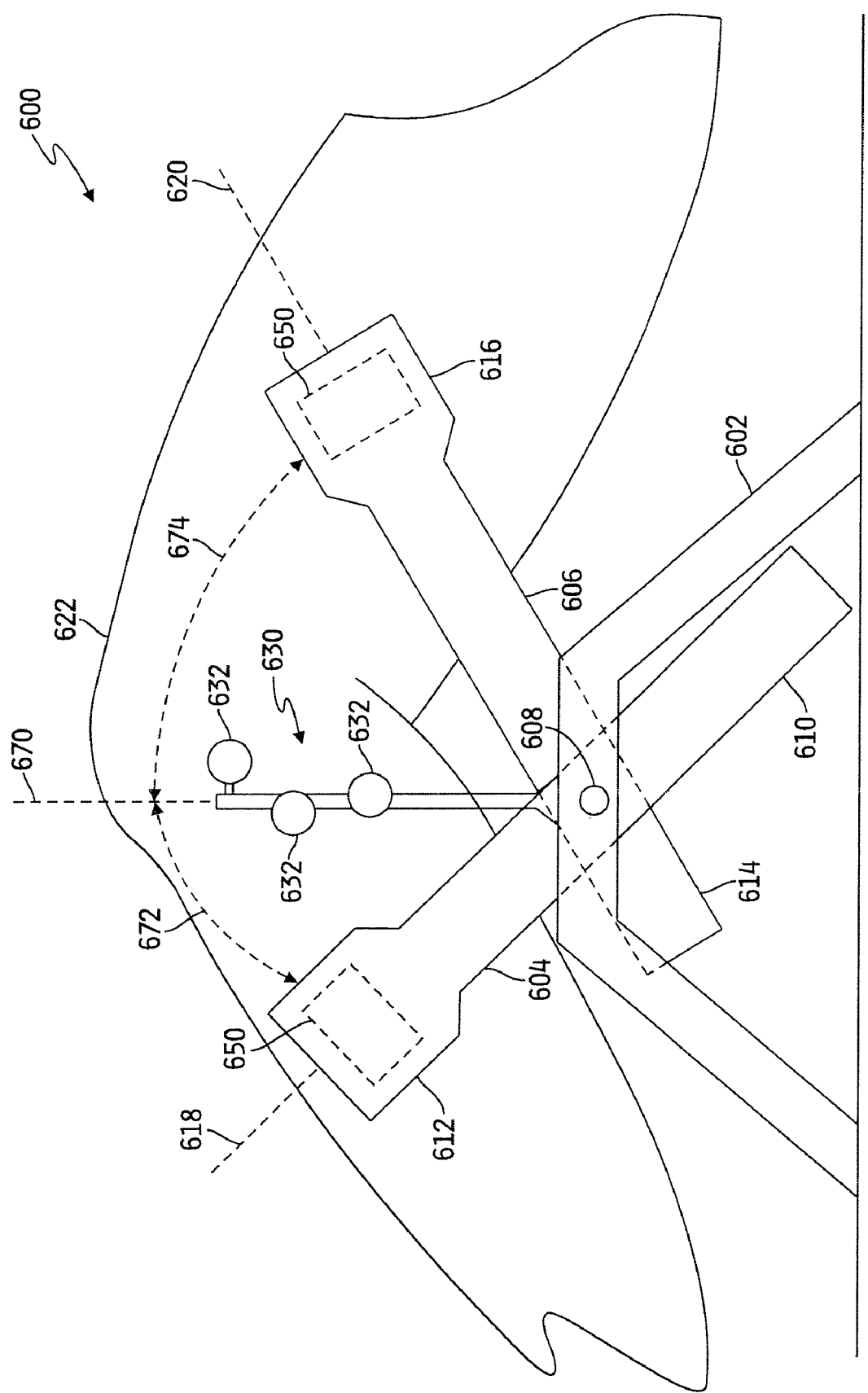
FIG. 35 is a side elevation view of one embodiment of a magnetic sensor apparatus.

Referring now to FIG. 35, in another embodiment, a magnetic sensor apparatus 600 for registering a bone of a patient with a computer assisted surgical system includes a support frame 602, a first magnetic sensor array 604, and a second magnetic sensor array 606. The apparatus 600 also includes a reflective sensor array 630, which is similar to the reflective sensor array 336 of the magnetic sensor array 308. The reflective sensor array 630 includes a number of reflective elements 632 and is used by the controller 302 to determine the relative position of the apparatus 600. The magnetic sensor array 604 includes a arm portion 610 and a sensing head portion 612. Similarly, the magnetic sensor array 606 includes a arm portion 614 and a sensing head portion 616. Each of the magnetic sensor arrays 604, 606 are movably coupled to the support frame 602 via a coupler 608. The coupler 608 allows the magnetic sensor arrays 604, 606 to be pivoted about the support frame 602.

In addition, the magnetic sensor arrays 604, 606 may be translated with respect to the support frame 602. For example, the head portion 612 of the magnetic sensor array 604 may be moved away from or toward the support frame 602 along a longitudinal axis 618. Similarly, the head portion 616 of the magnetic sensor array 606 may be moved away from or toward the support frame 602 along a longitudinal axis 620. By pivoting and/or translating the magnetic sensor arrays 604, 606 with respect to the support frame 602, each of the sensing head portions 612, 616 may be positioned in a magnetic field generated by separate magnets coupled to a bone(s) of a patient. For example, the apparatus 600 may be used to position the sensing heads 612, 616 in magnetic fields generated by magnets implanted in a tibia and femur bone of a patient's leg 622 as illustrated in FIG. 35. As such, the apparatus 600 may be used to sense the magnetic fields of a magnetic source, such as magnetic source 309 embodied as a number of magnets 450, implanted in a single bone or in different bones of the patient. In other embodiments, the apparatus 600 may include additional magnetic sensor arrays, each movably coupled to the support frame such that magnetic fields generated by any number of magnets may be measured.

Figure 36:
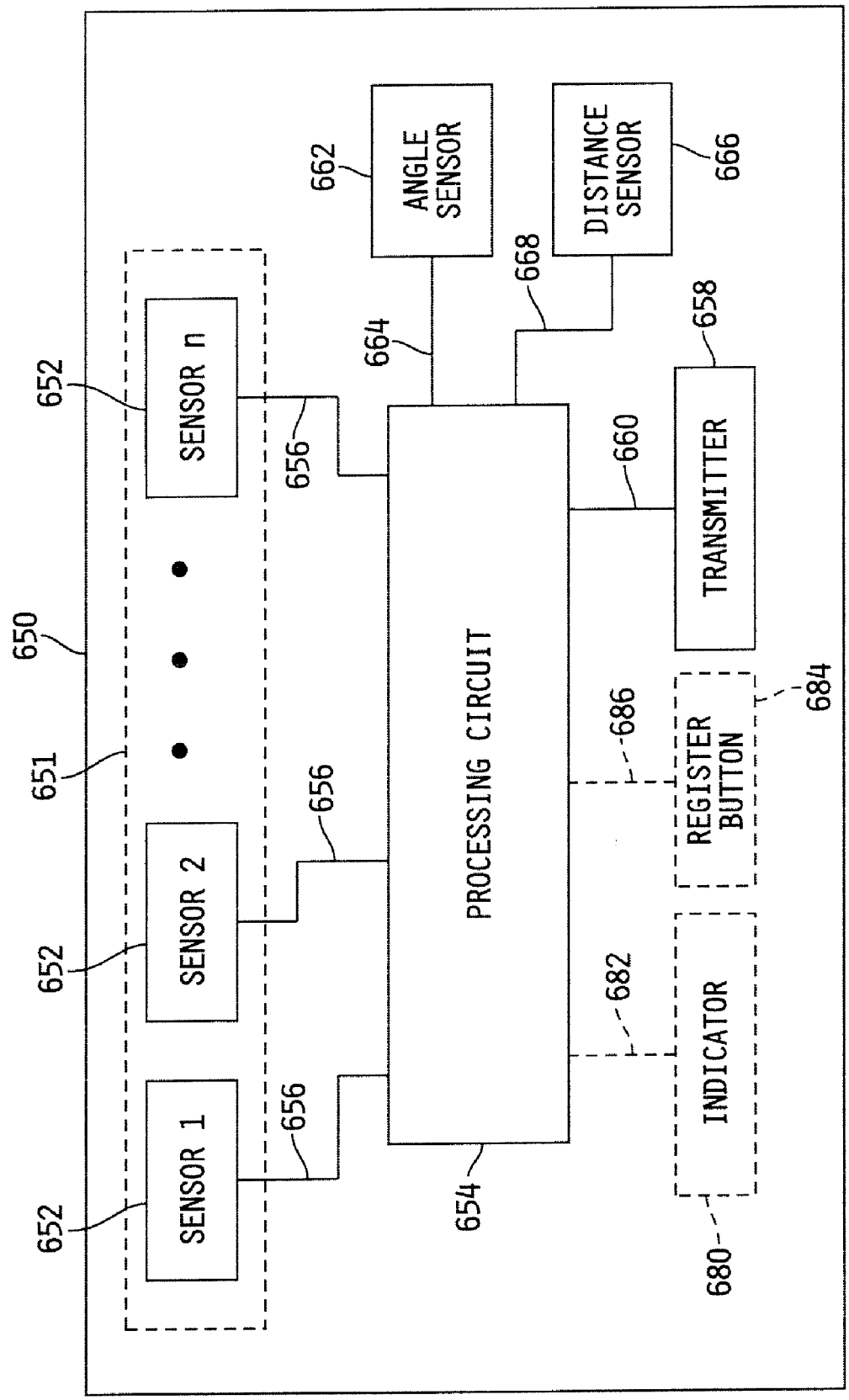
FIG. 36 is a simplified circuit diagram of one embodiment of a sensor circuit of the magnetic sensor apparatus of FIG. 27.

Each of the magnetic sensor arrays 604, 606 includes a sensor circuit 650 located in the sensing head portion 612, 616 of the magnetic sensor arrays 604, 606. As illustrated in FIG. 36, each sensor circuit 650 includes a magnetic sensor arrangement 651. The magnetic sensor arrangement 651 includes one or more magnetic sensors 652. Each sensor circuit 650 also includes a processing circuit 654 electrically coupled to the magnetic sensors 652 via an interconnect 656, a transmitter 658 electrically coupled to the processing circuit 654 via an interconnect 660, an angle sensor 662 electrically coupled to the processing circuit 654 via an interconnect 664, and a distance sensor 666 electrically coupled to the processing circuit 654 via an interconnect 668. The interconnects 656, 660, 664, and 668 may be embodied as any type of interconnects capable of providing electrical connection between the processing circuit 654, the sensors 652, the transmitter 658, the angle sensor 662, and the distance sensor 666 such as, for example, wires, cables, PCB traces, or the like.

Similar to the sensor circuit 328, the number of magnetic sensors 652 included in the sensor circuit 650 may depend on such criteria as the type of magnetic sensors used, the specific application, and/or the configuration of the magnetic sensor arrays 604, 606. For example, the sensor circuit 650 may include any number and configuration of one-dimensional, two-dimensional, and three-dimensional magnetic sensors such that the sensor circuit 650 is capable of sensing or measuring the magnetic field of the magnetic source in three dimensions.

Additionally, the magnetic sensor(s) 652 may be embodied as any type of magnetic sensor capable of sensing or measuring the magnetic field generated by the magnetic source. For example, the magnetic sensors 652 may be embodied as superconducting quantum interference (SQUID) magnetic sensors, anisotropic magnetoresistive (AMR) magnetic sensors, giant magnetoresistive (GMR) magnetic sensors, Hall-effect magnetic sensors, or any other type of magnetic sensor capable of sensing or measuring the three-dimensional magnetic field of the magnetic source. In one particular embodiment, the magnetic sensor(s) are embodied as X-H3X-xx_E3C-25HX-2.5-0.2T Three Axis Magnetic Field Transducers, which are commercially available from SENIS GmbH, of Zurich, Switzerland. The magnetic sensors 652 are configured to produce a number of data values (e.g., voltage levels) which define the three-dimensional magnetic field of the magnetic source. These data values are transmitted to the processing circuit 654 via the interconnects 656.

In some embodiments, the magnetic sensor arrangement 651 of each sensor circuit 650 is substantially similar to the magnetic sensor arrangement 348. For example, the magnetic sensor arrangement 651 may include seventeen magnetic sensors 652 secured to a sensor board similar to magnetic sensors 350 and sensor board 370 illustrated in and described above in regard to FIG. 20.

The processing circuit 654 may be embodied as any collection of electrical devices and circuits configured to determine the position of the magnetic source 309 relative to the magnetic sensor array 604, 606 based on the data values received from the magnetic sensors 652. For example, the processing circuit 654 may include any number of processors, microcontrollers, digital signal processors, and/or other electronic devices and circuits. In addition, the processing circuit 654 may include one or more memory devices for storing software/firmware code, data values, and algorithms.

The processing circuit 654 is configured to determine position data indicative of the position of the magnetic source 309 (e.g., magnets 450) relative to the magnetic sensor array 604, 606. To do so, the processing circuit 654 may determine values of the five degrees or six degrees of freedom of the magnetic source 309. The position data may be embodied as coefficient values or other data usable by the controller 302 to determine the relative position (i.e., location and orientation) of the magnetic source 309. The processing circuit 654 controls the transmitter 658 via interconnect 660 to transmit the position data to the controller 302 via the communication link 326.

The angle sensor 662 and the distance sensor 666 are configured to measure the movement of the magnetic sensor array 604, 606 and transmit the measurements to the processing circuit 654 via the interconnects 664, 668, respectively. For example, the angle sensor 662 measures an angle 672, 674 defined between a vertical reference axis 670 and the magnetic sensor array 604, 606, respectively. In this way, the angle sensor 662 determines the amount of angular distance that the magnetic sensor array 604, 606 has been pivoted from the reference axis 670. Similarly, the distance sensor 666 measures a distance of translational of the magnetic sensor arrays 612, 616 along axes 618, 620, respectively. That is, the distance sensor 666 determines the amount of linear distance that the head portions 612, 616 of the magnetic sensor arrays 604, 606 have been moved along the longitudinal axes 618, 620 from a reference point such as, for example, from coupler 608. The processing circuit 654 receives the angle data and distance data from the angle sensor 662 and the distance sensor 666, respectively. The processing circuit 654 subsequently transmits this data along with the position data indicative of the relative position of the magnetic source to the controller 302 using the transmitter 658. As such, the illustrative apparatus 600 illustrated in FIGS. 35 and 36 includes a transmitter in each sensor circuit 650. However, in other embodiments, the apparatus 600 may include a single transmitter for transmitting all the data to the controller 302. In such embodiments, the sensor circuit 650 the magnetic sensor arrays 604, 606 may be configured to communicate with each other to transmit the angle data, the distance data, and the position data determined by each sensor circuit 650.

In some embodiments, the sensor circuit 650 may also include an indicator 680. The indicator 680 may be embodied as any type of indicator including a visual indicator, an audible indicator, and/or a tactile indicator. The indicator 680 is electrically coupled to the processing circuit 654 via an interconnect 682, which may be similar to interconnects 656, 660, 664, and 668. In such embodiments, the processing circuit 654 is configured to activate the indicator 680 when the magnetic sensor array 604, 606 is positioned in the magnetic field of a magnetic source. For example, the processing circuit 654 may be configured to monitor the magnetic flux density sensed by the magnetic sensor(s) 652 and activate the indicator 680 when the magnetic flux desnity reaches or surpasses a predetermined threshold value. In this way, the magnetic sensor arrays 604, 606 may be positioned by pivoting and translating the arrays 604, 606 with respect to the support frame 602 until the magnetic sensor arrays 604, 606 are positioned in a magnetic field of a magnetic source (i.e., a magnet that forms a portion of the magnetic source). Once so positioned, the indicator 680 will be activated to notify the surgeon that the sensor arrays 604, 606 are properly positioned.

Further, in some embodiments the sensor circuit 650 may include a register button 684. The register button 684 may be located on an outside surface of the magnetic sensor array 604, 606 such that the button 684 is selectable by a user of the apparatus 600. The button 684 may be embodied as any type of button such as a push button, toggle switch, software implemented touch screen button, or the like. The register button 684 is electrically coupled to the processing circuit 654 via an interconnect 686, which may be similar to interconnects 656, 660, 664, and 668. The functionality of the register button 684 is substantially similar to the functionality of the register button 364 of the sensor circuit 328. That is, the register button 684 may be selected by a user, such as an orthopaedic surgeon, of the apparatus 600 to transmit the position data and/or measurement values of the magnetic sensors 652 to the controller 302. In some embodiments, a single register button 684 may be included and selectable by the orthopedic surgeon to transmit the position data of both magnetic sensor arrays 604, 606 contemporaneously with each other.

Figure 37:
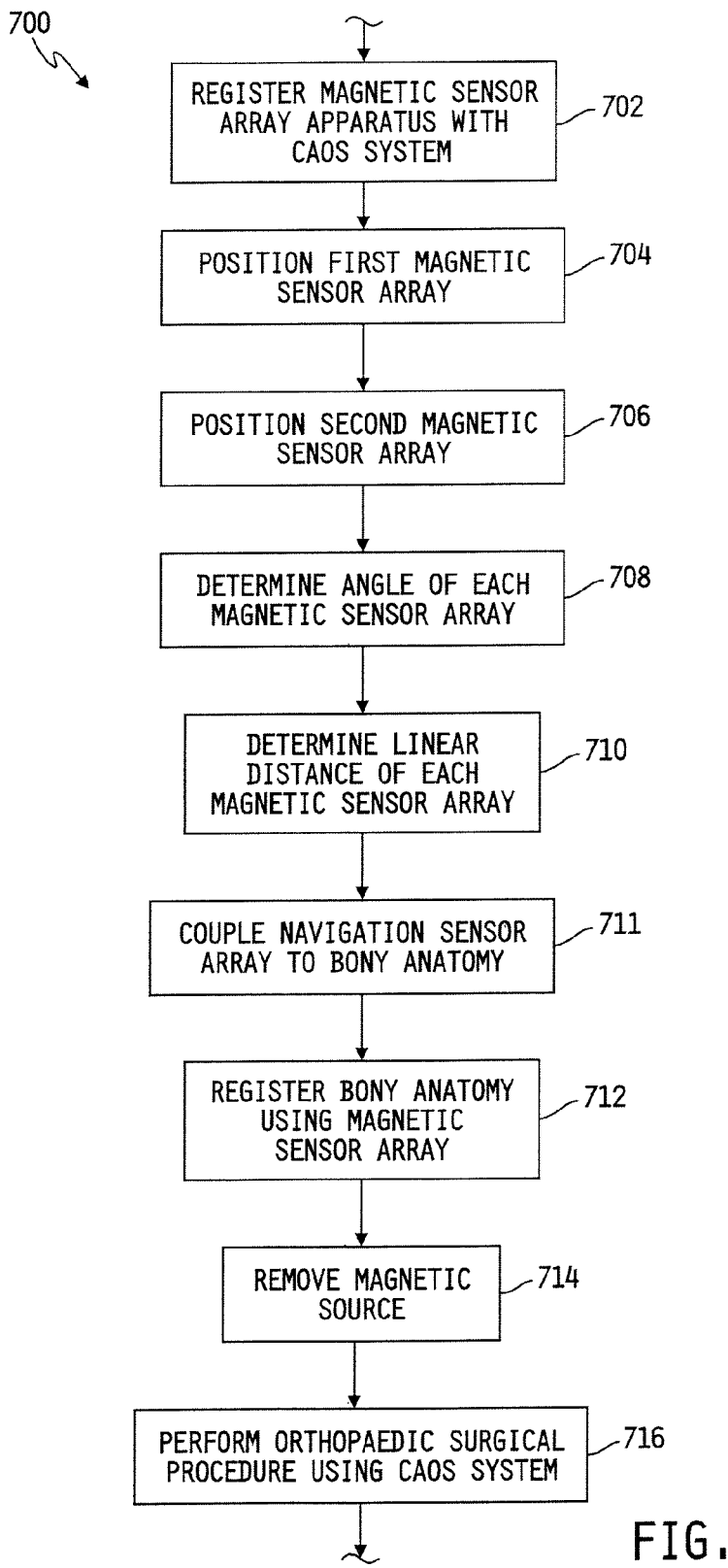
FIG. 37 is a simplified flowchart of an algorithm for registering a bone with a CAOS system using the magnetic sensor apparatus of FIG. 27.
Figure 38:
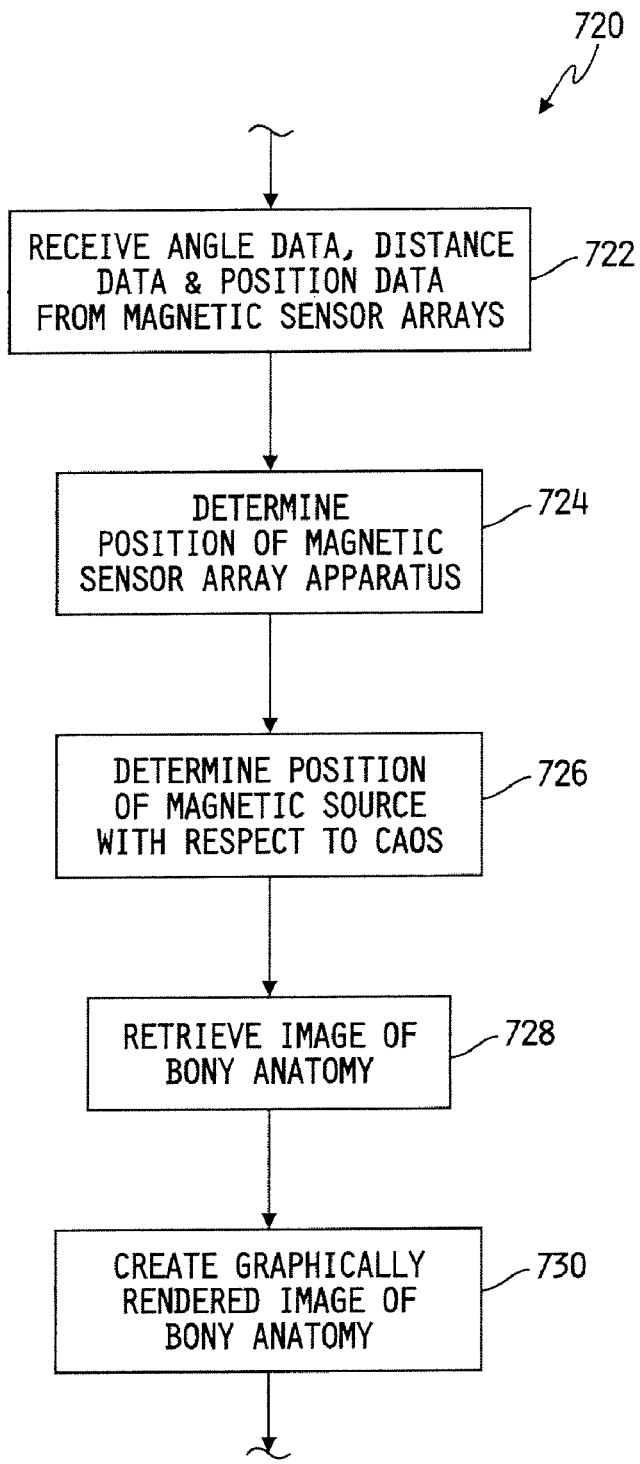
FIG. 38 is a simplified flowchart of a sub-algorithm of the algorithm of FIG. 29.

Referring now to FIGS. 37 and 38, an algorithm 700 may be used with the apparatus 600 to register a bone or bones of a patient with a CAOS system such as controller 302. The algorithm 700 is described below with respect to the use of the apparatus 600 and magnetic source 309 embodied as two magnets 450. However, other magnetic sources having any number of magnets may be used. Additionally, initial steps similar to process steps 402, 404, and 406 of algorithm 400 have been omitted from algorithm 700 for clarity of description. However, it should be appreciated that such steps may be used with algorithm 700 as well. For example, the individual magnetic sensor arrays 604, 606 of the apparatus 600 may be calibrated to compensate for environmental magnetic field effects and/or offset voltages of the magnetic sensors 650. Additionally, the magnetic source 309 is coupled to or implanted in the relevant bony anatomy of the patient, as discussed in detail above in regard to process step 404, prior to the execution of the algorithm 700. Further, images of the bone(s) having the magnetic source 309 coupled therewith are generated prior to the execution of the algorithm 700. To do so, the algorithm 800 illustrated in and described above in regard to FIG. 25 may be used.

Algorithm 700 begins with process step 702 in which the apparatus 600 is registered with the controller 302. To register the apparatus 600, the apparatus 600 is positioned in the field of view of the camera unit 304 such that the reflective sensor array 630 is viewable by the camera unit 304. In one particular embodiment, the apparatus 600 is secured to the ceiling or a wall of the operating room or to the operating room table upon which the orthopaedic surgical procedure will be performed. As such, the camera unit 304 may be positioned such that the apparatus 600 is in the field of view of the camera unit 304. Appropriate commands are given to the controller 302 such that the controller 302 identifies the apparatus 600 via the reflective sensor array 630 coupled thereto. The controller 302 is then capable of determining the relative position of the apparatus 600 using the reflective sensor array 630.

Once the apparatus 600 has been registered with the controller 302, the first magnetic sensor array 604 is positioned in process step 704. The magnetic sensor array 604 is positioned such that the sensor circuit 650 of the magnetic sensor array 604 is located in the magnetic field generated by a first magnet 450 that forms a portion of the magnetic source 309. Subsequently, in process step 706, the second magnetic sensor array 606 is positioned. Similar to the magnetic sensor array 604, the magnetic sensor array 606 is positioned such that the sensor circuit 650 of the magnetic sensor array 606 is located in the magnetic field generated by a second magnet 450 that forms a portion of the magnetic source 309. The magnetic sensor arrays 604, 606 may be positioned by moving (i.e., pivoting and translating) the arrays 604, 606 about the frame 602. The magnetic sensor arrays 604, 606 may be so positioned by using the indicators 680 of the sensor circuits 650 as discussed above in regard to FIG. 36.

The magnetic sensor arrays 604, 606 may be positioned in a manner similar to that of magnetic sensor array 308 described above in regard to algorithm 820 illustrated in FIG. 26. That is, the magnetic sensor arrays 604, 606 are positioned such that each sensor circuit 650 is on-axis with the magnetic moment of the respective magnet 450. As discussed above in regard to the magnetic sensor array 308, each of sensing head portions 612, 616 may be positioned such that a central magnetic sensor 652 of the magnetic sensor arrangement 651 is substantially on axis with the magnetic moment of each magnet 450. To do so, each sensor circuit 650 may be configured to monitor the X-component and Y-component output measurements of the central magnetic sensor 652 and determine the proper positioning based on when such measurements reach a minimum value or fall below a threshold value, as discussed in more detail above in regard to process step 822 of algorithm 820. Alternatively, as discussed above in regard to the magnetic sensor array 308, the sensor circuits 650 may be configured to adapt to non-alignment of the sensor circuits 650 with respect to the magnets 450 by determining which individual magnetic sensor 652 is on-axis or closest to on-axis with the magnetic moments of the magnets 450 and adjusting the magnetic field measurements of the remaining magnetic sensors 652 accordingly.

Once the magnetic sensor arrays 604, 606 have been properly positioned, the position of the magnetic sensor arrays 604, 606 are determined in process steps 708, 710. To do so, in process step 708, the angle sensor 662 of the sensor circuit 650 determines the angle 672, 674 defined between the vertical reference axis 670 and the magnetic sensor array 604, 606. Additionally, in process step 710, the distance sensor 666 determines the linear distance that the sensing head portion 612, 616 of the respective magnetic sensor array 604, 606 has been moved along the respective longitudinal axis 618, 620 from a predetermined reference point such as, for example, the coupler 608. The angle and distance data is subsequently transmitted to the processing circuit 654 from the angle sensor 662, and distance sensor 666, respectively.

In process step 711, a navigation sensor array is coupled to the relevant bone or bones of the patient. The navigation sensor array is similar to sensor array 54 illustrated in and described above in regard to FIG. 2. Similar to sensor array 54, the navigation sensor array may be a reflective sensor array similar to reflective sensor arrays 336 and 514 or may be an electromagnetic or radio frequency (RF) sensor array and embodied as, for example, a wireless transmitter. Regardless, the navigation sensor array is coupled to the relevant bony anatomy of the patient such that the navigation sensor array is within the field of view of the camera unit 304. The controller 302 utilizes the navigation sensor array to determine movement of the bony anatomy once the bony anatomy has been registered with the computer assisted orthopaedic surgery (CAOS) system 301 as discussed below in regard to process step 712. Although process step 711 is illustrated in FIG. 37 as immediately following process step 710, it should be appreciated that the navigational sensor array may be coupled to the relevant bone of the patient at any time prior to the registration of the bony anatomy in process step 712.

After the position of the magnetic sensor arrays 604, 606 has been determined, the bone or bony anatomy of the patient having the magnetic source coupled thereto is registered with the controller 302 in process step 712. To do so, the position of the magnetic source 309 (i.e., the magnets 450) with respect to each magnetic sensor array 604, 606 is first determined. The magnetic sensor arrays 604, 606 (i.e., sensor circuits 650) may execute the algorithms 830 for determining a position of a magnetic source described above in regard to and illustrated in FIG. 27. In some embodiments, the algorithm 830 is executed solely by the magnetic sensor arrays 604, 606. However, in other embodiments, the magnetic sensor arrays 604, 606 may be configured only to measure the magnetic field of the respective magnets 450 and transmit such measurement values to the controller 302. In such embodiments, the process steps 834-842 of algorithm 800 are executed by the controller 302 after receiving the measurement values from the magnetic sensor arrays 604, 606.

Once the position of the magnetic source 309 relative to the magnetic sensor arrays 604, 606 has been determined, the position data indicative thereof is transmitted to the controller 302. In addition, the angle data indicative of the angular displacement of the magnetic sensor array 604, 606 and the distance data indicative of the linear displacement of the magnetic sensor array 604, 606 is transmitted to the controller 302 via the communication link 326.

In response to the received data, the controller 302 determines the position of the relevant bony anatomy of the patient. To do so, the controller 302 may execute an algorithm 720 as illustrated in FIG. 38. Similar to algorithm 420 illustrated in and described above in regard to FIG. 28, the algorithm 720 may be embodied as software or firmware stored in, for example, the memory device 316. The algorithm 720 begins with process step 722 in which the controller 302 receives the position data, the angle data, and the distance data from each of the magnetic sensors 604, 606 via the communication link 326. As discussed above, the position data is indicative of the position of the magnetic source 309 (e.g., the magnets 450) relative to the respective magnetic sensor array 604, 606. In the illustrative embodiment, the position data is embodied as coefficient values that define the five degrees of freedom (i.e., X-coordinate, Y-coordinate, Z-coordinate, (theta) θ-rotational, and (phi) ϕ-rotational) of the magnetic source 309 and thereby the bony anatomy to which the magnetic source 309 is coupled. However, other types of position data that define the location and orientation of the magnetic source 309 and bony anatomy may be used in other embodiments. Once the data is received from the magnetic sensor arrays 604, 606, the controller 302 may store the position data, angle data, and distance data in the memory device 316.

In process step 724, the controller 302 determines the position of the apparatus 600. To do so, the controller 302 receives images from the camera unit 304 via the communication link 310. By analyzing the position of the reflective sensor array 630 in the images, the controller 302 determines the position of the magnetic sensor apparatus 600 relative to a reference point such as, for example, the camera 304 and/or the controller 302.

Subsequently, in process step 726, the controller 302 determines the position of the magnetic source 309 with respect to the computer assisted orthopaedic surgery (CAOS) system 301. To do so, the controller 302 uses the position data indicative of the position of the magnetic source 309 relative to the magnetic sensor arrays 604, 606, the angle data indicative of the angular displacement of the magnetic sensor arrays 604, 606 from the vertical reference axis 670, the distance data indicative of the linear displacement of the magnetic sensor arrays 604, 606 from a reference point such as the coupler 608, and the position of the apparatus 600 determined in process step 424. That is, because the controller 302 has determined the position of the apparatus 600 within the coordinate system of the computer assisted orthopaedic surgery (CAOS) system 301, the controller 302 can determine the position of the magnetic sensor arrays 604, 606 in the same coordinate system based on the angle data and distance data using an appropriate algorithm such as a vector addition algorithm. Similarly, because the magnetic sensor arrays 604, 606 have determined the position of the magnetic source 309 relative to the arrays 604, 606 themselves, the controller 302 can determine the position of the magnetic source 309 in the coordinate system of the computer assisted orthopaedic surgery (CAOS) system 301 (i.e., with respect to the CAOS system 301) by combining the position data of the magnetic sensor arrays 604, 606 within the coordinate system and the position data of the magnetic source 309 relative to the magnetic sensor arrays 604, 606 using an appropriate algorithm (e.g., a vector addition algorithm).

Subsequently, in process step 728, the controller 302 retrieves the three-dimensional image of the bony anatomy that was previously generated. To do so, the controller 302 may retrieve the image from the database 318 and/or from the remote database 320. The image may be so retrieved based on any suitable criteria. For example, in one embodiment, the image is retrieved based on patient identification data. In such embodiments, the patient identification data may be supplied to the controller prior to the performance of the orthopaedic surgical procedure. The controller may retrieve any number of generated images. The generated images include indicia or images of the magnetic source 309 (e.g., the two magnets 450) and its position with respect to the bony anatomy.

In process step 730, the controller 302 creates a graphically rendered image of the bony anatomy having a location and orientation based on the position of the magnetic source 309 determined in process step 726 and surface contours based on the image(s) of the bony anatomy retrieved in process step 728. However, because only five degrees of freedom of the magnetic source 309 were determined and transmitted to the controller 302, the controller 302 must determine the sixth degree of freedom of the magnetic source 309. In some embodiments, the sixth degree of freedom is already determined or known by the controller 302. For example, in embodiments wherein the magnets 450 are implanted into the relevant bone(s) at a predetermined angle with respect to each other, such predetermined angle may be supplied to the controller 302 as the sixth degree of freedom. Alternatively, in embodiments wherein the three-dimensional image(s) of the relevant bony anatomy and magnetic source 309 is determined using the algorithm 800 described above in regard to FIG. 25, the 1×5 matrix including the three components of the translation vector between the centroids of the magnets 450 and two angular rotations defining the spatial relationship between the two magnets 450 may have been determined in process step 810. However, even if the matrix has not been previously determined, the controller 302 may be configured to determine the matrix in process step 750. To do so, the controller 302 may execute the algorithm 850 described above in regard to and illustrated in FIG. 28.

Once the six degrees of freedom of the magnetic source 309 has been determined, the rendered image of the bony anatomy may be generated in process step 750 based on the six degrees of freedom of the magnetic source 309 and the data indicative of the positional relationship between the magnetic source and the bony anatomy as determined in process step 808 of algorithm 800. That is, because the six degrees of freedom of the magnetic source 309 is known and the positional relationship between the bony anatomy and the magnetic source 309 is known, the six degrees of freedom of the bony anatomy may be determined by, for example, simple vector addition. The rendered image may be displayed to the surgeon or other user of the CAOS system 300 on the display device 306 using the communication link 312.

Referring back to algorithm 700 in FIG. 37, after the bony anatomy has been registered in process step 712, the magnetic source 309 may be decoupled from the bony anatomy of the patient in process step 714. To do so, the magnetic sensor arrays 604, 606 may be used to determine the location of the individual magnets 450 which form the magnetic source 309. For example, the magnetic sensor arrays 604, 606 may be passed over the skin of the patient until the indicators 680 of the magnetic sensor arrays 604, 606 are activated, which indicates that the magnetic sensor arrays 604, 606 are in the respective magnetic field of the magnets 450. The individual magnets 450 may then be removed using an appropriate surgical procedure. In other embodiments, such as those embodiments wherein the sensor arrays 54 are embodied as wireless transmitters (i.e., electromagnetic sensor arrays) rather than reflective sensor arrays, the magnetic source 309 may be decoupled from the bone(s) of the patient prior to the performance of the orthopaedic surgical procedure so as to avoid any magnetic interference with the operation. of the sensor arrays 54. Again, however, if the magnetic source 309 is left coupled to the bone(s) of the patient during the performance of the orthopaedic surgical procedure, the bone(s) may be reregistered at any time and as often as necessary during the procedure.

In process step 716, the orthopaedic surgical procedure is performed. The orthopaedic surgical procedure is performed using the images of the relevant bony anatomy generated in process step 73 of algorithm 720, which is displayed on the display device 306 in a position and orientation based on the position data, angle data, and distance data received from the magnetic sensor arrays 604, 606 and the generated images of the bony anatomy having indicia of the position of the magnetic source coupled therewith. The surgeon may use the system 300 to navigate and step through the orthopaedic surgical process in a similar manner as the CAOS system 10 illustrated in and described above in regard to FIGS. 1-17. For example, navigation with respect to the bony anatomy may be facilitated by the use of a reflective sensor array, such as one similar to the tibial array 60 of FIG. 3, coupled to the bony anatomy. It should be appreciated, however, that the present algorithm 700 for registering the bone anatomy of a patient may partially or completely replace the process step 106 of the algorithm 100 illustrated in and described above in regard to FIG. 6.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A magnetic sensor array for measuring a magnetic field generated by a magnetic source, the magnetic sensor array comprising:
   a planar substrate having an upper surface, the planar substrate including only one set of magnetic sensors, the set of magnetic sensors consisting of:
   a first three-dimensional magnetic sensor secured to the upper surface of the substrate at a central location;
   a plurality of second three-dimensional magnetic sensors each secured to the upper surface of the substrate at a first distance from the first three-dimensional magnetic sensor; and
   a plurality of first one-dimensional magnetic sensors each secured to the upper surface of the substrate at a second distance from the first magnetic sensor that is greater than the first distance, the plurality of first one-dimensional magnetic sensors being configured to measure a Z-component of the three-dimensional magnetic flux density of the magnetic field at a point in space.

2. The magnetic sensor array of claim 1, wherein each of the second three-dimensional magnetic sensors has a lower magnetic field sensitivity and a greater sensing range than each of the first one-dimensional magnetic sensors.

3. The magnetic sensor array of claim 1, wherein the substrate is formed from an FR4 material.

4. The magnetic sensor array of claim 1, further comprising a processing circuit electrically coupled to each of the first three-dimensional magnetic sensor, the second three-dimensional magnetic sensors, and the first one-dimensional magnetic sensors.

5. The magnetic sensor array of claim 4, further comprising a third three-dimensional magnetic sensor spaced apart from the substrate and electrically coupled to the processing circuit.

6. The magnetic sensor array of claim 5, wherein the third three-dimensional magnetic sensor is configured to measure at least one environmental magnetic field.

7. The magnetic sensor array of claim 5, wherein the processing circuit is configured to compensate output signals of at least one of the first three-dimensional magnetic sensor, the second three-dimensional magnetic sensors, and the first one-dimensional magnetic sensors based on an output of the third three-dimensional magnetic sensor.

8. The magnetic sensor array of claim 5, wherein the processing circuit is configured to compensate output signals of at least one of the first three-dimensional magnetic sensor, the second three-dimensional magnetic sensors, and the first one-dimensional magnetic sensors based on an offset voltage produced by the at least one of the first three-dimensional magnetic sensor, the second three-dimensional magnetic sensors, and the first one-dimensional magnetic sensors.

9. The magnetic sensor array of claim 1, wherein the plurality of the second three-dimensional magnetic sensors and the plurality of the first one-dimensional magnetic sensors are circumferentially spaced around the first three-dimensional magnetic sensor.

10. An apparatus for measuring a magnetic field of a magnetic source, the magnetic field being defined by a three-dimensional magnetic flux density at a plurality of points in space, the apparatus comprising:
a hand-held housing including a handle and a sensing head portion;
a planar substrate coupled to the housing and located in the sensing head portion, the planar substrate including only one set of magnetic sensors, the set of magnetic sensors consisting of:
a first three-dimensional magnetic sensor coupled to the planar substrate and configured to measure an X-component, a Y-component, and a Z-component of the three dimensional magnetic flux at a point in space;
a plurality of second three-dimensional magnetic sensors coupled to the planar substrate a first distance from the first three-dimensional magnetic sensor, each of the plurality of second three-dimensional magnetic sensors being configured to measure the X-component, the Y-component, and the Z-component of the three dimensional magnetic flux at a point in space;
a plurality of first one-dimensional magnetic sensors coupled to the planar substrate a second distance from the first three-dimensional magnetic sensor greater than the first distance, each of the plurality of first one-dimensional magnetic sensors being configured to measure the Z-component of the three-dimensional magnetic flux density at a point in space;
a plurality of second one-dimensional magnetic sensors coupled to the planar substrate a third distance from the first three-dimensional magnetic sensor greater than the second distance, each of the plurality of second one-dimensional magnetic sensors being configured to measure the Z-component of the three-dimensional magnetic flux density at a point in space; and
a plurality of third one-dimensional magnetic sensors coupled to the planar substrate a fourth distance from the first three-dimensional magnetic sensor greater than the third distance, a first number of the plurality of third one-dimensional magnetic sensors being configured to measure the X-component of the three-dimensional magnetic flux density at a point in space and a second number of the plurality of third one-dimensional magnetic sensors being configured to measure the Y-component of the three-dimensional magnetic flux density at a point in space.

11. The apparatus of claim 10, wherein each of the first three-dimensional magnetic sensor, the second three-dimensional magnetic sensors, the first one-dimensional magnetic sensors, and the second one-dimensional magnetic sensors is coupled to a top surface of the substrate.

12. The apparatus of claim 11, wherein each of the plurality of third one-dimensional magnetic sensors is positioned substantially orthogonally to the top surface of the substrate.

13. A magnetic sensor array for measuring a magnetic field generated by a magnetic source, the magnetic sensor array comprising:
a planar substrate having an upper surface, a first side surface connected to the upper surface to define a first edge, and a second side surface opposite the first side surface and connected to the upper surface to define a second edge opposite the first edge, the planar substrate including only one set of magnetic sensors, the set of magnetic sensors consisting of:
a first three-dimensional magnetic sensor secured to the upper surface of the substrate at a central location;
a plurality of second three-dimensional magnetic sensors each secured to the upper surface of the substrate at a first distance from the first three-dimensional magnetic sensor, at least one of the plurality of second three-dimensional magnetic sensors being positioned between the first three-dimensional magnetic sensor and the first edge, and at least one of the plurality of second three-dimensional magnetic sensor being positioned between the first three-dimensional magnetic sensor and the second edge; and
a plurality of first one-dimensional magnetic sensors each secured to the upper surface of the substrate at a second distance from the first magnetic sensor, the second distance being greater than the first distance, at least one of the plurality of first one-dimensional magnetic sensors being positioned between the first three-dimensional magnetic sensor and the first edge, and at least one of the plurality of first one-dimensional magnetic sensors being positioned between the first three-dimensional magnetic sensor and the second edge.

14. A magnetic sensor array for measuring a magnetic field generated by a magnetic source, the magnetic sensor array comprising:
a planar substrate having an upper surface, the planar substrate including only one set of magnetic sensors, the set of magnetic sensors consisting of:
a first three-dimensional magnetic sensor secured to the upper surface of the substrate at a central location;
a plurality of second three-dimensional magnetic sensors each secured to the upper surface of the substrate at a first distance from the first three-dimensional magnetic sensor; and
a plurality of first one-dimensional magnetic sensors each secured to the upper surface of the substrate at a second distance from the first magnetic sensor that is greater than the first distance, the plurality of first one-dimensional magnetic sensors being configured to measure one of: (i) an X-component of the three-dimensional magnetic flux density of the magnetic field at a point in space, (ii) a Y-component of the three-dimensional magnetic flux density of the magnetic field at a point in space, or (iii) a Z-component of the three-dimensional magnetic flux density of the magnetic field at a point in space.

* * * * *